US011518816B2

(12) United States Patent
Subramanian et al.

(10) Patent No.: US 11,518,816 B2
(45) Date of Patent: Dec. 6, 2022

(54) METHODS OF DELIVERING AN OLIGONUCLEOTIDE TO A SUBJECT HAVING FACIOSCAPULOHUMERAL MUSCULAR DYSTROPHY

(71) Applicant: Dyne Therapeutics, Inc., Waltham, MA (US)

(72) Inventors: Romesh R. Subramanian, Framingham, MA (US); Mohammed T. Qatanani, Waltham, MA (US); Timothy Weeden, Waltham, MA (US)

(73) Assignee: Dyne Therapeutics, Inc., Waltham, MA (US)

( * ) Notice: Subject to any disclaimer, the term of this patent is extended or adjusted under 35 U.S.C. 154(b) by 0 days.

(21) Appl. No.: 17/846,738

(22) Filed: Jun. 22, 2022

(65) Prior Publication Data

US 2022/0324992 A1  Oct. 13, 2022

Related U.S. Application Data

(63) Continuation of application No. 17/671,707, filed on Feb. 15, 2022, now Pat. No. 11,390,682, which is a continuation of application No. 17/400,295, filed on Aug. 12, 2021, now Pat. No. 11,286,305, which is a continuation of application No. 17/205,123, filed on Mar. 18, 2021, now Pat. No. 11,111,309, which is a continuation of application No. 17/264,948, filed as application No. PCT/US2019/044990 on Aug. 2, 2019.

(60) Provisional application No. 62/713,933, filed on Aug. 2, 2018.

(51) Int. Cl.
*C07K 16/28* (2006.01)
*C12N 15/113* (2010.01)

(52) U.S. Cl.
CPC ........ *C07K 16/2881* (2013.01); *C12N 15/113* (2013.01); *C07K 2317/55* (2013.01); *C07K 2317/92* (2013.01)

(58) Field of Classification Search
CPC ............ C07K 16/2881; C07K 2317/55; C07K 2317/92; C12N 15/113
See application file for complete search history.

(56) References Cited

U.S. PATENT DOCUMENTS

| | | | |
|---|---|---|---|
| 2,631,173 A | 3/1953 | Hillyer et al. |
| 6,214,345 B1 | 4/2001 | Firestone et al. |
| 7,064,142 B2 | 6/2006 | Sato et al. |
| 7,265,131 B2 | 9/2007 | Johnson et al. |
| 7,575,886 B2 | 8/2009 | Venkataraman et al. |
| 8,859,629 B2 | 10/2014 | van Delft et al. |
| 8,952,147 B2 | 2/2015 | Bouchard et al. |
| 9,222,940 B2 | 12/2015 | van Delft et al. |
| 9,260,371 B2 | 2/2016 | Bertozzi et al. |
| 9,504,758 B2 | 11/2016 | van Delft et al. |
| 9,550,834 B2 | 1/2017 | Shirai et al. |
| 9,708,406 B2 | 7/2017 | Zhang et al. |
| 9,988,628 B2 | 6/2018 | Belayew et al. |
| 10,131,682 B2 | 11/2018 | Zhao |
| 10,239,807 B2 | 3/2019 | van Delft et al. |
| 10,266,502 B2 | 4/2019 | van Delft et al. |
| 10,434,111 B2 | 10/2019 | Bertozzi et al. |
| 10,538,763 B2 | 1/2020 | Rigo et al. |
| 10,550,188 B2 | 2/2020 | Geall et al. |
| 10,865,445 B2 | 12/2020 | van Der Maarel et al. |
| 10,907,157 B2 | 2/2021 | Belayew et al. |
| 11,111,309 B2 | 9/2021 | Subramanian et al. |
| 11,168,141 B2 | 11/2021 | Subramanian et al. |
| 11,248,056 B1 | 2/2022 | Subramanian et al. |
| 11,286,305 B2 | 3/2022 | Subramanian et al. |
| 11,369,689 B2 | 6/2022 | Subramanian et al. |
| 11,390,682 B2 | 7/2022 | Subramanian et al. |
| 2004/0063654 A1 | 4/2004 | Davis et al. |
| 2005/0084906 A1 | 4/2005 | Goetsch et al. |
| 2005/0282252 A1 | 12/2005 | Siegel |
| 2006/0110782 A1 | 5/2006 | Bertozzi et al. |
| 2006/0252107 A1 | 11/2006 | Kubota et al. |
| 2012/0122801 A1 | 5/2012 | Platenburg |
| 2012/0225034 A1 | 9/2012 | Belayew et al. |
| 2013/0028891 A1 | 1/2013 | Penichet et al. |
| 2013/0066063 A1 | 3/2013 | Berry et al. |
| 2013/0137763 A1 | 5/2013 | van Delft et al. |

(Continued)

FOREIGN PATENT DOCUMENTS

| | | |
|---|---|---|
| EP | 2623609 B1 | 1/2017 |
| EP | 3192880 A1 | 7/2017 |

(Continued)

OTHER PUBLICATIONS

Malik-Adamian E, et al. (2018) J. Org. Chem. 83(17):9839-9849. (doi.org/10.1021/acs.joc.8b01329).*
[No Author Listed] UniProtKB/Swiss-Prot P02786. Transferrin receptor protein 1. Jul. 18, 2018. Retrieved from the Internet Oct. 23, 2019: https://www.uniprot.org/uniprot/P02786.txt?version=225, 20 pages.
[No Author Listed] Wikipedia, Mannose 6-phosphate receptor, Mar. 23, 2018. Retrieved from the internet Nov. 6, 2019: https://en.wikipedia.org/w/index.php?title=Mannose_6-phosphate_receptor&oldid=832003836, 8 pages.
[No Author Listed], Building the world's leading muscle disease company. Dyne Company Overview. Jun. 2021. 46 pages.

(Continued)

*Primary Examiner* — Robert S Landsman
(74) *Attorney, Agent, or Firm* — Wolf, Greenfield & Sacks, P.C.

(57) ABSTRACT

Aspects of the disclosure relate to complexes comprising a muscle-targeting agent covalently linked to a molecular payload. In some embodiments, the muscle-targeting agent specifically binds to an internalizing cell surface receptor on muscle cells. In some embodiments, the molecular payload inhibits expression or activity of DUX4. In some embodiments, the molecular payload is an oligonucleotide, such as an antisense oligonucleotide or RNAi oligonucleotide.

23 Claims, 6 Drawing Sheets

Specification includes a Sequence Listing.

(56) References Cited

U.S. PATENT DOCUMENTS

| | | |
|---|---|---|
| 2013/0177579 A1 | 7/2013 | Lin et al. |
| 2014/0105873 A1 | 4/2014 | Belayew et al. |
| 2014/0193436 A1 | 7/2014 | Prudent |
| 2014/0323552 A1 | 10/2014 | Burghes et al. |
| 2014/0363455 A1 | 12/2014 | Stull et al. |
| 2015/0258210 A1 | 9/2015 | van Delft et al. |
| 2016/0107999 A1 | 4/2016 | Debets et al. |
| 2016/0175460 A1 | 6/2016 | Arathoon et al. |
| 2016/0235861 A1 | 8/2016 | van Delft et al. |
| 2016/0250347 A1 | 9/2016 | van Delft et al. |
| 2016/0272973 A1 | 9/2016 | Shehadeh |
| 2016/0355599 A1 | 12/2016 | Sagert et al. |
| 2017/0002012 A1 | 1/2017 | van Delft et al. |
| 2017/0008858 A1 | 1/2017 | van Delft et al. |
| 2017/0029849 A1 | 2/2017 | Harper et al. |
| 2017/0072068 A1 | 3/2017 | Verkade et al. |
| 2017/0130256 A1 | 5/2017 | van Berkel et al. |
| 2017/0226554 A1 | 8/2017 | Wasiel et al. |
| 2017/0281795 A1 | 10/2017 | Geall et al. |
| 2018/0002433 A1 | 1/2018 | Zhang et al. |
| 2018/0134797 A1 | 5/2018 | Zhang et al. |
| 2018/0265870 A1 | 9/2018 | Belayew et al. |
| 2018/0369400 A1 | 12/2018 | Levin et al. |
| 2019/0000986 A1 | 1/2019 | Levin et al. |
| 2019/0038765 A1 | 2/2019 | van Berkel et al. |
| 2019/0092833 A1 | 3/2019 | Lin et al. |
| 2019/0092870 A1 | 3/2019 | Launay et al. |
| 2019/0153083 A1 | 5/2019 | Juste et al. |
| 2019/0240346 A1 | 8/2019 | Sugo et al. |
| 2020/0046742 A1 | 2/2020 | Bertozzi et al. |
| 2020/0048174 A1 | 2/2020 | van Delft et al. |
| 2020/0248179 A1 | 8/2020 | Harper |
| 2020/0282074 A1 | 9/2020 | Levin et al. |
| 2020/0325237 A1 | 10/2020 | Darimont et al. |
| 2021/0163941 A1 | 6/2021 | Belayew et al. |
| 2021/0163942 A1 | 6/2021 | Belayew et al. |
| 2021/0187116 A1 | 6/2021 | Geall et al. |
| 2021/0206868 A1 | 7/2021 | Subramanian et al. |
| 2021/0220479 A1 | 7/2021 | Subramanian et al. |
| 2021/0228730 A1 | 7/2021 | Subramanian et al. |
| 2021/0230290 A1 | 7/2021 | Subramanian et al. |
| 2021/0261680 A1 | 8/2021 | Subramanian et al. |
| 2021/0308272 A1 | 10/2021 | Subramanian et al. |
| 2021/0308273 A1 | 10/2021 | Subramanian et al. |
| 2021/0308274 A1 | 10/2021 | Subramanian et al. |
| 2021/0317226 A1 | 10/2021 | Subramanian et al. |
| 2021/0322562 A1 | 10/2021 | Subramanian et al. |
| 2021/0322563 A1 | 10/2021 | Subramanian et al. |
| 2021/0324101 A1 | 10/2021 | Subramanian et al. |
| 2021/0380709 A1 | 12/2021 | Subramanian et al. |
| 2022/0025066 A1 | 1/2022 | Subramanian et al. |
| 2022/0143206 A1 | 5/2022 | Subramanian et al. |
| 2022/0169743 A1 | 6/2022 | Subramanian et al. |
| 2022/0193250 A1 | 6/2022 | Subramanian et al. |

FOREIGN PATENT DOCUMENTS

| | | |
|---|---|---|
| EP | 2736539 B1 | 8/2017 |
| EP | 2922818 B1 | 9/2018 |
| EP | 3473270 A1 | 4/2019 |
| IL | 54795 A | 10/1980 |
| WO | WO 1989/007970 A1 | 9/1989 |
| WO | WO 1991/004753 A1 | 4/1991 |
| WO | WO 2009/144481 A2 | 12/2009 |
| WO | WO 2010/048586 A1 | 4/2010 |
| WO | WO 2011/136645 A1 | 11/2011 |
| WO | WO 2013/016352 A1 | 1/2013 |
| WO | WO 2013/019623 A2 | 2/2013 |
| WO | WO2013/085550 A2 | 6/2013 |
| WO | WO 2014/065661 A1 | 5/2014 |
| WO | WO 2015/143062 A1 | 9/2015 |
| WO | WO 2015/179741 A1 | 11/2015 |
| WO | WO 2016/081670 A2 | 5/2016 |
| WO | WO 2016/187425 A1 | 11/2016 |
| WO | WO 2017/100467 A2 | 6/2017 |
| WO | WO 2017/143156 A1 | 8/2017 |
| WO | WO 2017/173408 A1 | 10/2017 |
| WO | WO 2017/192679 A1 | 11/2017 |
| WO | WO 2017/205191 A1 | 11/2017 |
| WO | WO 2017/221883 A1 | 12/2017 |
| WO | WO 2018/129384 A1 | 7/2018 |
| WO | WO 2018/226861 A1 | 12/2018 |
| WO | WO 2019/060432 A2 | 3/2019 |
| WO | WO 2019/060775 A1 | 3/2019 |
| WO | WO 2019/071028 A1 | 4/2019 |
| WO | WO 2019/136180 A2 | 7/2019 |
| WO | WO 2019/152820 A1 | 8/2019 |
| WO | WO 2019/157224 A1 | 8/2019 |
| WO | WO 2019/229658 A1 | 12/2019 |
| WO | WO 2020/028831 A1 | 2/2020 |
| WO | WO 2020/028832 A1 | 2/2020 |
| WO | WO 2020/028836 A1 | 2/2020 |
| WO | WO 2020/028840 A1 | 2/2020 |
| WO | WO 2020/028841 A1 | 2/2020 |
| WO | WO 2020/028842 A1 | 2/2020 |
| WO | WO 2020/028844 A1 | 2/2020 |
| WO | WO 2020/028857 A1 | 2/2020 |
| WO | WO 2020/028861 A1 | 2/2020 |
| WO | WO 2020/028864 A1 | 2/2020 |
| WO | WO 2020/084488 A1 | 4/2020 |
| WO | WO 2020/094670 A1 | 5/2020 |
| WO | WO 2020/132584 A1 | 6/2020 |
| WO | WO 2020/247738 A1 | 12/2020 |
| WO | WO 2020/247782 A1 | 12/2020 |
| WO | WO 2020/247818 A1 | 12/2020 |
| WO | WO 2021/076856 A1 | 4/2021 |
| WO | WO 2021/142217 A1 | 7/2021 |
| WO | WO 2021/142227 A1 | 7/2021 |
| WO | WO 2021/142234 A1 | 7/2021 |
| WO | WO 2021/142260 A1 | 7/2021 |
| WO | WO 2021/142269 A1 | 7/2021 |
| WO | WO 2021/142275 A1 | 7/2021 |
| WO | WO 2021/142307 A1 | 7/2021 |
| WO | WO 2021/142313 A1 | 7/2021 |
| WO | WO 2021/142331 A1 | 7/2021 |
| WO | WO 2021/150382 A1 | 7/2021 |
| WO | WO 2021/154476 A1 | 8/2021 |
| WO | WO 2021/154477 A1 | 8/2021 |
| WO | WO 2022/020105 A1 | 1/2022 |
| WO | WO 2022/020106 A1 | 1/2022 |
| WO | WO 2022/020107 A1 | 1/2022 |
| WO | WO 2022/020108 A1 | 1/2022 |
| WO | WO 2022/020109 A1 | 1/2022 |
| WO | WO 2022/026152 A1 | 2/2022 |
| WO | WO 2022/051332 A1 | 3/2022 |
| WO | WO 2022/051665 A1 | 3/2022 |
| WO | WO 2022/115745 A1 | 6/2022 |
| WO | WO 2022/120132 A1 | 6/2022 |
| WO | WO 2022/147207 A1 | 7/2022 |
| WO | WO 2022/147209 A1 | 7/2022 |
| WO | WO 2022/159712 A1 | 7/2022 |

OTHER PUBLICATIONS

[No Author Listed], IRDye® Peptide Labeling Application Guide. <https://licor.com/documents/nmekjs7iez6sw5p8fv7b7005chbrcog7> Published Apr. 2013. Retrieved Oct. 27, 2021. 8 pages.

[No Author Listed], Transferrin Receptor/CD71 Extracellular Domain (human, recombinant) 2021, retrieved from https://www.caymanchem.com/product/32031/transferrin-receptor-extracellular-domain-(human%2C-recombinant)#:-:text=Cayman's Transferrin Receptor%2FCD71 Extracellular,molecular weight of 103.6 kPa (Year: 2021). 3 pages.

Agard et al., A Comparative Study of Bioorthogonal Reactions with Azides. ACS Chem. Biol. 2006;1(10):644-8. Epub Oct. 20, 2006.

Agard et al., A Strain-Promoted [3 + 2] Azide—Alkyne Cycloaddition for Covalent Modification of Biomolecules in Living Systems. J. Am. Chem. Soc. Nov. 2004; 126(46):15046-7.

Anciaux et al., Transition-metal-catalyzed reactions of diazo compounds. 1. Cyclopropanation of double bonds. The Journal of Organic Chemistry. Feb. 1980;45(4):695-702.

(56) References Cited

OTHER PUBLICATIONS

Ansseau et al., Antisense Oligonucleotides Used to Target the DUX4 mRNA as Therapeutic Approaches in FacioScapuloHumeral Muscular Dystrophy (FSHD). Genes (Basel). Mar. 3, 2017;8(3):93. doi: 10.3390/genes8030093.

Ansseau et al., DUX4c is up-regulated in FSHD. It induces the MYF5 protein and human myoblast proliferation. PLoS One. Oct. 15, 2009;4(10):e7482. 11 pages.

Antony-Mayer et al., Bicyclo[6.1.0]nonine. Chemische Berichte. Nov. 1988;121(11):2013-8.

Aoki et al., Challenges for antisense oligonucleotide-based therapeutics, in particular for exon 51-skipping in Duchenne muscular dystrophy, 2011 Fourth International Conference on Modeling, Simulation and Applied Optimization, 2011, 1-6, doi: 10.1109/ICMSAO.2011.5775520.

Ast et al., Estergruppenhaltige Polyalkenylene durch Olefin-Metathese. Die Makromolekulare Chemie. May 1976;177(5):1349-55.

Barrientos et al., Metabolic Catastrophe in Mice Lacking Transferrin Receptor in Muscle. EBioMedicine. Oct. 4, 2015;2(11):1705-17. doi: 10.1016/j.ebiom.2015.09.041. eCollection Nov. 2015.

Baskin et al., Copper-free click chemistry for dynamic in vivo imaging. PNAS. Oct. 2007; 104(43):16793-7.

Bennett et al., RNA targeting therapeutics: molecular mechanisms of antisense oligonucleotides as a therapeutic platform. Annu Rev Pharmacol Toxicol. 2010;50:259-93. Epub Oct. 19, 2009.

Bien-Ly et al., Transferrin receptor (TfR) trafficking determines brain uptake of TfR antibody affinity variants. J Exp Med. Feb. 10, 2014;211(2):233-44. Epub Jan. 27, 2014.

Black, 9.13.4.1.1.3.2 Variation 2: C-Alkylation (and Arylation) by Carbenes and Free Radicals. Science of Synthesis. 2001;9:514.

Bortolanza et al., AAV6-mediated systemic shRNA delivery reverses disease in a mouse model of facioscapulohumeral muscular dystrophy. Mol Ther. Nov. 2011;19(11):2055-64. doi: 10.1038/mt.2011.153. Epub Aug. 9, 2011.

Bushel et al., Blood gene expression signatures predict exposure levels. Proc Natl Acad Sci U S A. Nov. 13, 2007;104(46):18211-6. doi: 10.1073/pnas.0706987104. Epub Nov. 2, 2007.

Campbell et al., NuRD and CAF-1-mediated silencing of the D4Z4 array is modulated by DUX4-induced MBD3L proteins. eLife. May 2018;7:e31023. 27 pages.

Candelaria et al., Antibodies Targeting the Transferrin Receptor 1 (TfR1) as Direct Anti-cancer Agents. Front Immunol. Mar. 17, 2021;12:607692.

Casi et al., Antibody-drug conjugates: basic concepts, examples and future perspectives. J Control Release. Jul. 2, 20120;161(2):422-8. doi: 10.1016/j.jconrel.2012.01.026. Epub Jan. 28, 2012.

Cenik et al., Argonaute proteins. Curr Biol. Jun. 21, 2011;21(12):R446-9.

Chamberlain et al., Validity of RNAi-based therapeutics as a treatment for FSHD as demonstrated in a mouse model of muscular dystrophy. MDA National Scientific Conference—Neuromuscular Therapeutic Strategies: Overcoming the Barriers from Microscope to Marketplace (Book of Abstracts) Mar. 13-16, 2011; p. 40. Abstract.

Chen et al., Morpholino-mediated Knockdown of DUX4 Toward Facioscapulohumeral Muscular Dystrophy Therapeutics. Mol Ther. Aug. 2016;24(8):1405-11. doi: 10.1038/mt.2016.111. Epub Jun. 3, 2016.

Chothia et al., Canonical structures for the hypervariable regions of immunoglobulins. J Mol Biol. Aug. 20, 1987;196(4):901-17. doi: 10.1016/0022-2836(87)90412-8.

Clark et al., Increased brain uptake of targeted nanoparticles by adding an acid-cleavable linkage between transferrin and the nanoparticle core. PNAS. Oct. 2015;112(40):12586-91.

Codelli et al., Second-Generation Difluorinated Cyclooctynes for Copper-Free Click Chemistry. J. Am. Chem. Soc. 2008;130(34):11486-11493. Epub Aug. 5, 2008.

Crook et al., Enrichment of early fetal-liver hemopoietic stem cells of the rat using monoclonal antibodies against the transferrin receptor, Thy-1, and MRC-OX82. Dev Immunol. 1996;4(4):235-46. doi: 10.1155/1995/85036.

Crooke et al., The Effects of 2'-O-Methoxyethyl Oligonucleotides on Renal Function in Humans. Nucleic Acid Ther. Feb. 2018;28(1):10-22. doi: 10.1089/nat.2017.0693. Epub Nov. 29, 2017.

Cuellar et al., Systematic evaluation of antibody-mediated siRNA delivery using an industrial platform of THIOMAB-siRNA conjugates. Nucleic Acids Res. Jan. 2015;43(2):1189-203. Epub Dec. 30, 2014.

Curtius, Ueber die Einwirkung von salpetriger Sätire auf salzsauren Glycocolläther. Berichte der deutschen chemischen Gesellschaft. Jul.-Dec. 1883;16(2):2230-1.

Daxinger et al., Genetic and epigenetic contributors to FSHD. Current Opinion in Genetics & Development. Aug. 2015;33:56-61. Author manuscript. 11 pages.

Debets et al., Bioorthogonal labelling of biomolecules: new functional handles and ligation methods. Org Biomol Chem. Oct. 14, 2013;11(38):6439-55. Epub Aug. 23, 2013.

Demonceau et al., Novel Ruthenium-Based Catalyst Systems for the Ring-Opening Metathesis Polymerization of Low-Strain Cyclic Olefins. Macromolecules. 1997;30(11):3127-36. Epub Jun. 2, 1997.

Dixit et al., DUX4, a candidate gene of facioscapulohumeral muscular dystrophy, encodes a transcriptional activator of PITX1. Proc Natl Acad Sci U S A. Nov. 13, 2007;104(46):18157-62. doi: 10.1073/pnas.0708659104. Epub Nov. 5, 2007.

Dommerholt et al., Readily accessible bicyclononynes for bioorthogonal labeling and three-dimensional imaging of living cells. Angew Chem Int Ed Engl. Dec. 3, 2010;49(49):9422-5.

Dommerholt et al., Strain-Promoted 1,3-Dipolar Cycloaddition of Cycloalkynes and Organic Azides. Top Curr Chem (Cham). Apr. 2016;374(2):16. doi: 10.1007/s41061-016-0016-4. Epub Mar. 22, 2016.

Efferth et al., Enhancement of cytotoxicity of artemisinins toward cancer cells by ferrous iron. Free Radic Biol Med. Oct. 1, 2004;37(7):998-1009. doi: 10.1016/i.freeradbiomed.2004.06.023.

Frazier, Antisense oligonucleotide therapies: the promise and the challenges from a toxicologic pathologist's perspective. Toxicol Pathol. Jan. 2015;43(1):78-89. doi: 10.1177/0192623314551840. Epub Nov. 9, 2014.

Geary et al., Pharmacokinetics, biodistribution and cell uptake of antisense oligonucleotides. Adv Drug Deliv Rev. Jun. 29, 2015;87:46-51. doi: 10.1016/j.addr.2015.01.008. Epub Feb. 7, 2015.

Geng et al., DUX4 activates germline genes, retroelements, and immune mediators: implications for facioscapulohumeral dystrophy. Dev Cell. Jan. 17, 2012;22(1):38-51. doi: 10.1016/j.devcel.2011.11.013. Epub Dec. 29, 2011.

Girones et al. Comparison of the kinetics of cycling of the transferrin receptor in the presence or absence of bound diferric transferrin. Biochem J. Nov. 15, 1989;264(1):35-46.

Gong et al., Simple Method To Prepare Oligonucleotide-Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.

Hein et al., Click chemistry, a powerful tool for pharmaceutical sciences. Pharm Res. Oct. 2008;25(10):2216-30. doi: 10.1007/s11095-008-9616-1. Epub May 29, 2008.

Helguera et al. An antibody recognizing the apical domain of human transferrin receptor 1 efficiently inhibits the entry of all new world hemorrhagic Fever arenaviruses. J Virol. Apr. 2012;86(7):4024-8. doi: 10.1128/JVI.06397-11. Epub Jan. 25, 2012.

Iwaki et al., Preparation of Chiral Stationary Phase via Activated Carbamate Intermediate for Liquid Chromatographic Optical Resolution. Chromatographia. Oct. 1987;23:727-30.

Jain et al., Current ADC Linker Chemistry. Pharm Res. Nov. 2015;32(11):3526-40. Epub Mar. 11, 2015.

Jearawiriyapaisarn et al., Sustained Dystrophin Expression Induced by Peptide-conjugated Morpholino Oligomers in the Muscles of mdx Mice. Mol Ther. Sep. 2008;16(9):1624-9. doi: 10.1038/mt.2008.120. Epub Jun. 10, 2008.

(56) References Cited

OTHER PUBLICATIONS

Juliano, The delivery of therapeutic oligonucleotides. Nucleic Acids Res. Aug. 19, 2016;44(14):6518-48. doi: 10.1093/nar/gkw236. Epub Apr. 15, 2016.

Kim et al., Strategies for silencing human disease using RNA interference. Nat Rev Genet. Mar. 2007;8(3):173-84. doi: 10.1038/nrg2006.

Kline et al., Methods to Make Homogenous Antibody Drug Conjugates. Pharm Res. Nov. 2015;32(11):3480-93. Epub Dec. 16, 2014.

Kumar et al., Antisense RNA: Function and Fate of Duplex RNA in Cells of Higher Eukaryotes. Microbiol Mol Biol Rev. Dec. 1998; 62(4): 1415-34.

Kuran et al., Investigations on the Catalytic Systems Diethylzinc/Di- and Trihydroxybenzenes in the Copolymerization of Carbon Dioxide with Propylene Oxide. Makromol. Chem. 1976;177:1283-92.

Lai et al., Mechanism of action and spectrum of cell lines sensitive to a doxorubicin-transferrin conjugate. Cancer Chemother Pharmacol. 1998;41(2):155-60. doi: 10.1007/s002800050722.

Lam et al., siRNA Versus miRNA as Therapeutics for Gene Silencing. Mol Ther Nucleic Acids. Sep. 15, 2015;4(9):e252. 20 pages.

Lawrence et al., Crystal structure of the ectodomain of human transferrin receptor. Science. Oct. 22, 1999;286(5440):779-82. doi: 10.1126/science.286.5440.779.

Lemmers et al., A unifying genetic model for facioscapulohumeral muscular dystrophy. Science. Sep. 24, 2010;329(5999):1650-3. Epub Aug. 19, 2010.

Lemmers et al., Facioscapulohumeral muscular dystrophy is uniquely associated with one of the two variants of the 4q subtelomere. Nat Genet. Oct. 2002;32(2):235-6.

Lennox et al., Cellular localization of long non-coding RNAs affects silencing by RNAi more than by antisense oligonucleotides. Nucleic Acids Res. Jan. 29, 2016;44(2):863-77. doi: 10.1093/nar/gkv1206. Epub Nov. 17, 2015.

Lesley et al., Selection of cell lines resistant to anti-transferrin receptor antibody: evidence for a mutation in transferrin receptor. Mol Cell Biol. Sep. 1984;4(9):1675-81. doi: 10.1128/mcb.4.9.1675-1681.1984.

Liang et al., Targeted delivery of plasmid DNA to myogenic cells via transferrin-conjugated peptide nucleic acid. Mol Ther. Mar. 2000;1(3):236-43. doi: 10.1006/mthe.2000.0043.

Liu, Exploring cell type-specific internalizing antibodies for targeted delivery of siRNA. Brief Funct Genomic Proteomic. Jun. 2007;6(2):112-9. doi: 10.1093/bfgp/elm015. Epub Jul. 31, 2007.

Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.

Meeuwissen et al., Cofactor regeneration in polymersome nanoreactors: Enzymatically catalysed Baeyer-Villiger reactions. Journal of Materials Chemistry. Dec. 2011;21(47):18923-6.

Mojsov et al., A Quantitative Evaluation of Methods for Coupling Asparagine. The Journal of Organic Chemistry. Feb. 1980;45(4):555-60.

Ohrt et al., In situ fluorescence analysis demonstrates active siRNA exclusion from the nucleus by Exportin 5. Nucleic Acids Res. Mar. 6, 2006;34(5):1369-80. doi: 10.1093/nar/gkl001. Print 2006.

Padlan et al., A possible procedure for reducing the immunogenicity of antibody variable domains while preserving their ligand-binding properties. Molecular Immunology. Apr.-May 1991;28(4-5):489-98.

Qian et al., Targeted drug delivery via the transferrin receptor-mediated endocytosis pathway. Pharmacol Rev. Dec. 2002;54(4):561-87. doi: 10.1124/pr.54.4.561.

Roberts et al., Advances in oligonucleotide drug delivery. Nat Rev Drug Discov. Oct. 2020;19(10):673-694. doi: 10.1038/s41573-020-0075-7. Epub Aug. 11, 2020.

Roberts et al., The Halogenation of Ethylenes. J. Am. Chem. Soc. May 1937;59(5):947-8.

Schnyder et al., Targeting of skeletal muscle in vitro using biotinylated immunoliposomes. Biochem J. Jan. 1, 2004;377(Pt 1):61-7. doi: 10.1042/BJ20031034.

Setten et al., The current state and future directions of RNAi-based therapeutics. Nat Rev Drug Discov. Jun. 2019;18(6):421-446. doi: 10.1038/s41573-019-0017-4.

Singh et al., Catalytic Enantioselective Cyclopropanation of Olefins Using Carbenoid Chemistry. Synthesis. Feb. 1997;137-49.

Snider et al., Facioscapulohumeral dystrophy: incomplete suppression of a retrotransposed gene. PLoS Genet. Oct. 28, 2010;6(10):e1001181. 14 pages.

Snider et al., RNA transcripts, miRNA-sized fragments and proteins produced from D4Z4 units: new candidates for the pathophysiology of facioscapulohumeral dystrophy. Hum Mol Genet. Jul. 1, 2009;18(13):2414-30. Epub Apr. 9, 2009.

Stocki et al., Blood-brain barrier transport using a high affinity, brain-selective VNAR antibody targeting transferrin receptor 1. Faseb J. Feb. 2021;35(2):e21172. doi: 10.1096/fj.202001787R. Epub Nov. 25, 2020.

Sugo et al., Development of antibody-siRNA conjugate targeted to cardiac and skeletal muscles. J Control Release. Sep. 10, 2016;237:1-13. doi: 10.1016/j.jconrel.2016.06.036. Epub Jun. 29, 2016.

Summerton et al..Morpholino antisense oligomers: design, preparation, and properties. Antisense Nucleic Acid Drug Dev. Jun. 1997;7(3):187-95.

Tron et al., Click chemistry reactions in medicinal chemistry: applications of the 1,3-dipolar cycloaddition between azides and alkynes. Med Res Rev. Mar. 2008;28(2):278-308.

Trowbridge et al., Anti-transferrin receptor monoclonal antibody and toxin-antibody conjugates affect growth of human tumour cells. Nature. Nov. 12, 1981;294(5837):171-3. doi: 10.1038/294171a0.

Van Der Maarel et al., Facioscapulohumeral muscular dystrophy and DUX4: breaking the silence. Trends Mol Med. May 2011;17(5):252-8. Epub Feb. 1, 2011.

Van Deutekom, Abstract—The Development of RNA-Modulating Therapies. RNA & Oligonucleotide Therapeutics. Cold Spring Harbor Laboratory. Cold Spring Harbor, NY. Apr. 7-10, 2010:3. 19 pages total.

Vanderplanck et al., Abstract Keynote 5—Suppression of DUX4 or DUX4C expression by antisense strategies in a therapeutic approach for FSHD. 7th Australian Gene Therapy Society Meeting. The Journal of Gene Medicine. May 2011;13:414.

Vanderplanck et al., Suppression of DUX4 or DUX4c protein expression by antisense strategies in a therapeutic approach for FSHD. MDA National Scientific Conference—Neuromuscular Therapeutic Strategies: Overcoming the Barriers from Microscope to Marketplace (Book of Abstracts) Mar. 13-16, 2011; p. 8. Abstract.

Wagner et al., Transferrin-polycation conjugates as carriers for DNA uptake into cells. Proc Natl Acad Sci U S A. May 1990;87(9):3410-4. doi: 10.1073/pnas.87.9.3410.

Walker et al., Improved cellular delivery of antisense oligonucleotides using transferrin receptor antibody-oligonucleotide conjugates. Pharm Res. Oct. 1995;12(10):1548-53. doi: 10.1023/a:1016260110049.

Wallace et al., Abstract 387—Developing RNAi Therapy for FSHD. Molecular Therapy. May 2009;17(1):S151.

Walles et al., ADME and Safety Aspects of Non-cleavable Linkers in Drug Discovery and Development. Curr Top Med Chem. 2017;17(32):3463-3475. doi: 10.2174/1568026618666180118153502.

Wilton et al., Exon skipping and Duchenne muscular dystrophy: hope, hype and how feasible? Neurol India. Jul.-Sep. 2008;56(3):254-62. doi: 10.4103/0028-3886.43443.

Xia et al., Intravenous siRNA of brain cancer with receptor targeting and avidin-biotin technology. Pharm Res. Dec. 2007;24(12):2309-16. doi: 10.1007/s11095-007-9460-8. Epub Oct. 11, 2007.

Yao et al., DUX4-induced gene expression is the major molecular signature in FSHD skeletal muscle. Hum Mol Genet. Oct. 15, 2014; 23(20): 5342-5352. Epub May 26, 2014.

Pradeepkumar, Chemically modified oligonucleotides: synthesis, physicochemical and biochemical properties of their duplexes with DNA and RNA. Comprehensive Summaries of Uppsala Dissertations from the Faculty of Science and Technology. 2004; 973: 56 pages.

(56) References Cited

OTHER PUBLICATIONS

Shen et al., Chemistry, mechanism and clinical status of antisense oligonucleotides and duplex RNAs. Nucleic Acids Res. Feb. 28, 2018;46(4):1584-1600.
Tawil et al., Facioscapulohumeral dystrophy: the path to consensus on pathophysiology. Skelet Muscle. Jun. 10, 2014;4:12.
Wallace et al., RNA interference inhibits DUX4-induced muscle toxicity in vivo: implications for a targeted FSHD therapy. Mol Ther. Jul. 2012;20(7):1417-23. doi: 10.1038/mt.2012.68. Epub Apr. 17, 2012.

\* cited by examiner

SEQUENCE LISTING

```
<160> NUMBER OF SEQ ID NOS: 52

<210> SEQ ID NO 1
<211> LENGTH: 760
<212> TYPE: PRT
<213> ORGANISM: Homo sapiens

<400> SEQUENCE: 1

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Val Asp Glu Glu Glu Asn Ala
            35                  40                  45

Asp Asn Asn Thr Lys Ala Asn Val Thr Lys Pro Lys Arg Cys Ser Gly
        50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160
```

-continued

```
Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575
```

```
Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 2
<211> LENGTH: 760
<212> TYPE: PRT
<213> ORGANISM: Macaca mulatta

<400> SEQUENCE: 2

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Gly Val Asp Glu Glu Asn Thr
            35                  40                  45

Asp Asn Asn Thr Lys Pro Asn Gly Thr Lys Pro Lys Arg Cys Gly Gly
    50                  55                  60

Asn Ile Cys Tyr Gly Thr Ile Ala Val Ile Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Ala Arg Glu Glu Pro
            100                 105                 110

Glu Glu Asp Phe Pro Ala Ala Pro Arg Leu Tyr Trp Asp Asp Leu Lys
        115                 120                 125

Arg Lys Leu Ser Glu Lys Leu Asp Thr Thr Asp Phe Thr Ser Thr Ile
    130                 135                 140

Lys Leu Leu Asn Glu Asn Leu Tyr Val Pro Arg Glu Ala Gly Ser Gln
145                 150                 155                 160

Lys Asp Glu Asn Leu Ala Leu Tyr Ile Glu Asn Gln Phe Arg Glu Phe
                165                 170                 175

Lys Leu Ser Lys Val Trp Arg Asp Gln His Phe Val Lys Ile Gln Val
            180                 185                 190
```

```
Lys Asp Ser Ala Gln Asn Ser Val Ile Ile Val Asp Lys Asn Gly Gly
        195                 200                 205
Leu Val Tyr Leu Val Glu Asn Pro Gly Gly Tyr Val Ala Tyr Ser Lys
210             215                 220
Ala Ala Thr Val Thr Gly Lys Leu Val His Ala Asn Phe Gly Thr Lys
225                 230                 235                 240
Lys Asp Phe Glu Asp Leu Asp Ser Pro Val Asn Gly Ser Ile Val Ile
            245                 250                 255
Val Arg Ala Gly Lys Ile Thr Phe Ala Glu Lys Val Ala Asn Ala Glu
                260                 265                 270
Ser Leu Asn Ala Ile Gly Val Leu Ile Tyr Met Asp Gln Thr Lys Phe
        275                 280                 285
Pro Ile Val Lys Ala Asp Leu Ser Phe Phe Gly His Ala His Leu Gly
        290                 295                 300
Thr Gly Asp Pro Tyr Thr Pro Gly Phe Pro Ser Phe Asn His Thr Gln
305                 310                 315                 320
Phe Pro Pro Ser Gln Ser Ser Gly Leu Pro Asn Ile Pro Val Gln Thr
                325                 330                 335
Ile Ser Arg Ala Ala Ala Glu Lys Leu Phe Gly Asn Met Glu Gly Asp
                340                 345                 350
Cys Pro Ser Asp Trp Lys Thr Asp Ser Thr Cys Lys Met Val Thr Ser
        355                 360                 365
Glu Asn Lys Ser Val Lys Leu Thr Val Ser Asn Val Leu Lys Glu Thr
        370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                405                 410                 415
Ala Lys Ser Ser Val Gly Thr Ala Leu Leu Leu Lys Leu Ala Gln Met
                420                 425                 430
Phe Ser Asp Met Val Leu Lys Asp Gly Phe Gln Pro Ser Arg Ser Ile
        435                 440                 445
Ile Phe Ala Ser Trp Ser Ala Gly Asp Phe Gly Ser Val Gly Ala Thr
        450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
            485                 490                 495
Ser Ala Ser Pro Leu Leu Tyr Thr Leu Ile Glu Lys Thr Met Gln Asp
                500                 505                 510
Val Lys His Pro Val Thr Gly Arg Ser Leu Tyr Gln Asp Ser Asn Trp
        515                 520                 525
Ala Ser Lys Val Glu Lys Leu Thr Leu Asp Asn Ala Ala Phe Pro Phe
        530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
                565                 570                 575
Val Glu Arg Ile Pro Glu Leu Asn Lys Val Ala Arg Ala Ala Ala Glu
            580                 585                 590
Val Ala Gly Gln Phe Val Ile Lys Leu Thr His Asp Thr Glu Leu Asn
        595                 600                 605
```

-continued

Leu Asp Tyr Glu Arg Tyr Asn Ser Gln Leu Leu Phe Leu Arg Asp
610                 615                 620

Leu Asn Gln Tyr Arg Ala Asp Val Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Arg Asn Ala Glu Lys Arg Asp Lys Phe Val Met Lys
            660                 665                 670

Lys Leu Asn Asp Arg Val Met Arg Val Glu Tyr Tyr Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Ser Ala Leu Leu Glu Ser Leu Lys Leu Arg Arg
705                 710                 715                 720

Gln Asn Asn Ser Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 3
<211> LENGTH: 760
<212> TYPE: PRT
<213> ORGANISM: Macaca fascicularis

<400> SEQUENCE: 3

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Gly Val Asp Glu Glu Asn Thr
            35                  40                  45

Asp Asn Asn Thr Lys Ala Asn Gly Thr Lys Pro Lys Arg Cys Gly Gly
    50                  55                  60

Asn Ile Cys Tyr Gly Thr Ile Ala Val Ile Ile Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Ala Arg Glu Glu Pro
            100                 105                 110

Glu Glu Asp Phe Pro Ala Ala Pro Arg Leu Tyr Trp Asp Asp Leu Lys
        115                 120                 125

Arg Lys Leu Ser Glu Lys Leu Asp Thr Thr Asp Phe Thr Ser Thr Ile
130                 135                 140

Lys Leu Leu Asn Glu Asn Leu Tyr Val Pro Arg Glu Ala Gly Ser Gln
145                 150                 155                 160

Lys Asp Glu Asn Leu Ala Leu Tyr Ile Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Gly
        195                 200                 205

Leu Val Tyr Leu Val Glu Asn Pro Gly Gly Tyr Val Ala Tyr Ser Lys
    210                 215                 220

-continued

```
Ala Ala Thr Val Thr Gly Lys Leu Val His Ala Asn Phe Gly Thr Lys
225                 230                 235                 240

Lys Asp Phe Glu Asp Leu Asp Ser Pro Val Asn Gly Ser Ile Val Ile
            245                 250                 255

Val Arg Ala Gly Lys Ile Thr Phe Ala Glu Lys Val Ala Asn Ala Glu
        260                 265                 270

Ser Leu Asn Ala Ile Gly Val Leu Ile Tyr Met Asp Gln Thr Lys Phe
    275                 280                 285

Pro Ile Val Lys Ala Asp Leu Ser Phe Phe Gly His Ala His Leu Gly
290                 295                 300

Thr Gly Asp Pro Tyr Thr Pro Gly Phe Pro Ser Phe Asn His Thr Gln
305                 310                 315                 320

Phe Pro Pro Ser Gln Ser Ser Gly Leu Pro Asn Ile Pro Val Gln Thr
            325                 330                 335

Ile Ser Arg Ala Ala Ala Glu Lys Leu Phe Gly Asn Met Glu Gly Asp
        340                 345                 350

Cys Pro Ser Asp Trp Lys Thr Asp Ser Thr Cys Lys Met Val Thr Ser
    355                 360                 365

Glu Asn Lys Ser Val Lys Leu Thr Val Ser Asn Val Leu Lys Glu Thr
370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
            405                 410                 415

Ala Lys Ser Ser Val Gly Thr Ala Leu Leu Lys Leu Ala Gln Met
        420                 425                 430

Phe Ser Asp Met Val Leu Lys Asp Gly Phe Gln Pro Ser Arg Ser Ile
    435                 440                 445

Ile Phe Ala Ser Trp Ser Ala Gly Asp Phe Gly Ser Val Gly Ala Thr
450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
            485                 490                 495

Ser Ala Ser Pro Leu Leu Tyr Thr Leu Ile Glu Lys Thr Met Gln Asp
        500                 505                 510

Val Lys His Pro Val Thr Gly Arg Ser Leu Tyr Gln Asp Ser Asn Trp
    515                 520                 525

Ala Ser Lys Val Glu Lys Leu Thr Leu Asp Asn Ala Ala Phe Pro Phe
530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
            565                 570                 575

Val Glu Arg Ile Pro Glu Leu Asn Lys Val Ala Arg Ala Ala Ala Glu
        580                 585                 590

Val Ala Gly Gln Phe Val Ile Lys Leu Thr His Asp Thr Glu Leu Asn
    595                 600                 605

Leu Asp Tyr Glu Arg Tyr Asn Ser Gln Leu Leu Leu Phe Leu Arg Asp
610                 615                 620

Leu Asn Gln Tyr Arg Ala Asp Val Lys Glu Met Gly Leu Ser Leu Gln
625                 630                 635                 640
```

```
Trp Leu Tyr Ser Ala Arg Gly Asp Phe Phe Arg Ala Thr Ser Arg Leu
                645                 650                 655

Thr Thr Asp Phe Arg Asn Ala Glu Lys Arg Asp Lys Phe Val Met Lys
            660                 665                 670

Lys Leu Asn Asp Arg Val Met Arg Val Glu Tyr Tyr Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Ser Ala Leu Leu Glu Ser Leu Lys Leu Arg Arg
705                 710                 715                 720

Gln Asn Asn Ser Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 4
<211> LENGTH: 763
<212> TYPE: PRT
<213> ORGANISM: Mus musculus

<400> SEQUENCE: 4

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Ala Asp Glu Glu Asn Ala
            35                  40                  45

Asp Asn Asn Met Lys Ala Ser Val Arg Lys Pro Lys Arg Phe Asn Gly
        50                  55                  60

Arg Leu Cys Phe Ala Ala Ile Ala Leu Val Ile Phe Phe Leu Ile Gly
65                  70                  75                  80

Phe Met Ser Gly Tyr Leu Gly Tyr Cys Lys Arg Val Glu Gln Lys Glu
                85                  90                  95

Glu Cys Val Lys Leu Ala Glu Thr Glu Glu Thr Asp Lys Ser Glu Thr
            100                 105                 110

Met Glu Thr Glu Asp Val Pro Thr Ser Ser Arg Leu Tyr Trp Ala Asp
        115                 120                 125

Leu Lys Thr Leu Leu Ser Glu Lys Leu Asn Ser Ile Glu Phe Ala Asp
    130                 135                 140

Thr Ile Lys Gln Leu Ser Gln Asn Thr Tyr Thr Pro Arg Glu Ala Gly
145                 150                 155                 160

Ser Gln Lys Asp Glu Ser Leu Ala Tyr Tyr Ile Glu Asn Gln Phe His
                165                 170                 175

Glu Phe Lys Phe Ser Lys Val Trp Arg Asp Glu His Tyr Val Lys Ile
            180                 185                 190

Gln Val Lys Ser Ser Ile Gly Gln Asn Met Val Thr Ile Val Gln Ser
        195                 200                 205

Asn Gly Asn Leu Asp Pro Val Glu Ser Pro Glu Gly Tyr Val Ala Phe
    210                 215                 220

Ser Lys Pro Thr Glu Val Ser Gly Lys Leu Val His Ala Asn Phe Gly
225                 230                 235                 240

Thr Lys Lys Asp Phe Glu Glu Leu Ser Tyr Ser Val Asn Gly Ser Leu
                245                 250                 255
```

```
Val Ile Val Arg Ala Gly Glu Ile Thr Phe Ala Glu Lys Val Ala Asn
            260                 265                 270

Ala Gln Ser Phe Asn Ala Ile Gly Val Leu Ile Tyr Met Asp Lys Asn
        275                 280                 285

Lys Phe Pro Val Val Glu Ala Asp Leu Ala Leu Phe Gly His Ala His
    290                 295                 300

Leu Gly Thr Gly Asp Pro Tyr Thr Pro Gly Phe Pro Ser Phe Asn His
305                 310                 315                 320

Thr Gln Phe Pro Pro Ser Gln Ser Ser Gly Leu Pro Asn Ile Pro Val
                325                 330                 335

Gln Thr Ile Ser Arg Ala Ala Glu Lys Leu Phe Gly Lys Met Glu
            340                 345                 350

Gly Ser Cys Pro Ala Arg Trp Asn Ile Asp Ser Ser Cys Lys Leu Glu
        355                 360                 365

Leu Ser Gln Asn Gln Asn Val Lys Leu Ile Val Lys Asn Val Leu Lys
    370                 375                 380

Glu Arg Arg Ile Leu Asn Ile Phe Gly Val Ile Lys Gly Tyr Glu Glu
385                 390                 395                 400

Pro Asp Arg Tyr Val Val Gly Ala Gln Arg Asp Ala Leu Gly Ala
                405                 410                 415

Gly Val Ala Ala Lys Ser Ser Val Gly Thr Gly Leu Leu Lys Leu
            420                 425                 430

Ala Gln Val Phe Ser Asp Met Ile Ser Lys Asp Gly Phe Arg Pro Ser
        435                 440                 445

Arg Ser Ile Ile Phe Ala Ser Trp Thr Ala Gly Asp Phe Gly Ala Val
    450                 455                 460

Gly Ala Thr Glu Trp Leu Glu Gly Tyr Leu Ser Ser Leu His Leu Lys
465                 470                 475                 480

Ala Phe Thr Tyr Ile Asn Leu Asp Lys Val Val Leu Gly Thr Ser Asn
                485                 490                 495

Phe Lys Val Ser Ala Ser Pro Leu Leu Tyr Thr Leu Met Gly Lys Ile
            500                 505                 510

Met Gln Asp Val Lys His Pro Val Asp Gly Lys Ser Leu Tyr Arg Asp
        515                 520                 525

Ser Asn Trp Ile Ser Lys Val Glu Lys Leu Ser Phe Asp Asn Ala Ala
    530                 535                 540

Tyr Pro Phe Leu Ala Tyr Ser Gly Ile Pro Ala Val Ser Phe Cys Phe
545                 550                 555                 560

Cys Glu Asp Ala Asp Tyr Pro Tyr Leu Gly Thr Arg Leu Asp Thr Tyr
                565                 570                 575

Glu Ala Leu Thr Gln Lys Val Pro Gln Leu Asn Gln Met Val Arg Thr
            580                 585                 590

Ala Ala Glu Val Ala Gly Gln Leu Ile Ile Lys Leu Thr His Asp Val
        595                 600                 605

Glu Leu Asn Leu Asp Tyr Glu Met Tyr Asn Ser Lys Leu Leu Ser Phe
    610                 615                 620

Met Lys Asp Leu Asn Gln Phe Lys Thr Asp Ile Arg Asp Met Gly Leu
625                 630                 635                 640

Ser Leu Gln Trp Leu Tyr Ser Ala Arg Gly Asp Tyr Phe Arg Ala Thr
                645                 650                 655

Ser Arg Leu Thr Thr Asp Phe His Asn Ala Glu Lys Thr Asn Arg Phe
            660                 665                 670
```

```
Val Met Arg Glu Ile Asn Asp Arg Ile Met Lys Val Glu Tyr His Phe
            675                 680                 685

Leu Ser Pro Tyr Val Ser Pro Arg Glu Ser Pro Phe Arg His Ile Phe
        690                 695                 700

Trp Gly Ser Gly Ser His Thr Leu Ser Ala Leu Val Glu Asn Leu Lys
705                 710                 715                 720

Leu Arg Gln Lys Asn Ile Thr Ala Phe Asn Glu Thr Leu Phe Arg Asn
                725                 730                 735

Gln Leu Ala Leu Ala Thr Trp Thr Ile Gln Gly Val Ala Asn Ala Leu
                740                 745                 750

Ser Gly Asp Ile Trp Asn Ile Asp Asn Glu Phe
        755                 760

<210> SEQ ID NO 5
<211> LENGTH: 197
<212> TYPE: PRT
<213> ORGANISM: Artificial Sequence
<220> FEATURE:
<223> OTHER INFORMATION: Synthetic polypeptide

<400> SEQUENCE: 5

Phe Val Lys Ile Gln Val Lys Asp Ser Ala Gln Asn Ser Val Ile Ile
1               5                   10                  15

Val Asp Lys Asn Gly Arg Leu Val Tyr Leu Val Glu Asn Pro Gly Gly
            20                  25                  30

Tyr Val Ala Tyr Ser Lys Ala Ala Thr Val Thr Gly Lys Leu Val His
        35                  40                  45

Ala Asn Phe Gly Thr Lys Lys Asp Phe Glu Asp Leu Tyr Thr Pro Val
    50                  55                  60

Asn Gly Ser Ile Val Ile Val Arg Ala Gly Lys Ile Thr Phe Ala Glu
65                  70                  75                  80

Lys Val Ala Asn Ala Glu Ser Leu Asn Ala Ile Gly Val Leu Ile Tyr
                85                  90                  95

Met Asp Gln Thr Lys Phe Pro Ile Val Asn Ala Glu Leu Ser Phe Phe
            100                 105                 110

Gly His Ala His Leu Gly Thr Gly Asp Pro Tyr Thr Pro Gly Phe Pro
        115                 120                 125

Ser Phe Asn His Thr Gln Phe Pro Pro Ser Arg Ser Ser Gly Leu Pro
    130                 135                 140

Asn Ile Pro Val Gln Thr Ile Ser Arg Ala Ala Ala Glu Lys Leu Phe
145                 150                 155                 160

Gly Asn Met Glu Gly Asp Cys Pro Ser Asp Trp Lys Thr Asp Ser Thr
                165                 170                 175

Cys Arg Met Val Thr Ser Glu Ser Lys Asn Val Lys Leu Thr Val Ser
            180                 185                 190

Asn Val Leu Lys Glu
        195

<210> SEQ ID NO 6
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 6

Ala Ser Ser Leu Asn Ile Ala
1               5
```

```
<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 7

Ser Lys Thr Phe Asn Thr His Pro Gln Ser Thr Pro
1               5                  10

<210> SEQ ID NO 8
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 8

Thr Ala Arg Gly Glu His Lys Glu Glu Glu Leu Ile
1               5                  10

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 9

Cys Gln Ala Gln Gly Gln Leu Val Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 10

Cys Ser Glu Arg Ser Met Asn Phe Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 11

Cys Pro Lys Thr Arg Arg Val Pro Cys
1               5

<210> SEQ ID NO 12
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 12

Trp Leu Ser Glu Ala Gly Pro Val Val Thr Val Arg Ala Leu Arg Gly
1               5                  10                  15
```

Thr Gly Ser Trp
          20

<210> SEQ ID NO 13
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 13

Cys Met Gln His Ser Met Arg Val Cys
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 14

Asp Asp Thr Arg His Trp Gly
1               5

<210> SEQ ID NO 15
<211> LENGTH: 1275
<212> TYPE: DNA
<213> ORGANISM: Homo sapiens

<400> SEQUENCE: 15

```
atggccctcc cgacaccctc ggacagcacc ctccccgcgg aagcccgggg acgaggacgg      60
cgacggagac tcgtttggac cccgagccaa agcgaggccc tgcgagcctg ctttgagcgg     120
aacccgtacc cgggcatcgc caccagagaa cggctggccc aggccatcgg cattccggag     180
cccagggtcc agatttggtt tcagaatgag aggtcacgcc agctgaggca gcaccggcgg     240
gaatctcggc cctggcccgg gagacgcggc ccgccagaag gccggcgaaa gcggaccgcc     300
gtcaccggat cccagaccgc cctgctcctc cgagcctttg agaaggatcg ctttccaggc     360
atcgccgccc gggaggagct ggccagagag acgggcctcc cggagtccag gattcagatc     420
tggtttcaga atcgaagggc caggcacccg ggacagggtg cagggcgcc cgcgcaggca     480 ggcggcctgt gcagcgcggc ccccggcggg ggtcaccctg ctccctcgtg ggtcgccttc     540
gcccacaccg gcgcgtgggg aacggggctt cccgcacccc acgtgccctg cgcgcctggg     600
gctctcccac aggggctttt cgtgagccag gcagcgaggg ccgcccccgc gctgcagccc     660
agccaggccg cgccggcaga ggggatctcc caacctgccc cggcgcgcgg ggatttcgcc     720
tacgccgccc cggctcctcc ggacggggcg ctctcccacc ctcaggctcc tcggtggcct     780
ccgcacccgg gcaaaagccg ggaggaccgg gacccgcagc gcgacggcct gccgggcccc     840
tgcgcggtgg cacagcctgg gcccgctcaa gcggggccgc agggcaagg ggtgcttgcg     900 ccacccacgt cccaggggag tccgtggtgg ggctggggcc ggggtcccca ggtcgccggg     960
gcggcgtggg aaccccaagc cggggcagct ccacctcccc agcccgcgcc ccggacgcc    1020 tccgcctccg cgcggcaggg gcagatgcaa ggcatcccgg cgccctccca ggcgctccag    1080
gagccggcgc cctggtctgc actcccctgc ggcctgctgc tgatgagct cctggcgagc    1140 ccggagtttc tgcagcaggc gcaacctctc ctagaaacgg aggccccggg ggagctggag    1200
gcctcggaag aggccgcctc gctggaagca cccctcagcg aggaagaata ccgggctctg    1260
```
ctggaggagc tttag            1275

<210> SEQ ID NO 16
<211> LENGTH: 2024
<212> TYPE: DNA
<213> ORGANISM: Mus musculus

<400> SEQUENCE: 16

```
atggcagaag ctggcagccc tgttggtggc agtggtgtgg cacgggaatc ccggcggcgc      60
aggaagacgg tttggcaggc ctggcaagag caggccctgc tatcaacttt caagaagaag     120
agatacctga gcttcaagga gaggaaggag ctggccaagc gaatgggggt ctcagattgc     180
cgcatccgcg tgtggtttca gaaccgcagg aatcgcagtg gagaggaggg gcatgcctca     240
aagaggtcca tcagaggctc caggcggcta gcctcgccac agctccagga gagcttgga     300
tccaggccac agggtagagg catgcgctca tctggcagaa ggcctcgcac tcgactcacc     360
tcgctacagc tcaggatcct agggcaagcc tttgagagga acccacgacc aggctttgct     420
accagggagg agctggcgcg tgacacaggg ttgcccgagg acacgatcca catatggttt     480
caaaaccgaa gagctcggcg gcgccacagg aggggcaggc ccacagctca agatcaagac     540
ttgctggcgt cacaagggtc ggatgggggcc cctgcaggtc cggaaggcag agagcgtgaa     600
ggtgcccagg agaacttgtt gccacaggaa gaagcaggaa gtacgggcat ggatacctcg     660
agccctagcg acttgccctc cttctgcgga gagtcccagc cttccaagt ggcacagccc     720
cgtggagcag gccaacaaga ggcccccact cgagcaggca acgcaggctc tctggaaccc     780
ctccttgatc agctgctgga tgaagtccaa gtagaagagc ctgctccagc ccctctgaat     840
ttggatggag accctggtgg cagggtgcat gaaggttccc aggagagctt tggccacag      900
gaagaagcag gaagtacagg catggatact tctagcccca cgactcaaa ctccttctgc     960
agagagtccc agccttccca gtggcacag ccctgtggag cgggccaaga gatgcccgc     1020
actcaagcag acagcacagg ccctctggaa ctcctcctcc ttgatcaact gctggacgaa    1080
gtccaaaagg aagagcatgt gccagtccca ctggattggg gtagaaatcc tggcagcagg    1140
gagcatgaag gttcccagga cagcttactg ccctggagg aagcagtaaa ttcgggcatg    1200
gatacctcga tccctagcat ctggccaacc ttctgcagag aatcccagcc tccccaagtg    1260
gcacagccct ctggaccagg ccaagcacag gcccccactc aaggtgggaa cacgacccc    1320
ctggagctct tcctctatca actgttggat gaagtccaag tagaagagca tgctccagcc    1380
cctctgaatt gggatgtaga tcctggtggc agggtgcatg aaggttcgtg ggagagcttt    1440
tggccacagg aagaagcagg aagtacaggc ctggatactt caagcccag cgactcaaac    1500
tccttcttca gagagtccaa gccttccaa gtggcacagc gccgtggagc gggccaagaa    1560
gatgcccgca ctcaagcaga cagcacaggc cctctggaac tcctcctctt tgatcaactg    1620
ctggacgaag tccaaaagga agagcatgtg ccagccccac tggattgggg tagaaatcct    1680
ggcagcatgg agcatgaagg ttcccaggac agcttactgc ccctggagga agcagcaaat    1740
tcgggcaggg atacctcgat ccctagcatc tggccagcct tctgcagaaa atcccagcct    1800
ccccaagtgg cacagccctc tggaccaggc caagcacagg cccccattca aggtgggaac    1860
acggaccccc tggagctctt ccttgatcaa ctgctgaccg aagtccaact tgaggagcag    1920
gggcctgccc ctgtgaatgt ggaggaaaca tgggagcaaa tggacacaac acctatctgc    1980
ctctcacttc agaagaatat cagactcttc tagatatgct ctga                      2024
```

```
<210> SEQ ID NO 17
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 17

Ser Tyr Trp Met His
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 18

Glu Ile Asn Pro Thr Asn Gly Arg Thr Asn Tyr Ile Glu Lys Phe Lys
1               5                   10                  15

Ser

<210> SEQ ID NO 19
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 19

Gly Thr Arg Ala Tyr His Tyr
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 20

Arg Ala Ser Asp Asn Leu Tyr Ser Asn Leu Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 21

Asp Ala Thr Asn Leu Ala Asp
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 22

Gln His Phe Trp Gly Thr Pro Leu Thr
1               5
```

```
<210> SEQ ID NO 23
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 23

Gly Tyr Thr Phe Thr Ser Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 24

Asn Pro Thr Asn Gly Arg
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 25

Thr Ser Tyr Trp Met His
1               5

<210> SEQ ID NO 26
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 26

Trp Ile Gly Glu Ile Asn Pro Thr Asn Gly Arg Thr Asn
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 27

Ala Arg Gly Thr Arg Ala
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 28

Tyr Ser Asn Leu Ala Trp Tyr
1               5
```

```
<210> SEQ ID NO 29
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 29

Leu Leu Val Tyr Asp Ala Thr Asn Leu Ala
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 30

Gln His Phe Trp Gly Thr Pro Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 31

Gln His Phe Ala Gly Thr Pro Leu Thr
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 32

Gln His Phe Ala Gly Thr Pro Leu
1               5

<210> SEQ ID NO 33
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 33

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asn Pro Thr Asn Gly Arg Thr Asn Tyr Ile Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Ala Arg Gly Thr Arg Ala Tyr His Tyr Trp Gly Gln Gly Thr Ser Val
            100                 105                 110

Thr Val Ser Ser
        115
```

<210> SEQ ID NO 34
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 34

```
Asp Ile Gln Met Thr Gln Ser Pro Ala Ser Leu Ser Val Ser Val Gly
1               5                   10                  15

Glu Thr Val Thr Ile Thr Cys Arg Ala Ser Asp Asn Leu Tyr Ser Asn
            20                  25                  30

Leu Ala Trp Tyr Gln Gln Lys Gln Gly Lys Ser Pro Gln Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Gly Thr Pro Leu
                85                  90                  95

Thr Phe Gly Ala Gly Thr Lys Leu Glu Leu Lys
            100                 105
```

<210> SEQ ID NO 35
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 35

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Asn Pro Thr Asn Gly Arg Thr Asn Tyr Ile Glu Lys Phe
    50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Met Val
            100                 105                 110

Thr Val Ser Ser
        115
```

<210> SEQ ID NO 36
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Leu Tyr Ser Asn
            20                  25                  30

Leu Ala Trp Tyr Gln Gln Lys Pro Gly Lys Ser Pro Lys Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Ser
65                  70                  75                  80

Glu Asp Phe Gly Thr Tyr Tyr Cys Gln His Phe Trp Gly Thr Pro Leu
                85                  90                  95

Thr Phe Gly Ala Gly Thr Lys Leu Glu Leu Lys
            100                 105
```

<210> SEQ ID NO 37
<211> LENGTH: 330
<212> TYPE: PRT
<213> ORGANISM: Artificial Sequence
<220> FEATURE:
<223> OTHER INFORMATION: Synthetic polypeptide

<400> SEQUENCE: 37

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

Pro Ser Asp Ile Ala Val Glu Trp Glu Ser Asn Gly Gln Pro Glu Asn
            245                 250                 255

Asn Tyr Lys Thr Thr Pro Pro Val Leu Asp Ser Asp Gly Ser Phe Phe
            260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
    290                 295                 300

Gln Lys Ser Leu Ser Leu Ser Pro Gly Lys
305                 310                 315                 320

<210> SEQ ID NO 38
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro
            100                 105                 110

<210> SEQ ID NO 39
<211> LENGTH: 446
<212> TYPE: PRT
<213> ORGANISM: Artificial Sequence
<220> FEATURE:
<223> OTHER INFORMATION: Synthetic polypeptide

<400> SEQUENCE: 39

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Thr Asn Gly Arg Thr Asn Tyr Ile Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Thr Arg Ala Tyr His Tyr Trp Gly Gln Gly Thr Ser Val
            100                 105                 110

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 40
<211> LENGTH: 226
<212> TYPE: PRT
<213> ORGANISM: Artificial Sequence
<220> FEATURE:
<223> OTHER INFORMATION: Synthetic polypeptide

<400> SEQUENCE: 40

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30
```

```
Trp Met His Trp Val Lys Gln Arg Pro Gly Gln Gly Leu Glu Trp Ile
            35                  40                  45

Gly Glu Ile Asn Pro Thr Asn Gly Arg Thr Asn Tyr Ile Glu Lys Phe
 50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly Thr Arg Ala Tyr His Tyr Trp Gly Gln Gly Thr Ser Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro
225

<210> SEQ ID NO 41
<211> LENGTH: 446
<212> TYPE: PRT
<213> ORGANISM: Artificial Sequence
<220> FEATURE:
<223> OTHER INFORMATION: Synthetic polypeptide

<400> SEQUENCE: 41

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Trp Met His Trp Val Arg Gln Ala Pro Gly Gln Arg Leu Glu Trp Ile
            35                  40                  45

Gly Glu Ile Asn Pro Thr Asn Gly Arg Thr Asn Tyr Ile Glu Lys Phe
 50                  55                  60

Lys Ser Arg Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Thr Arg Ala Tyr His Tyr Trp Gly Gln Gly Thr Met Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 42
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Leu Tyr Ser Asn
            20                  25                  30

Leu Ala Trp Tyr Gln Gln Lys Pro Gly Lys Ser Pro Lys Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Ser
65                  70                  75                  80
```

Glu Asp Phe Gly Thr Tyr Tyr Cys Gln His Phe Trp Gly Thr Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
            115                 120                 125

Thr Ala Ala Leu Gly Cys Leu Val Lys Asp Tyr Phe Pro Glu Pro Val
            130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
            165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Lys Val Glu Pro Lys
            195                 200                 205

Ser Cys Asp Lys Thr His Thr Cys Pro
            210                 215

<210> SEQ ID NO 43
<211> LENGTH: 226
<212> TYPE: PRT
<213> ORGANISM: Artificial Sequence
<220> FEATURE:
<223> OTHER INFORMATION: Synthetic polypeptide

<400> SEQUENCE: 43

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Glu Ile Asn Pro Thr Asn Gly Arg Thr Asn Tyr Ile Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Gly Thr Arg Ala Tyr His Tyr Trp Gly Gln Gly Thr Ser Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro
225

<210> SEQ ID NO 44
<211> LENGTH: 226
<212> TYPE: PRT
<213> ORGANISM: Artificial Sequence
<220> FEATURE:
<223> OTHER INFORMATION: Synthetic polypeptide

<400> SEQUENCE: 44

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Asn Pro Thr Asn Gly Arg Thr Asn Tyr Ile Glu Lys Phe
    50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro
225

<210> SEQ ID NO 45
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 45
gggcatttta atatatctct gaact                                    25

<210> SEQ ID NO 46
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 46
agttcagaga tatattaaaa tgccc                                       25

<210> SEQ ID NO 47
<211> LENGTH: 25
<212> TYPE: DNA
<213> ORGANISM: Artificial Sequence
<220> FEATURE:
<223> OTHER INFORMATION: Synthetic

<400> SEQUENCE: 47
cctcttacct cagttacaat ttata                                       25

<210> SEQ ID NO 48
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified by 2'Fluoro
<220> FEATURE:
<221> NAME/KEY: misc_feature
<222> LOCATION: (2)..(2)
<223> OTHER INFORMATION: modified by 2'OMe
<220> FEATURE:
<221> NAME/KEY: misc_feature
<222> LOCATION: (3)..(3)
<223> OTHER INFORMATION: modified by 2'Fluoro
<220> FEATURE:
<221> NAME/KEY: misc_feature
<222> LOCATION: (4)..(4)
<223> OTHER INFORMATION: modified by 2'OMe
<220> FEATURE:
<221> NAME/KEY: misc_feature
<222> LOCATION: (5)..(5)
<223> OTHER INFORMATION: modified by 2'Fluoro
<220> FEATURE:
<221> NAME/KEY: misc_feature
<222> LOCATION: (6)..(6)
<223> OTHER INFORMATION: modified by 2'OMe
<220> FEATURE:
<221> NAME/KEY: misc_feature
<222> LOCATION: (7)..(7)
<223> OTHER INFORMATION: modified by 2'Fluoro
<220> FEATURE:
<221> NAME/KEY: misc_feature
<222> LOCATION: (8)..(8)
<223> OTHER INFORMATION: modified by 2'OMe
<220> FEATURE:
<221> NAME/KEY: misc_feature
<222> LOCATION: (9)..(9)
<223> OTHER INFORMATION: modified by 2'Fluoro
<220> FEATURE:
<221> NAME/KEY: misc_feature
<222> LOCATION: (10)..(10)
<223> OTHER INFORMATION: modified by 2'OMe
<220> FEATURE:
<221> NAME/KEY: misc_feature
<222> LOCATION: (11)..(11)
<223> OTHER INFORMATION: modified by 2'Fluoro
<220> FEATURE:
<221> NAME/KEY: misc_feature
<222> LOCATION: (12)..(12)
<223> OTHER INFORMATION: modified by 2'OMe
<220> FEATURE:
<221> NAME/KEY: misc_feature
<222> LOCATION: (13)..(13)
<223> OTHER INFORMATION: modified by 2'Fluoro
<220> FEATURE:
<221> NAME/KEY: misc_feature
<222> LOCATION: (14)..(14)
<223> OTHER INFORMATION: modified by 2'OMe
<220> FEATURE:

```
<221> NAME/KEY: misc_feature
<222> LOCATION: (15)..(15)
<223> OTHER INFORMATION: modified by 2'Fluoro
<220> FEATURE:
<221> NAME/KEY: misc_feature
<222> LOCATION: (16)..(16)
<223> OTHER INFORMATION: modified by 2'OMe
<220> FEATURE:
<221> NAME/KEY: misc_feature
<222> LOCATION: (17)..(17)
<223> OTHER INFORMATION: modified by 2'Fluoro
<220> FEATURE:
<221> NAME/KEY: misc_feature
<222> LOCATION: (18)..(18)
<223> OTHER INFORMATION: modified by 2'OMe
<220> FEATURE:
<221> NAME/KEY: misc_feature
<222> LOCATION: (19)..(19)
<223> OTHER INFORMATION: modified by 2'Fluoro
<220> FEATURE:
<221> NAME/KEY: misc_feature
<222> LOCATION: (20)..(20)
<223> OTHER INFORMATION: modified by 2'OMe
<220> FEATURE:
<221> NAME/KEY: misc_feature
<222> LOCATION: (21)..(21)
<223> OTHER INFORMATION: modified by 2'Fluoro

<400> SEQUENCE: 48
uccuaugacu guagauuuua u                                              21

<210> SEQ ID NO 49
<211> LENGTH: 23
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified by 2'OMe
<220> FEATURE:
<221> NAME/KEY: misc_feature
<222> LOCATION: (2)..(2)
<223> OTHER INFORMATION: modified by 2'Fluoro
<220> FEATURE:
<221> NAME/KEY: misc_feature
<222> LOCATION: (3)..(3)
<223> OTHER INFORMATION: modified by 2'OMe
<220> FEATURE:
<221> NAME/KEY: misc_feature
<222> LOCATION: (4)..(4)
<223> OTHER INFORMATION: modified by 2'Fluoro
<220> FEATURE:
<221> NAME/KEY: misc_feature
<222> LOCATION: (5)..(5)
<223> OTHER INFORMATION: modified by 2'OMe
<220> FEATURE:
<221> NAME/KEY: misc_feature
<222> LOCATION: (6)..(6)
<223> OTHER INFORMATION: modified by 2'Fluoro
<220> FEATURE:
<221> NAME/KEY: misc_feature
<222> LOCATION: (7)..(7)
<223> OTHER INFORMATION: modified by 2'OMe
<220> FEATURE:
<221> NAME/KEY: misc_feature
<222> LOCATION: (8)..(8)
<223> OTHER INFORMATION: modified by 2'Fluoro
<220> FEATURE:
<221> NAME/KEY: misc_feature
<222> LOCATION: (9)..(9)
<223> OTHER INFORMATION: modified by 2'OMe
<220> FEATURE:
<221> NAME/KEY: misc_feature
<222> LOCATION: (10)..(10)
<223> OTHER INFORMATION: modified by 2'Fluoro
```

```
<220> FEATURE:
<221> NAME/KEY: misc_feature
<222> LOCATION: (11)..(11)
<223> OTHER INFORMATION: modified by 2'OMe
<220> FEATURE:
<221> NAME/KEY: misc_feature
<222> LOCATION: (12)..(12)
<223> OTHER INFORMATION: modified by 2'Fluoro
<220> FEATURE:
<221> NAME/KEY: misc_feature
<222> LOCATION: (13)..(13)
<223> OTHER INFORMATION: modified by 2'OMe
<220> FEATURE:
<221> NAME/KEY: misc_feature
<222> LOCATION: (14)..(14)
<223> OTHER INFORMATION: modified by 2'Fluoro
<220> FEATURE:
<221> NAME/KEY: misc_feature
<222> LOCATION: (15)..(15)
<223> OTHER INFORMATION: modified by 2'OMe
<220> FEATURE:
<221> NAME/KEY: misc_feature
<222> LOCATION: (16)..(16)
<223> OTHER INFORMATION: modified by 2'Fluoro
<220> FEATURE:
<221> NAME/KEY: misc_feature
<222> LOCATION: (17)..(17)
<223> OTHER INFORMATION: modified by 2'OMe
<220> FEATURE:
<221> NAME/KEY: misc_feature
<222> LOCATION: (18)..(18)
<223> OTHER INFORMATION: modified by 2'Fluoro
<220> FEATURE:
<221> NAME/KEY: misc_feature
<222> LOCATION: (19)..(19)
<223> OTHER INFORMATION: modified by 2'OMe
<220> FEATURE:
<221> NAME/KEY: misc_feature
<222> LOCATION: (20)..(20)
<223> OTHER INFORMATION: modified by 2'Fluoro
<220> FEATURE:
<221> NAME/KEY: misc_feature
<222> LOCATION: (21)..(21)
<223> OTHER INFORMATION: modified by 2'OMe
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: misc_feature
<222> LOCATION: (22)..(22)
<223> OTHER INFORMATION: modified by 2'Fluoro
<220> FEATURE:
<221> NAME/KEY: misc_feature
<222> LOCATION: (23)..(23)
<223> OTHER INFORMATION: modified by 2'OMe

<400> SEQUENCE: 49
auaaaaucua cagucauagg aau                                                 23

<210> SEQ ID NO 50
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified by 2'Fluoro
<220> FEATURE:
<221> NAME/KEY: misc_feature
<222> LOCATION: (2)..(2)
<223> OTHER INFORMATION: modified by 2'OMe
<220> FEATURE:
<221> NAME/KEY: misc_feature
<222> LOCATION: (3)..(3)
```

```
<223> OTHER INFORMATION: modified by 2'Fluoro
<220> FEATURE:
<221> NAME/KEY: misc_feature
<222> LOCATION: (4)..(4)
<223> OTHER INFORMATION: modified by 2'OMe
<220> FEATURE:
<221> NAME/KEY: misc_feature
<222> LOCATION: (5)..(5)
<223> OTHER INFORMATION: modified by 2'Fluoro
<220> FEATURE:
<221> NAME/KEY: misc_feature
<222> LOCATION: (6)..(6)
<223> OTHER INFORMATION: modified by 2'OMe
<220> FEATURE:
<221> NAME/KEY: misc_feature
<222> LOCATION: (7)..(7)
<223> OTHER INFORMATION: modified by 2'Fluoro
<220> FEATURE:
<221> NAME/KEY: misc_feature
<222> LOCATION: (8)..(8)
<223> OTHER INFORMATION: modified by 2'OMe
<220> FEATURE:
<221> NAME/KEY: misc_feature
<222> LOCATION: (9)..(9)
<223> OTHER INFORMATION: modified by 2'Fluoro
<220> FEATURE:
<221> NAME/KEY: misc_feature
<222> LOCATION: (10)..(10)
<223> OTHER INFORMATION: modified by 2'OMe
<220> FEATURE:
<221> NAME/KEY: misc_feature
<222> LOCATION: (11)..(11)
<223> OTHER INFORMATION: modified by 2'Fluoro
<220> FEATURE:
<221> NAME/KEY: misc_feature
<222> LOCATION: (12)..(12)
<223> OTHER INFORMATION: modified by 2'OMe
<220> FEATURE:
<221> NAME/KEY: misc_feature
<222> LOCATION: (13)..(13)
<223> OTHER INFORMATION: modified by 2'Fluoro
<220> FEATURE:
<221> NAME/KEY: misc_feature
<222> LOCATION: (14)..(14)
<223> OTHER INFORMATION: modified by 2'OMe
<220> FEATURE:
<221> NAME/KEY: misc_feature
<222> LOCATION: (15)..(15)
<223> OTHER INFORMATION: modified by 2'Fluoro
<220> FEATURE:
<221> NAME/KEY: misc_feature
<222> LOCATION: (16)..(16)
<223> OTHER INFORMATION: modified by 2'OMe
<220> FEATURE:
<221> NAME/KEY: misc_feature
<222> LOCATION: (17)..(17)
<223> OTHER INFORMATION: modified by 2'Fluoro
<220> FEATURE:
<221> NAME/KEY: misc_feature
<222> LOCATION: (18)..(18)
<223> OTHER INFORMATION: modified by 2'OMe
<220> FEATURE:
<221> NAME/KEY: misc_feature
<222> LOCATION: (19)..(19)
<223> OTHER INFORMATION: modified by 2'Fluoro
<220> FEATURE:
<221> NAME/KEY: misc_feature
<222> LOCATION: (20)..(20)
<223> OTHER INFORMATION: modified by 2'OMe
<220> FEATURE:
<221> NAME/KEY: misc_feature
<222> LOCATION: (21)..(21)
<223> OTHER INFORMATION: modified by 2'Fluoro

<400> SEQUENCE: 50
uguaauaacc auaucuaccu u                                            21
```

```
<210> SEQ ID NO 51
<211> LENGTH: 23
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: modified by 2'OMe
<220> FEATURE:
<221> NAME/KEY: misc_feature
<222> LOCATION: (2)..(2)
<223> OTHER INFORMATION: modified by 2'Fluoro
<220> FEATURE:
<221> NAME/KEY: misc_feature
<222> LOCATION: (3)..(3)
<223> OTHER INFORMATION: modified by 2'OMe
<220> FEATURE:
<221> NAME/KEY: misc_feature
<222> LOCATION: (4)..(4)
<223> OTHER INFORMATION: modified by 2'Fluoro
<220> FEATURE:
<221> NAME/KEY: misc_feature
<222> LOCATION: (5)..(5)
<223> OTHER INFORMATION: modified by 2'OMe
<220> FEATURE:
<221> NAME/KEY: misc_feature
<222> LOCATION: (6)..(6)
<223> OTHER INFORMATION: modified by 2'Fluoro
<220> FEATURE:
<221> NAME/KEY: misc_feature
<222> LOCATION: (7)..(7)
<223> OTHER INFORMATION: modified by 2'OMe
<220> FEATURE:
<221> NAME/KEY: misc_feature
<222> LOCATION: (8)..(8)
<223> OTHER INFORMATION: modified by 2'Fluoro
<220> FEATURE:
<221> NAME/KEY: misc_feature
<222> LOCATION: (9)..(9)
<223> OTHER INFORMATION: modified by 2'OMe
<220> FEATURE:
<221> NAME/KEY: misc_feature
<222> LOCATION: (10)..(10)
<223> OTHER INFORMATION: modified by 2'Fluoro
<220> FEATURE:
<221> NAME/KEY: misc_feature
<222> LOCATION: (11)..(11)
<223> OTHER INFORMATION: modified by 2'OMe
<220> FEATURE:
<221> NAME/KEY: misc_feature
<222> LOCATION: (12)..(12)
<223> OTHER INFORMATION: modified by 2'Fluoro
<220> FEATURE:
<221> NAME/KEY: misc_feature
<222> LOCATION: (13)..(13)
<223> OTHER INFORMATION: modified by 2'OMe
<220> FEATURE:
<221> NAME/KEY: misc_feature
<222> LOCATION: (14)..(14)
<223> OTHER INFORMATION: modified by 2'Fluoro
<220> FEATURE:
<221> NAME/KEY: misc_feature
<222> LOCATION: (15)..(15)
<223> OTHER INFORMATION: modified by 2'OMe
<220> FEATURE:
<221> NAME/KEY: misc_feature
<222> LOCATION: (16)..(16)
<223> OTHER INFORMATION: modified by 2'Fluoro
<220> FEATURE:
<221> NAME/KEY: misc_feature
<222> LOCATION: (17)..(17)
<223> OTHER INFORMATION: modified by 2'OMe
<220> FEATURE:
<221> NAME/KEY: misc_feature
<222> LOCATION: (18)..(18)
<223> OTHER INFORMATION: modified by 2'Fluoro
<220> FEATURE:
```

```
<221> NAME/KEY: misc_feature
<222> LOCATION: (19)..(19)
<223> OTHER INFORMATION: modified by 2'OMe
<220> FEATURE:
<221> NAME/KEY: misc_feature
<222> LOCATION: (20)..(20)
<223> OTHER INFORMATION: modified by 2'Fluoro
<220> FEATURE:
<221> NAME/KEY: misc_feature
<222> LOCATION: (21)..(21)
<223> OTHER INFORMATION: modified by 2'OMe
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: misc_feature
<222> LOCATION: (22)..(22)
<223> OTHER INFORMATION: modified by 2'Fluoro
<220> FEATURE:
<221> NAME/KEY: misc_feature
<222> LOCATION: (23)..(23)
<223> OTHER INFORMATION: modified by 2'OMe

<400> SEQUENCE: 51
aagguagaua ugguuauuac aaa                                           23

<210> SEQ ID NO 52
<211> LENGTH: 1710
<212> TYPE: DNA
<213> ORGANISM: Homo sapiens

<400> SEQUENCE: 52
atggccctcc cgacaccctc ggacagcacc ctccccgcgg aagcccgggg acgaggacgg     60
cgacggagac tcgtttggac cccgagccaa agcgaggccc tgcgagcctg ctttgagcgg    120
aacccgtacc cgggcatcgc caccagagaa cggctggccc aggccatcgg cattccggag    180
cccagggtcc agatttggtt tcagaatgag aggtcacgcc agctgaggca gcaccggcgg    240
gaatctcggc cctggcccgg agacgcggcc cgccagaag gccggcgaaa gcggaccgcc     300
gtcaccggat cccagaccgc cctgctcctc cgagcctttg agaaggatcg cttttccaggc   360 atcgccgccc gggaggagct ggccagagag acgggcctcc cggagtccag gattcagatc    420
tggtttcaga atcgaagggc caggcacccg ggacagggtg gcagggcgcc cgcgcaggca    480
ggcggcctgt gcagcgcggc cccggcgggg ggtcaccctg ctccctcgtg ggtcgccttc    540
gcccacaccg gcgcgtgggg aacggggctt cccgcacccc acgtgccctg cgcgcctggg    600
gctctcccac agggggcttt cgtgagccag gcagcgaggg ccgcccccgc gctgcagccc    660
agccaggccg cgccggcaga ggggatctcc caacctgccc cggcgcgcgg ggatttcgcc    720
tacgccgccc cggctcctcc ggacggggcg ctctcccacc ctcaggctcc tcgctggcct    780
ccgcacccgg gcaaaagccg ggaggaccgg gacccgcagc gcgacggcct gccgggcccc    840
tgcgcggtgg cacagcctgg gcccgctcaa gcggggccgc agggccaagg ggtgcttgcg    900
ccacccacgt cccaggggag tccgtggtgg ggctggggcc gggtccccca ggtcgccggg    960
gcggcgtggg aaccccaagc cggggcagct ccacctcccc agcccgcgcc ccgggacgcc   1020
tccgcctccg cgcggcaggg gcagatgcaa ggcatcccgg cgccctccca ggcgctccag   1080
gagccggcgc cctggtctgc actcccctgc ggcctgctgc tggatgagct cctggcgagc   1140
ccggagtttc tgcagcaggc gcaacctctc ctagaaacgg aggccccggg ggagctggag   1200
gcctcggaag aggccgcctc gctggaagca cccctcagcg aggaagaata ccgggctctg   1260
ctggaggagc tttaggacgc ggggttggga cggggtcggg tggttcgggg cagggcggtg   1320
```

```
gcctctcttt cgcggggaac acctggctgg ctacggaggg gcgtgtctcc gccccgcccc    1380
ctccaccggg ctgaccggcc tgggattcct gccttctagg tctaggcccg gtgagagact    1440
ccacaccgcg gagaactgcc attctttcct gggcatcccg gggatcccag agccggccca    1500
ggtaccagca gacctgcgcg cagtgcgcac cccggctgac gtgcaaggga gctcgctggc    1560
ctctctgtgc ccttgttctt ccgtgaaatt ctggctgaat gtctccccc accttccgac    1620 gctgtctagg caaacctgga ttagagttac atctcctgga tgattagttc agagatatat    1680
taaaatgccc cctccctgtg gatcctatag                                    1710
```

METHODS OF DELIVERING AN OLIGONUCLEOTIDE TO A SUBJECT HAVING FACIOSCAPULOHUMERAL MUSCULAR DYSTROPHY

RELATED APPLICATIONS

This application is a continuation of U.S. application Ser. No. 17/671,707, entitled "METHODS OF INTRAVENOUSLY DELIVERING ANTI-TRANSFERRIN ANTIBODY/OLIGONUCLEOTIDE COMPLEXES TO SUBJECTS HAVING MUSCULAR DYSTROPHY," filed Feb. 15, 2022, now U.S. Pat. No. 11,390,682, which is a continuation of U.S. application Ser. No. 17/400,295, filed Aug. 12, 2021, entitled "COMPLEX COMPRISING ANTI-TRANSFERRIN RECEPTOR ANTIBODY COVALENTLY LINKED TO AN OLIGONUCLEOTIDE THAT TARGETS DUX4 RNA," now U.S. Pat. No. 11,286,305, which is a continuation of U.S. application Ser. No. 17/205,123, entitled "A METHOD FOR REDUCING EXPRESSION OF DUX4 IN A MUSCLE CELL BY ADMINISTERING AN ANTI-TRANSFERRIN RECEPTOR ANTIBODY LINKED TO AN OLIGONUCLEOTIDE TARGETING DUX4," filed Mar. 18, 2021, now U.S. Pat. No. 11,111,309, which is a continuation of U.S. application Ser. No. 17/264,948, entitled "MUSCLE TARGETING COMPLEXES AND USES THEREOF FOR TREATING FACIOSCAPULOHUMERAL MUSCULAR DYSTROPHY," filed Feb. 1, 2021, which is a national stage filing under 35 U.S.C. § 371 of International Application No. PCT/US2019/044990, entitled "MUSCLE TARGETING COMPLEXES AND USES THEREOF FOR TREATING FACIOSCAPULOHUMERAL MUSCULAR DYSTROPHY," filed Aug. 2, 2019, which claims the benefit of the filing date of U.S. Provisional Application No. 62/713,933, entitled "MUSCLE TARGETING COMPLEXES AND USES THEREOF FOR TREATING FACIOSCAPULOHUMERAL MUSCULAR DYSTROPHY" filed Aug. 2, 2018, the contents of each of which are incorporated herein by reference in their entirety.

FIELD OF THE INVENTION

The present application relates to targeting complexes for delivering molecular payloads (e.g., oligonucleotides) to cells and uses thereof, particularly uses relating to treatment of disease.

REFERENCE TO THE SEQUENCE LISTING

The present application is being filed along with a Sequence Listing in electronic format. The Sequence Listing is provided as a file entitled D082470001US05-SEQ-ZJG.txt created on Jun. 22, 2022, which is 72,632 bytes in size. The information in electronic format of the sequence listing is incorporated herein by reference in its entirety.

BACKGROUND OF INVENTION

Muscular dystrophies (MDs) are a group of diseases characterized by the progressive weakness and loss of muscle mass. These diseases are caused by mutations in genes which encode proteins needed to form healthy muscle tissue. Facioscapulohumeral muscular dystrophy (FSHD) is a dominantly inherited type of MD which primarily affects muscles of the face, shoulder blades, and upper arms. Other symptoms of FSHD include abdominal muscle weakness, retinal abnormalities, hearing loss, and joint pain and inflammation. FSHD is the most prevalent of the nine types of MD affecting both adults and children, with a worldwide incidence of about 1 in 8,300 people. FSHD is caused by aberrant production of double homeobox 4 (DUX4), a protein whose function is unknown. The DUX4 gene, which encodes the DUX4 protein, is located in the D4Z4 repeat region on chromosome 4 and is typically expressed only in fetal development, after which it is repressed by hypermethylation of the D4Z4 repeats which surround and compact the DUX4 gene. Two types of FSHD, Type 1 and Type 2 have been described. Type 1, which accounts for about 95% of cases, is associated with deletions of D4Z4 repeats on chromosome 4. Unaffected individuals generally have more than 10 repeats arrayed in the subtelomeric region of chromosome 4, whereas the most common form of FSHD (FSHD1) is caused by a contraction of the array to fewer than 10 repeats, associated with decreased epigenetic repression and variegated expression of DUX4 in skeletal muscle. Type 2 FSHD, which accounts for about 5% of cases, is associated with mutations of the SMCHD1 gene on chromosome 18. Besides supportive care and treatments to address the symptoms of the disease, there are no effective therapies for FSHD.

SUMMARY OF INVENTION

According to some aspects, the disclosure provides complexes that target muscle cells for purposes of delivering molecular payloads to those cells. In some embodiments, complexes provided herein are particularly useful for delivering molecular payloads that inhibit the expression or activity of DUX4, e.g., in a subject having or suspected of having Facioscapulohumeral muscular dystrophy (FSHD). Accordingly, in some embodiments, complexes provided herein comprise muscle-targeting agents (e.g., muscle targeting antibodies) that specifically bind to receptors on the surface of muscle cells for purposes of delivering molecular payloads to the muscle cells. In some embodiments, the complexes are taken up into the cells via a receptor mediated internalization, following which the molecular payload may be released to perform a function inside the cells. For example, complexes engineered to deliver oligonucleotides may release the oligonucleotides such that the oligonucleotides can inhibit DUX4 gene expression in the muscle cells. In some embodiments, the oligonucleotides are released by endosomal cleavage of covalent linkers connecting oligonucleotides and muscle-targeting agents of the complexes.

Some aspects of the disclosure comprise a complex comprising a muscle-targeting agent covalently linked to a molecular payload configured for inhibiting expression or activity of DUX4, wherein the muscle-targeting agent specifically binds to an internalizing cell surface receptor on muscle cells.

In some embodiments, the muscle-targeting agent is a muscle-targeting antibody. In some embodiments, a muscle-targeting antibody is an antibody that specifically binds to an extracellular epitope of a transferrin receptor (e.g., an epitope of the apical domain of the transferrin receptor). A muscle-targeting antibody may specifically binds to an epitope of a sequence in the range of C89 to F760 of SEQ ID NO: 1-3. In some embodiments, the equilibrium dissociation constant (Kd) of binding of a muscle-targeting antibody to a transferrin receptor is in a range from $10^{-11}$ M to $10^{-6}$ M.

In some embodiments, a muscle-targeting antibody of a complex competes for specific binding to an epitope of a transferrin receptor with an antibody listed in Table 1 (e.g., competes for specific binding to an epitope of a transferrin receptor with an Kd of less than or equal to $10^{-6}$ M, e.g., in a range of $10^{-11}$ M to $10^{-6}$ M).

In some embodiments, a muscle-targeting antibody of a complex does not specifically bind to the transferrin binding site of a transferrin receptor and/or does not inhibit binding of transferrin to a transferrin receptor. In some embodiments, a muscle-targeting antibody of a complex is cross-reactive with extracellular epitopes of two or more of a human, non-human primate and rodent transferrin receptor. In some embodiments, a muscle-targeting antibody of a complex is configured to promote transferrin receptor mediated internalization of the molecular payload into a muscle cell.

A muscle-targeting antibody (e.g., muscle-targeting antibody is an antibody that specifically binds to an extracellular epitope of a transferrin receptor) is a chimeric antibody, wherein optionally the chimeric antibody is a humanized monoclonal antibody. A muscle-targeting antibody may be in the form of a ScFv, Fab fragment, Fab' fragment, F(ab')2 fragment, or Fv fragment.

In some embodiments, a molecular payload of a complex is an oligonucleotide (e.g., an oligonucleotide that targets DUX4). In some embodiments, an oligonucleotide comprises at least 15 consecutive nucleotides of SEQ ID NO: 45. In some embodiments, an oligonucleotide comprises SEQ ID NO: 45. In some embodiments, an oligonucleotide comprises a sequence that is complementary to at least 15 consecutive nucleotides of SEQ ID NO: 46.

In some embodiments, an oligonucleotide comprises a region of complementarity to a DUX4 gene. In some embodiments, an oligonucleotide comprises an antisense strand that hybridizes, in a cell, with a wild-type DUX4 mRNA transcript encoded by the allele. In some embodiments, an oligonucleotide comprises an antisense strand that hybridizes, in a cell, with a mutant DUX4 mRNA transcript encoded by the allele. An oligonucleotide may comprise a strand complementary to the coding sequence of DUX4.

In some embodiments, an oligonucleotide comprises a strand complementary to the non-coding sequence of DUX4. In some embodiments, an oligonucleotide may comprise a strand complementary to a 5' or 3' UTR sequence of DUX4. In some embodiments, an oligonucleotide mediates epigenetic silencing of DUX4.

An oligonucleotide of the disclosure may comprise at least one modified internucleotide linkage (e.g., a phosphorothioate linkage). In some embodiments, an oligonucleotide comprises phosphorothioate linkages in the Rp stereochemical conformation and in the Sp stereochemical conformation. In some embodiments, an oligonucleotide comprises phosphorothioate linkages that are all in the Rp stereochemical conformation. In other embodiments, an oligonucleotide comprises phosphorothioate linkages that are all in the Sp stereochemical conformation.

An oligonucleotide of the disclosure may comprise one or more modified nucleotides (e.g., 2'-modified nucleotides). In some embodiments, a modified nucleotide is a 2'-O-methyl, 2'-fluoro (2'-F), 2'-O-methoxyethyl (2'-MOE), or 2', 4'-bridged nucleotide. In some embodiments, a modified nucleotides is a bridged nucleotide (e.g., selected from: 2',4'-constrained 2'-O-ethyl (cEt) and locked nucleic acid (LNA) nucleotides).

In some embodiments, an oligonucleotide is a gapmer oligonucleotide that directs RNAse H-mediated cleavage of the DUX4 mRNA transcript in a cell. A gapmer oligonucleotide may comprise a central portion of 5 to 15 deoxyribonucleotides flanked by wings of 2 to 8 modified nucleotides (e.g., 2'-modified nucleotides).

In some embodiments, an oligonucleotide is a mixmer oligonucleotide (e.g., a mixmer oligonucleotide inhibits translation of a DUX4 mRNA transcript). A mixmer oligonucleotide may comprise two or more different 2' modified nucleotides.

In some embodiments, an oligonucleotide is an RNAi oligonucleotide that promotes RNAi-mediated cleavage of the DUX4 mRNA transcript. An RNAi oligonucleotide may be a double-stranded oligonucleotide of 19 to 25 nucleotides in length. In some embodiments, an RNAi oligonucleotide comprises at least one 2' modified nucleotide.

In some embodiments, an oligonucleotide comprises a guide sequence for a genome editing nuclease.

In some embodiments, an oligonucleotide is a phosphorodiamidite morpholino oligomer (PMO).

In other embodiments, a molecular payload is a polypeptide (e.g., a polypeptide that inhibits DUX4 expression). In some embodiments, a molecular payload is a polypeptide that binds to a DUX4 enhancer sequence, thereby blocking recruitment of one or more activators of DUX4 expression.

In some embodiments, a muscle-targeting agent is covalently linked to a molecular payload via a cleavable linker (e.g., a protease-sensitive linker, pH-sensitive linker, or glutathione-sensitive linker). A protease-sensitive linker may comprise a sequence cleavable by a lysosomal protease and/or an endosomal protease. In some embodiments, a protease-sensitive linker comprises a valine-citrulline dipeptide sequence. A pH-sensitive linker may be cleaved at a pH in a range of 4 to 6.

In some embodiments, a muscle-targeting agent is covalently linked to a molecular payload via non-cleavable linker (e.g., an alkane linker).

In some embodiments, a muscle-targeting antibody comprises a non-natural amino acid to which an oligonucleotide can be covalently linked. In some embodiments, a muscle-targeting antibody is covalently linked to an oligonucleotide via conjugation to a lysine residue or a cysteine residue of the antibody. In some embodiments, an oligonucleotide is conjugated to a cysteine residue of the antibody via a maleimide-containing linker, optionally wherein the maleimide-containing linker comprises a maleimidocaproyl or maleimidomethyl cyclohexane-1-carboxylate group.

In some embodiments, a muscle-targeting antibody is a glycosylated antibody that comprises at least one sugar moiety to which a oligonucleotide is covalently linked. In some embodiments, a glycosylated antibody that comprises at least one sugar moiety that is a branched mannose. In some embodiments, a muscle-targeting antibody is a glycosylated antibody that comprises one to four sugar moieties each of which is covalently linked to a separate oligonucleotide. In some embodiments, a muscle-targeting antibody is a fully-glycosylated antibody or a partially-glycosylated antibody. A partially-glycosylated antibody may be produced via chemical or enzymatic means. In some embodiments, a partially-glycosylated antibody is produced in a cell that is deficient for an enzyme in the N- or O-glycosylation pathway.

Some aspects of the disclosure comprise a method of delivering an molecular payload to a cell expressing transferrin receptor, the method comprising contacting the cell with a complex comprising a muscle-targeting agent covalently linked to a molecular payload configured for inhibiting expression or activity of DUX4.

Some aspects of the disclosure comprise a method of inhibiting expression or activity of DUX4 in a cell, the method comprising contacting the cell with a complex comprising a muscle-targeting agent covalently linked to a molecular payload configured for inhibiting expression or activity of DUX4 in an amount effective for promoting internalization of the molecular payload to the cell. In some embodiments, the cell is in vitro. In some embodiments, the cell is in a subject. In some embodiments, the subject is a human.

Some aspects of the disclosure comprise a method of treating a subject having one or more deletions of a D4Z4 repeat in chromosome 4 that is associated with facioscapulohumeral muscular dystrophy, the method comprising administering to the subject an effective amount of a complex comprising a muscle-targeting agent covalently linked to a molecular payload configured for inhibiting expression or activity of DUX4. In some embodiments, the subject has 10 or fewer D4Z4 repeats (e.g., the subject has 9, 8, 7, 6, 5, 4, 3, 2, or 1 D4Z4 repeats). In some embodiments, the subject has no D4Z4 repeats.

DETAILED DESCRIPTION OF INVENTION

Figure 1:
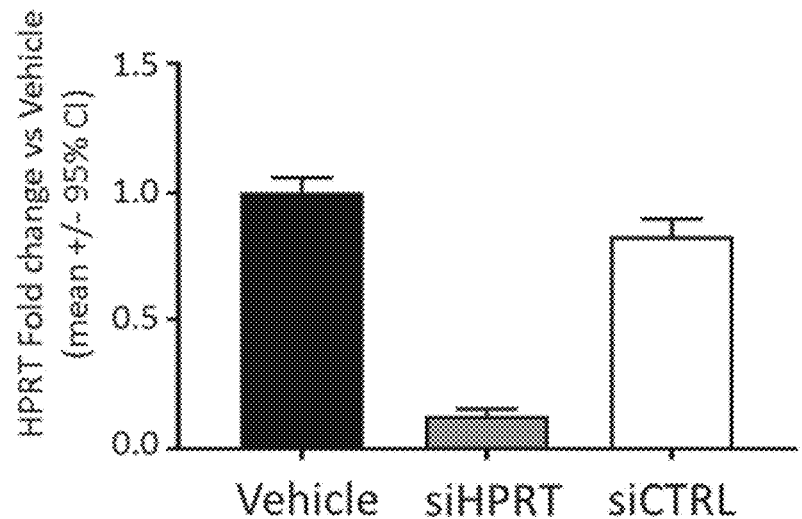
FIG. 1 depicts a non-limiting schematic showing the effect of transfecting cells with an siRNA.

Aspects of the disclosure relate to a recognition that while certain molecular payloads (e.g., oligonucleotides, peptides, small molecules) can have beneficial effects in muscle cells, it has proven challenging to effectively target such cells. As described herein, the present disclosure provides complexes comprising muscle-targeting agents covalently linked to molecular payloads in order to overcome such challenges. In some embodiments, the complexes are particularly useful for delivering molecular payloads that inhibit the expression or activity of target genes in muscle cells, e.g., in a subject having or suspected of having a rare muscle disease. For example, in some embodiments, complexes are provided for targeting a DUX4 to treat subjects having FSHD. In some embodiments, complexes provided herein comprise oligonucleotides that inhibit expression of DUX4 in a subject that has one or more D4Z4 repeat deletions on chromosome 4. In some embodiments, complexes provided herein comprise molecular payloads such as guide molecules (e.g., guide RNAs) that are capable of targeting nucleic acid programmable nucleases (e.g., Cas9) to a DUX4 gene in order to inactivate the gene in muscle cells, for example, by removing a portion of the DUX4 gene, or by introducing an inactivating mutation or stop codon into the DUX4 gene. In some embodiments, such nucleic programmable nucleases could be used to inactivate DUX4 that is aberrantly expressed in muscle cells.

Further aspects of the disclosure, including a description of defined terms, are provided below.

I. Definitions

Administering: As used herein, the terms "administering" or "administration" means to provide a complex to a subject in a manner that is physiologically and/or pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a F(ab')2 fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha (α), delta (Δ), epsilon (ε), gamma (γ) or mu (μ) heavy chain. In some embodiments, the heavy chain of an antibody described herein can comprise a human alpha (α), delta (Δ), epsilon (ε), gamma (γ) or mu (μ) heavy chain. In a particular embodiment, an antibody described herein comprises a human gamma 1 CH1, CH2, and/or CH3 domain. In some embodiments, the amino acid sequence of the VH domain comprises the amino acid sequence of a human gamma (γ) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

CDR: As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

CDR-grafted antibody: The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

Chimeric antibody: The term "chimeric antibody" refers to antibodies which comprise heavy and light chain variable region sequences from one species and constant region sequences from another species, such as antibodies having murine heavy and light chain variable regions linked to human constant regions.

Complementary: As used herein, the term "complementary" refers to the capacity for precise pairing between two nucleotides or two sets of nucleotides. In particular, complementary is a term that characterizes an extent of hydrogen bond pairing that brings about binding between two nucleotides or two sets of nucleotides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Conservative amino acid substitution: As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, N.Y., 2012, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Covalently linked: As used herein, the term "covalently linked" refers to a characteristic of two or more molecules being linked together via at least one covalent bond. In some embodiments, two molecules can be covalently linked together by a single bond, e.g., a disulfide bond or disulfide bridge, that serves as a linker between the molecules. However, in some embodiments, two or more molecules can be covalently linked together via a molecule that serves as a linker that joins the two or more molecules together through multiple covalent bonds. In some embodiments, a linker may be a cleavable linker. However, in some embodiments, a linker may be a non-cleavable linker.

Cross-reactive: As used herein and in the context of a targeting agent (e.g., antibody), the term "cross-reactive," refers to a property of the agent being capable of specifically binding to more than one antigen of a similar type or class (e.g., antigens of multiple homologs, paralogs, or orthologs) with similar affinity or avidity. For example, in some embodiments, an antibody that is cross-reactive against human and non-human primate antigens of a similar type or class (e.g., a human transferrin receptor and non-human primate transferring receptor) is capable of binding to the human antigen and non-human primate antigens with a similar affinity or avidity. In some embodiments, an antibody is cross-reactive against a human antigen and a rodent antigen of a similar type or class. In some embodiments, an antibody is cross-reactive against a rodent antigen and a non-human primate antigen of a similar type or class. In some embodiments, an antibody is cross-reactive against a human antigen, a non-human primate antigen, and a rodent antigen of a similar type or class.

DUX4: As used herein, the term "DUX4" refers to a gene that encodes double homeobox 4, a protein which is generally expressed during fetal development and in the testes of adult males. In some embodiments, DUX4 may be a human (Gene ID: 100288687), non-human primate (e.g., Gene ID: 750891, Gene ID: 100405864), or rodent gene (e.g., Gene ID: 306226). In humans, expression of the DUX4 gene outside of fetal development and the testes is associated with facioscapulohumeral muscular dystrophy. In addition, multiple human transcript variants (e.g., as annotated under GenBank RefSeq Accession Numbers: NM_001293798.2, NM_001306068.2 (SEQ ID NO: 52), NM_001363820.1) have been characterized that encode different protein isoforms.

Facioscapulohumeral muscular dystrophy (FSHD): As used herein, the term "facioscapulohumeral muscular dystrophy (FSHD)" refers to a genetic disease caused by mutations in the DUX4 gene or SMCHD1 gene that is characterized by muscle mass loss and muscle atrophy, primarily in the muscles of the face, shoulder blades, and upper arms. Two types of the disease, Type 1 and Type 2, have been described. Type I is associated with deletions in D4Z4 repeat regions on chromosome 4 which contain the DUX4 gene. Type 2 is associated with mutations in the SMCHD1 gene. Both Type 1 and Type 2 FSHD are characterized by aberrant production of the DUX4 protein after fetal development outside of the testes. Facioscapulohumeral dystrophy, the genetic basis for the disease, and related symptoms are described in the art (see, e.g. Campbell, A. E., et al., "Facioscapulohumeral dystrophy: Activatin an early embryonic transcriptional program in human skeletal muscle" Human Mol Genet. (2018); and Tawil, R. "Facioscapulohumeral muscular dystrophy" Handbook Clin. Neurol. (2018), 148: 541-548.) FSHD Type 1 is associated with Online Mendelian Inheritance in Man (OMIM) Entry #158900. FSHD Type 2 is associated with OMIM Entry #158901.

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-transferrin receptor antibodies and antigen binding portions are provided. Such antibodies may be generated by obtaining murine anti-transferrin receptor monoclonal antibodies using traditional hybridoma technology followed by humanization using in vitro genetic engineering, such as those disclosed in Kasaian et al PCT publication No. WO 2005/123126 A2.

Internalizing cell surface receptor: As used herein, the term, "internalizing cell surface receptor" refers to a cell surface receptor that is internalized by cells, e.g., upon external stimulation, e.g., ligand binding to the receptor. In some embodiments, an internalizing cell surface receptor is internalized by endocytosis. In some embodiments, an internalizing cell surface receptor is internalized by clathrin-mediated endocytosis. However, in some embodiments, an internalizing cell surface receptor is internalized by a clathrin-independent pathway, such as, for example, phagocytosis, macropinocytosis, caveolae- and raft-mediated uptake or constitutive clathrin-independent endocytosis. In some embodiments, the internalizing cell surface receptor comprises an intracellular domain, a transmembrane domain, and/or an extracellular domain, which may optionally further comprise a ligand-binding domain. In some embodiments, a cell surface receptor becomes internalized by a cell after ligand binding. In some embodiments, a ligand may be a muscle-targeting agent or a muscle-targeting antibody. In some embodiments, an internalizing cell surface receptor is a transferrin receptor.

Isolated antibody: An "isolated antibody", as used herein, is intended to refer to an antibody that is substantially free of other antibodies having different antigenic specificities (e.g., an isolated antibody that specifically binds transferrin receptor is substantially free of antibodies that specifically bind antigens other than transferrin receptor). An isolated antibody that specifically binds transferrin receptor complex may, however, have cross-reactivity to other antigens, such as transferrin receptor molecules from other species. Moreover, an isolated antibody may be substantially free of other cellular material and/or chemicals.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Molecular payload: As used herein, the term "molecular payload" refers to a molecule or species that functions to modulate a biological outcome. In some embodiments, a molecular payload is linked to, or otherwise associated with a muscle-targeting agent. In some embodiments, the molecular payload is a small molecule, a protein, a peptide, a nucleic acid, or an oligonucleotide. In some embodiments, the molecular payload functions to modulate the transcription of a DNA sequence, to modulate the expression of a protein, or to modulate the activity of a protein. In some embodiments, the molecular payload is an oligonucleotide that comprises a strand having a region of complementarity to a target gene.

Muscle-targeting agent: As used herein, the term, "muscle-targeting agent," refers to a molecule that specifically binds to an antigen expressed on muscle cells. The antigen in or on muscle cells may be a membrane protein, for example an integral membrane protein or a peripheral membrane protein. Typically, a muscle-targeting agent specifically binds to an antigen on muscle cells that facilitates internalization of the muscle-targeting agent (and any associated molecular payload) into the muscle cells. In some embodiments, a muscle-targeting agent specifically binds to an internalizing, cell surface receptor on muscles and is capable of being internalized into muscle cells through receptor mediated internalization. In some embodiments, the muscle-targeting agent is a small molecule, a protein, a peptide, a nucleic acid (e.g., an aptamer), or an antibody. In some embodiments, the muscle-targeting agent is linked to a molecular payload.

Muscle-targeting antibody: As used herein, the term, "muscle-targeting antibody," refers to a muscle-targeting agent that is an antibody that specifically binds to an antigen found in or on muscle cells. In some embodiments, a muscle-targeting antibody specifically binds to an antigen on muscle cells that facilitates internalization of the muscle-targeting antibody (and any associated molecular payment) into the muscle cells. In some embodiments, the muscle-targeting antibody specifically binds to an internalizing, cell surface receptor present on muscle cells. In some embodiments, the muscle-targeting antibody is an antibody that specifically binds to a transferrin receptor.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidite morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleotides (e.g. 2'-O-methyl sugar modifications, purine or pyrimidine modifications). In some embodiments, an oligonucleotide may comprise one or more modified internucleotide linkage. In some embodiments, an oligonucleotide may comprise one or more phosphorothioate linkages, which may be in the Rp or Sp stereochemical conformation.

Recombinant antibody: The term "recombinant human antibody", as used herein, is intended to include all human antibodies that are prepared, expressed, created or isolated by recombinant means, such as antibodies expressed using a recombinant expression vector transfected into a host cell (described in more details in this disclosure), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment of the disclosure provides fully human antibodies capable of binding human transferrin receptor which can be generated using techniques well known in the art, such as, but not limited to, using human Ig phage libraries such as those disclosed in Jermutus et al., PCT publication No. WO 2005/007699 A2.

Region of complementarity: As used herein, the term "region of complementarity" refers to a nucleotide sequence, e.g., of a oligonucleotide, that is sufficiently complementary to a cognate nucleotide sequence, e.g., of a target nucleic acid, such that the two nucleotide sequences are capable of annealing to one another under physiological conditions (e.g., in a cell). In some embodiments, a region of complementarity is fully complementary to a cognate nucleotide sequence of target nucleic acid. However, in some embodiments, a region of complementarity is partially complementary to a cognate nucleotide sequence of target nucleic acid (e.g., at least 80%, 90%, 95% or 99% complementarity). In some embodiments, a region of complementarity contains 1, 2, 3, or 4 mismatches compared with a cognate nucleotide sequence of a target nucleic acid.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to the transferrin receptor, e.g., an epitope of the apical domain of transferrin receptor.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having FSHD.

Transferrin receptor: As used herein, the term, "transferrin receptor" (also known as TFRC, CD71, p90, or TFR1) refers to an internalizing cell surface receptor that binds transferrin to facilitate iron uptake by endocytosis. In some embodiments, a transferrin receptor may be of human (NCBI Gene ID 7037), non-human primate (e.g., NCBI Gene ID 711568 or NCBI Gene ID 102136007), or rodent (e.g., NCBI Gene ID 22042) origin. In addition, multiple human transcript variants have been characterized that encoded different isoforms of the receptor (e.g., as annotated under GenBank RefSeq Accession Numbers: NP_001121620.1, NP_003225.2, NP_001300894.1, and NP_001300895.1).

II. Complexes

Provided herein are complexes that comprise a targeting agent, e.g. an antibody, covalently linked to a molecular payload. In some embodiments, a complex comprises a muscle-targeting antibody covalently linked to a oligonucleotide. A complex may comprise an antibody that specifically binds a single antigenic site or that binds to at least two antigenic sites that may exist on the same or different antigens.

A complex may be used to modulate the activity or function of at least one gene, protein, and/or nucleic acid. In some embodiments, the molecular payload present with a complex is responsible for the modulation of a gene, protein, and/or nucleic acids. A molecular payload may be a small molecule, protein, nucleic acid, oligonucleotide, or any molecular entity capable of modulating the activity or function of a gene, protein, and/or nucleic acid in a cell. In some embodiments, a molecular payload is an oligonucleotide that targets a DUX4 in muscle cells.

In some embodiments, a complex comprises a muscle-targeting agent, e.g. an anti-transferrin receptor antibody, covalently linked to a molecular payload, e.g. an antisense oligonucleotide that targets a DUX4.

A. Muscle-Targeting Agents

Some aspects of the disclosure provide muscle-targeting agents, e.g., for delivering a molecular payload to a muscle cell. In some embodiments, such muscle-targeting agents are capable of binding to a muscle cell, e.g., via specifically binding to an antigen on the muscle cell, and delivering an associated molecular payload to the muscle cell. In some embodiments, the molecular payload is bound (e.g., covalently bound) to the muscle targeting agent and is internalized into the muscle cell upon binding of the muscle targeting agent to an antigen on the muscle cell, e.g., via endocytosis. It should be appreciated that various types of muscle-targeting agents may be used in accordance with the disclosure. For example, the muscle-targeting agent may comprise, or consist of, a nucleic acid (e.g., DNA or RNA), a peptide (e.g., an antibody), a lipid (e.g., a microvesicle), or a sugar moiety (e.g., a polysaccharide). Exemplary muscle-targeting agents are described in further detail herein, however, it should be appreciated that the exemplary muscle-targeting agents provided herein are not meant to be limiting.

Some aspects of the disclosure provide muscle-targeting agents that specifically bind to an antigen on muscle, such as skeletal muscle, smooth muscle, or cardiac muscle. In some embodiments, any of the muscle-targeting agents provided herein bind to (e.g., specifically bind to) an antigen on a skeletal muscle cell, a smooth muscle cell, and/or a cardiac muscle cell.

By interacting with muscle-specific cell surface recognition elements (e.g., cell membrane proteins), both tissue localization and selective uptake into muscle cells can be achieved. In some embodiments, molecules that are substrates for muscle uptake transporters are useful for delivering a molecular payload into muscle tissue. Binding to muscle surface recognition elements followed by endocytosis can allow even large molecules such as antibodies to enter muscle cells. As another example molecular payloads conjugated to transferrin or anti-transferrin receptor antibodies can be taken up by muscle cells via binding to transferrin receptor, which may then be endocytosed, e.g., via clathrin-mediated endocytosis.

The use of muscle-targeting agents may be useful for concentrating a molecular payload (e.g., oligonucleotide) in muscle while reducing toxicity associated with effects in other tissues. In some embodiments, the muscle-targeting agent concentrates a bound molecular payload in muscle cells as compared to another cell type within a subject. In some embodiments, the muscle-targeting agent concentrates a bound molecular payload in muscle cells (e.g., skeletal, smooth, or cardiac muscle cells) in an amount that is at least 1, 2, 3, 4, 5, 6, 7, 8, 9, 10, 15, 20, 30, 40, 50, 60, 70, 80, 90, or 100 times greater than an amount in non-muscle cells (e.g., liver, neuronal, blood, or fat cells). In some embodiments, a toxicity of the molecular payload in a subject is reduced by at least 1%, 2%, 3%, 4%, 5%, 10%, 15%, 20%, 25%, 30%, 35%, 40%, 45%, 50%, 55%, 60%, 65%, 70%, 75%, 80%, 90%, or 95% when it is delivered to the subject when bound to the muscle-targeting agent.

In some embodiments, to achieve muscle selectivity, a muscle recognition element (e.g., a muscle cell antigen) may be required. As one example, a muscle-targeting agent may be a small molecule that is a substrate for a muscle-specific uptake transporter. As another example, a muscle-targeting agent may be an antibody that enters a muscle cell via transporter-mediated endocytosis. As another example, a muscle targeting agent may be a ligand that binds to cell surface receptor on a muscle cell. It should be appreciated that while transporter-based approaches provide a direct path for cellular entry, receptor-based targeting may involve stimulated endocytosis to reach the desired site of action.

i. Muscle-Targeting Antibodies

In some embodiments, the muscle-targeting agent is an antibody. Generally, the high specificity of antibodies for their target antigen provides the potential for selectively targeting muscle cells (e.g., skeletal, smooth, and/or cardiac muscle cells). This specificity may also limit off-target toxicity. Examples of antibodies that are capable of targeting a surface antigen of muscle cells have been reported and are within the scope of the disclosure. For example, antibodies that target the surface of muscle cells are described in Arahata K., et al. "Immunostaining of skeletal and cardiac muscle surface membrane with antibody against Duchenne muscular dystrophy peptide" Nature 1988; 333: 861-3; Song K. S., et al. "Expression of caveolin-3 in skeletal, cardiac, and smooth muscle cells. Caveolin-3 is a component of the sarcolemma and co-fractionates with dystrophin and dystrophin-associated glycoproteins" J Biol Chem 1996; 271: 15160-5; and Weisbart R. H. et al., "Cell type specific targeted intracellular delivery into muscle of a monoclonal antibody that binds myosin IIb" Mol Immunol. 2003 March, 39(13):78309; the entire contents of each of which are incorporated herein by reference.

a. Anti-Transferrin Receptor Antibodies

Some aspects of the disclosure are based on the recognition that agents binding to transferrin receptor, e.g., anti-transferrin-receptor antibodies, are capable of targeting muscle cell. Transferrin receptors are internalizing cell surface receptors that transport transferrin across the cellular membrane and participate in the regulation and homeostasis of intracellular iron levels. Some aspects of the disclosure provide transferrin receptor binding proteins, which are capable of binding to transferrin receptor. Accordingly, aspects of the disclosure provide binding proteins (e.g., antibodies) that bind to transferrin receptor. In some embodiments, binding proteins that bind to transferrin receptor are internalized, along with any bound molecular payload, into a muscle cell. As used herein, an antibody that binds to a transferrin receptor may be referred to as an anti-transferrin receptor antibody. Antibodies that bind, e.g. specifically bind, to a transferrin receptor may be internalized into the cell, e.g. through receptor-mediated endocytosis, upon binding to a transferrin receptor.

It should be appreciated that anti-transferrin receptor antibodies may be produced, synthesized, and/or derivatized using several known methodologies, e.g. library design using phage display. Exemplary methodologies have been characterized in the art and are incorporated by reference (Diez, P. et al. "High-throughput phage-display screening in array format", Enzyme and microbial technology, 2015, 79, 34-41; Christoph M. H. and Stanley, J. R. "Antibody Phage Display: Technique and Applications" J Invest Dermatol. 2014, 134:2; Engleman, Edgar (Ed.) "Human Hybridomas and Monoclonal Antibodies." 1985, Springer). In other embodiments, an anti-transferrin antibody has been previously characterized or disclosed. Antibodies that specifically bind to transferrin receptor are known in the art (see, e.g. U.S. Pat. No. 4,364,934, filed Dec. 4, 1979, "Monoclonal antibody to a human early thymocyte antigen and methods for preparing same"; U.S. Pat. No. 8,409,573, filed Jun. 14, 2006, "Anti-CD71 monoclonal antibodies and uses thereof for treating malignant tumor cells"; U.S. Pat. No. 9,708,406, filed May 20, 2014, "Anti-transferrin receptor antibodies and methods of use"; U.S. Pat. No. 9,611,323, filed Dec. 19, 2014, "Low affinity blood brain barrier receptor antibodies and uses therefor"; WO 2015/098989, filed Dec. 24, 2014, "Novel anti-Transferrin receptor antibody that passes through blood-brain barrier"; Schneider C. et al. "Structural features of the cell surface receptor for transferrin that is recognized by the monoclonal antibody OKT9." J Biol Chem. 1982, 257:14, 8516-8522; Lee et al. "Targeting Rat Anti-Mouse Transferrin Receptor Monoclonal Antibodies through Blood-Brain Barrier in Mouse" 2000, J Pharmacol. Exp. Ther., 292: 1048-1052).

Any appropriate anti-transferrin receptor antibodies may be used in the complexes disclosed herein. Examples of anti-transferrin receptor antibodies, including associated references and binding epitopes, are listed in Table 1. In some embodiments, the anti-transferrin receptor antibody comprises the complementarity determining regions (CDR-H1, CDR-H2, CDR-H3, CDR-L1, CDR-L2, and CDR-L3) of any of the anti-transferrin receptor antibodies provided herein, e.g., anti-transferrin receptor antibodies listed in Table 1.

TABLE 1

List of anti-transferrin receptor antibody clones, including associated references and binding epitope information.

| Antibody Clone Name | Reference(s) | Epitope/Notes |
|---|---|---|
| OKT9 | U.S. Pat. No. 4,364,934, filed Dec. 4, 1979, entitled "MONOCLONAL ANTIBODY TO A HUMAN EARLY THYMOCYTE ANTIGEN AND METHODS FOR PREPARING SAME" Schneider C. et al. "Structural features of the cell surface receptor for transferrin that is recognized by the monoclonal antibody OKT9." J Biol Chem. 1982, 257:14, 8516-8522. | Apical domain of TfR (residues 305-366 of human TfR sequence XM_052730.3, available in GenBank) |
| (From JCR) Clone M11 Clone M23 Clone M27 Clone B84 | WO 2015/098989, filed Dec. 24, 2014, "Novel anti-Transferrin receptor antibody that passes through blood-brain barrier" U.S. Pat. No. 9,994,641, filed Dec. 24, 2014, "Novel anti-Transferrin receptor antibody that passes through blood-brain barrier" | Apical domain (residues 230-244 and 326-347 of TfR) and protease-like domain (residues 461-473) |

TABLE 1-continued

List of anti-transferrin receptor antibody clones, including associated references and binding epitope information.

| Antibody Clone Name | Reference(s) | Epitope/Notes |
|---|---|---|
| (From Genentech) Clones 7A4, 8A2, 15D2, 10D11, 7B10, 15G11, 16G5, 13C3, 16G4, 16F6, 7G7, 4C2, 1B12, and 13D4 | WO 2016/081643, filed May 26, 2016, entitled "ANTI-TRANSFERRIN RECEPTOR ANTIBODIES AND METHODS OF USE" U.S. Pat. No. 9,708,406, filed May 20, 2014, "Anti-transferrin receptor antibodies and methods of use" | Apical domain and non-apical regions |
| (From Armagen) 8D3 | Lee et al. "Targeting Rat Anti-Mouse Transferrin Receptor Monoclonal Antibodies through Blood-Brain Barrier in Mouse" 2000, J Pharmacol. Exp. Ther., 292: 1048-1052. U.S. patent application 2010/077498, filed Sep. 11, 2008, entitled "COMPOSITIONS AND METHODS FOR BLOOD-BRAIN BARRIER DELIVERY IN THE MOUSE" | |
| OX26 | Haobam, B. et al. 2014. Rab17-mediated recycling endosomes contribute to autophagosome formation in response to Group A Streptococcus invasion. Cellular microbiology. 16: 1806-21. | |
| DF1513 | Ortiz-Zapater E et al. Trafficking of the human transferrin receptor in plant cells: effects of tyrphostin A23 and brefeldin A. Plant J 48:757-70 (2006). | |
| 1A1B2, 66IG10, MEM-189, JF0956, 29806, 1A1B2, TFRC/1818, 1E6, 66Ig10, TFRC/1059, Q1/71, 23D10, 13E4, TFRC/1149, ER-MP21, YTA74.4, BU54, 2B6, RI7 217 | Commercially available anti-transferrin receptor antibodies. | Novus Biologicals 8100 Southpark Way, A-8 Littleton CO 80120 |
| (From INSERM) BA120g | U.S. patent appplication 2011/0311544A1, filed Jun. 15, 2005, entitled "ANTI-CD71 MONOCLONAL ANTIBODIES AND USES THEREOF FOR TREATING MALIGNANT TUMOR CELLS" | Does not compete with OKT9 |
| LUCA31 | U.S. Pat. No. 7,572,895, filed Jun. 7, 2004, entitled "TRANSFERRIN RECEPTOR ANTIBODIES" | "LUCA31 epitope" |
| (Salk Institute) B3/25 T58/30 | Trowbridge, I. S. et al. "Anti-transferrin receptor monoclonal antibody and toxin-antibody conjugates affect growth of human tumour cells." Nature, 1981, volume 294, pages 171-173 | |
| R17 217.1.3, 5E9C11, OKT9 (BE0023 clone) | Commercially available anti-transferrin receptor antibodies. | BioXcell 10 Technology Dr., Suite 2B West Lebanon, NH 03784-1671 USA |
| BK19.9, B3/25, T56/14 and T58/1 | Gatter, K. C. et al. "Transferrin receptors in human tissues: their distribution and possible clinical relevance." J Clin Pathol. 1983 May; 36(5):539-45. | |

In some embodiments, the muscle-targeting agent is an anti-transferrin receptor antibody. In some embodiment, an anti-transferrin receptor antibody specifically binds to a transferrin protein having an amino acid sequence as disclosed herein. In some embodiments, an anti-transferrin receptor antibody may specifically bind to any extracellular epitope of a transferrin receptor or an epitope that becomes exposed to an antibody, including the apical domain, the transferrin binding domain, and the protease-like domain. In some embodiments, an anti-transferrin receptor antibody binds to an amino acid segment of a human or non-human primate transferrin receptor, as provided in SEQ ID Nos. 1-3 in the range of amino acids C89 to F760. In some embodiments, an anti-transferrin receptor antibody specifically binds with binding affinity of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. Anti-transferrin receptor antibodies used herein may be capable of competing for binding with other anti-transferrin receptor antibodies, e.g. OKT9, 8D3, that bind to transferrin receptor with $10^{-3}$ M, $10^{-4}$ M, $10^{-5}$ M, $10^{-6}$ M, $10^{-7}$ M, or less.

An example human transferrin receptor amino acid sequence, corresponding to NCBI sequence NP_003225.2 (transferrin receptor protein 1 isoform 1, *Homo sapiens*) is as follows:

(SEQ ID NO: 1)
MMDQARSAFSNLFGGEPLSYTRFSLARQVDGDNSHVEMKLAVDEEENADN
NTKANVTKPKRCSGSICYGTIAVIVFFLIGFMIGYLGYCKGVEPKTECER
LAGTESPVREEPGEDFPAARRLYWDDLKRKLSEKLDSTDFTGTIKLLNEN
SYVPREAGSQKDENLALYVENQFREFKLSKVWRDQHFVKIQVKDSAQNSV
IIVDKNGRLVYLVENPGGYVAYSKAATVTGKLVHANFGTKKDFEDLYTPV
NGSIVIVRAGKITFAEKVANAESLNAIGVLIYMDQTKFPIVNAELSFFGH
AHLGTGDPYTPGFPSFNHTQFPPSRSSGLPNIPVQTISRAAAEKLFGNME
GDCPSDWKTDSTCRMVTSESKNVKLTVSNVLKEIKILNIFGVIKGFVEPD
HYVVVGAQRDAWGPGAAKSGVGTALLLKLAQMFSDMVLKDGFQPSRSIIF
ASWSAGDFGSVGATEWLEGYLSSLHLKAFTYINLDKAVLGTSNFKVSASP
LLYTLIEKTMQNVKHPVTGQFLYQDSNWASKVEKLTLDNAAFPPLAYSGI
PAVSFCFCEDTDYPYLGTTMDTYKELIERIPELNKVARAAAEVAGQFVIK
LTHDVELNLDYERYNSQLLSFVRDLNQYRADIKEMGLSLQWLYSARGDFF
RATSRLTTDFGNAEKTDRFVMKKLNDRVMRVEYHFLSPYVSPKESPFRHV
FWGSGSHTLPALLENLKLRKQNNGAFNETLFRNQLALATWTIQGAANALS
GDVWDIDNEF

An example non-human primate transferrin receptor amino acid sequence, corresponding to NCBI sequence NP_001244232.1 (transferrin receptor protein 1, *Macaca mulatta*) is as follows:

(SEQ ID NO: 2)
MMDQARSAFSNLFGGEPLSYTRFSLARQVDGDNSHVEMKLGVDEEENTDN
NTKPNGTKPKRCGGNICYGTIAVIIFFLIGFMIGYLGYCKGVEPKTECER
LAGTESPAREEPEEDFPAAPRLYWDDLKRKLSEKLDTTDFTSTIKLLNEN
LYVPREAGSQKDENLALYIENQFREFKLSKVWRDQHFVKIQVKDSAQNSV
IIVDKNGGLVYLVENPGGYVAYSKAATVTGKLVHANFGTKKDFEDLDSPV
NGSIVIVRAGKITFAEKVANAESLNAIGVLIYMDQTKFPIVKADLSFFGH
AHLGTGDPYTPGFPSFNHTQFPPSQSSGLPNIPVQTISRAAAEKLFGNME
GDCPSDWKTDSTCKMVTSENKSVKLTVSNVLKETKILNIFGVIKGFVEPD
HYVVVGAQRDAWGPGAAKSSVGTALLLKLAQMFSDMVLKDGFQPSRSIIF
ASWSAGDFGSVGATEWLEGYLSSLHLKAFTYINLDKAVLGTSNFKVSASP
LLYTLIEKTMQDVKHPVTGRSLYQDSNWASKVEKLTLDNAAFPPLAYSGI
PAVSFCFCEDTDYPYLGTTMDTYKELVERIPELNKVARAAAEVAGQFVIK
LTHDTELNLDYERYNSQLLLFLRDLNQYRADVKEMGLSLQWLYSARGDFF
RATSRLTTDFRNAEKRDKFVMKKLNDRVMRVEYYFLSPYVSPKESPFRHV
FWGSGSHTLSALLESLKLRRQNNSAFNETLFRNQLALATWTIQGAANALS
GDVWDIDNEF

An example non-human primate transferrin receptor amino acid sequence, corresponding to NCBI sequence XP_005545315.1 (transferrin receptor protein 1, *Macaca fascicularis*) is as follows:

(SEQ ID NO: 3)
MMDQARSAFSNLFGGEPLSYTRFSLARQVDGDNSHVEMKLGVDEEENTDN
NTKANGTKPKRCGGNICYGTIAVIIFFLIGFMIGYLGYCKGVEPKTECER
LAGTESPAREEPEEDFPAAPRLYWDDLKRKLSEKLDTTDFTSTIKLLNEN
LYVPREAGSQKDENLALYIENQFREFKLSKVWRDQHFVKIQVKDSAQNSV
IIVDKNGGLVYLVENPGGYVAYSKAATVTGKLVHANFGTKKDFEDLDSPV
NGSIVIVRAGKITFAEKVANAESLNAIGVLIYMDQTKFPIVKADLSFFGH
AHLGTGDPYTPGFPSFNHTQFPPSQSSGLPNIPVQTISRAAAEKLFGNME
GDCPSDWKTDSTCKMVTSENKSVKLTVSNVLKETKILNIFGVIKGFVEPD
HYVVVGAQRDAWGPGAAKSSVGTALLLKLAQMFSDMVLKDGFQPSRSIIF
ASWSAGDFGSVGATEWLEGYLSSLHLKAFTYINLDKAVLGTSNFKVSASP
LLYTLIEKTMQDVKHPVTGRSLYQDSNWASKVEKLTLDNAAFPPLAYSGI
PAVSFCFCEDTDYPYLGTTMDTYKELVERIPELNKVARAAAEVAGQFVIK
LTHDTELNLDYERYNSQLLLFLRDLNQYRADVKEMGLSLQWLYSARGDFF
RATSRLTTDFRNAEKRDKFVMKKLNDRVMRVEYYFLSPYVSPKESPFRHV
FWGSGSHTLSALLESLKLRRQNNSAFNETLFRNQLALATWTIQGAANALS
GDVWDIDNEF.

An example mouse transferrin receptor amino acid sequence, corresponding to NCBI sequence NP_001344227.1 (transferrin receptor protein 1, *Mus musculus*) is as follows:

(SEQ ID NO: 4)
MMDQARSAFSNLFGGEPLSYTRFSLARQVDGDNSHVEMKLAADEEENADN
NMKASVRKPKRFNGRLCFAAIALVIFFLIGFMSGYLGYCKRVEQKEECVK
LAETEETDKSETMETEDVPTSSRLYWADLKTLLSEKLNSIEFADTIKQLS
QNTYTPREAGSQKDESLAYYIENQFHEFKFSKVWRDEHYVKIQVKSSIGQ
NMVTIVQSNGNLDPVESPEGYVAFSKPTEVSGKLVHANFGTKKDFEELSY
SVNGSLVIVRAGEITFAEKVANAQSFNAIGVLIYMDKNKFPVVEADLALF
GHAHLGTGDPYTPGFPSFNHTQFPPSQSSGLPNIPVQTISRAAAEKLFGK
MEGSCPARWNIDSSCKLELSQNQNVKLIVKNVLKERRILNIFGVIKGYEE
PDRYVVVGAQRDALGAGVAAKSSVGTGLLLKLAQVFSDMISKDGFRPSRS
IIFASWTAGDFGAVGATEWLEGYLSSLHLKAFTYINLDKVVLGTSNFKVS
ASPLLYTLMGKIMQDVKHPVDGKSLYRDSNWISKVEKLSFDNAAYPFLAY

```
SGIPAVSFCFCEDADYPYLGTRLDTYEALTQKVPQLNQMVRTAAEVAGQL

IIKLTHDVELNLDYEMYNSKLLSFMKDLNQFKTDIRDMGLSLQWLYSARG

DYFRATSRLTTDFHNAEKTNRFVMREINDRIMKVEYHFLSPYVSPRESPF

RHIFWGSGSHTLSALVENLKLRQKNITAFNETLFRNQLALATWTIQGVAN

ALSGDIWNIDNEF
```

In some embodiments, an anti-transferrin receptor antibody binds to an amino acid segment of the receptor as follows:

```
                                          (SEQ ID NO: 5)
FVKIQVKDSAQNSVIIVDKNGRLVYLVENPGGYVAYSKAATVTGKLVHA

NFGTKKDFEDLYTPVNGSIVIVRAGKITFAEKVANAESLNAIGVLIYMD

QTKFPIVNAELSFFGHAHLGTGDPYTPGFPSFNHTQFPPSRSSGLPNIP

VQTISRAAAEKLFGNMEGDCPSDWKTDSTCRMVTSESKNVKLTVSNVLK

E
``` and does not inhibit the binding interactions between transferrin receptors and transferrin and/or human hemochromatosis protein (also known as HFE).

Appropriate methodologies may be used to obtain and/or produce antibodies, antibody fragments, or antigen-binding agents, e.g., through the use of recombinant DNA protocols. In some embodiments, an antibody may also be produced through the generation of hybridomas (see, e.g., Kohler, G and Milstein, C. "Continuous cultures of fused cells secreting antibody of predefined specificity" Nature, 1975, 256: 495-497). The antigen-of-interest may be used as the immunogen in any form or entity, e.g., recombinant or a naturally occurring form or entity. Hybridomas are screened using standard methods, e.g. ELISA screening, to find at least one hybridoma that produces an antibody that targets a particular antigen. Antibodies may also be produced through screening of protein expression libraries that express antibodies, e.g., phage display libraries. Phage display library design may also be used, in some embodiments, (see, e.g. U.S. Pat. No. 5,223,409, filed Mar. 1, 1991, "Directed evolution of novel binding proteins"; WO 1992/18619, filed Apr. 10, 1992, "Heterodimeric receptor libraries using phagemids"; WO 1991/17271, filed May 1, 1991, "Recombinant library screening methods"; WO 1992/20791, filed May 15, 1992, "Methods for producing members of specific binding pairs"; WO 1992/15679, filed Feb. 28, 1992, and "Improved epitope displaying phage"). In some embodiments, an antigen-of-interest may be used to immunize a non-human animal, e.g., a rodent or a goat. In some embodiments, an antibody is then obtained from the non-human animal, and may be optionally modified using a number of methodologies, e.g., using recombinant DNA techniques. Additional examples of antibody production and methodologies are known in the art (see, e.g. Harlow et al. "Antibodies: A Laboratory Manual", Cold Spring Harbor Laboratory, 1988).

In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway, e.g. a glycosyltransferase. In some embodiments, an antibody is functionalized with sugar or carbohydrate molecules as described in International Patent Application Publication WO2014065661, published on May 1, 2014, entitled, "Modified antibody, antibody-conjugate and process for the preparation thereof".

Some aspects of the disclosure provide proteins that bind to transferrin receptor (e.g., an extracellular portion of the transferrin receptor). In some embodiments, transferrin receptor antibodies provided herein bind specifically to transferrin receptor (e.g., human transferrin receptor). Transferrin receptors are internalizing cell surface receptors that transport transferrin across the cellular membrane and participate in the regulation and homeostasis of intracellular iron levels. In some embodiments, transferrin receptor antibodies provided herein bind specifically to transferrin receptor from human, non-human primates, mouse, rat, etc. In some embodiments, transferrin receptor antibodies provided herein bind to human transferrin receptor. In some embodiments, transferrin receptor antibodies provided herein specifically bind to human transferrin receptor. In some embodiments, transferrin receptor antibodies provided herein bind to an apical domain of human transferrin receptor. In some embodiments, transferrin receptor antibodies provided herein specifically bind to an apical domain of human transferrin receptor.

In some embodiments, transferrin receptor antibodies of the present disclosure include one or more of the CDR-H (e.g., CDR-H1, CDR-H2, and CDR-H3) amino acid sequences from any one of the anti-transferrin receptor antibodies selected from Table 1. In some embodiments, transferrin receptor antibodies include the CDR-H1, CDR-H2, and CDR-H3 as provided for any one of the anti-transferrin receptor antibodies selected from Table 1. In some embodiments, anti-transferrin receptor antibodies include the CDR-L1, CDR-L2, and CDR-L3 as provided for any one of the anti-transferrin receptor antibodies selected from Table 1. In some embodiments, anti-transferrin antibodies include the CDR-H1, CDR-H2, CDR-H3, CDR-L1, CDR-L2, and CDR-L3 as provided for any one of the anti-transferrin receptor antibodies selected from Table 1. The disclosure also includes any nucleic acid sequence that encodes a molecule comprising a CDR-H1, CDR-H2, CDR-H3, CDR-L1, CDR-L2, or CDR-L3 as provided for any one of the anti-transferrin receptor antibodies selected from Table 1. In some embodiments, antibody heavy and light chain CDR3 domains may play a particularly important role in the binding specificity/affinity of an antibody for an antigen. Accordingly, anti-transferrin receptor antibodies of the disclosure may include at least the heavy and/or light chain CDR3s of any one of the anti-transferrin receptor antibodies selected from Table 1.

In some examples, any of the anti-transferrin receptor antibodies of the disclosure have one or more CDR (e.g., CDR-H or CDR-L) sequences substantially similar to any of the CDR-H1, CDR-H2, CDR-H3, CDR-L1, CDR-L2, and/or CDR-L3 sequences from one of the anti-transferrin receptor antibodies selected from Table 1. In some embodiments, the position of one or more CDRs along the VH (e.g., CDR-H1, CDR-H2, or CDR-H3) and/or VL (e.g., CDR-L1, CDR-L2, or CDR-L3) region of an antibody described herein can vary by one, two, three, four, five, or six amino acid positions so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any antibody described herein can vary by shifting the N-terminal and/or C-terminal boundary of the CDR by one, two, three, four, five, or six amino acids, relative to the CDR position of any one of the antibodies described herein, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the VH (e.g., CDR-H1, CDR-H2, or CDR-H3) and/or VL (e.g., CDR-L1, CDR-L2, or CDR-L3) region of an antibody described herein can vary (e.g., be shorter or longer) by one, two, three, four, five, or more amino acids, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived).

Accordingly, in some embodiments, a CDR-L1, CDR-L2, CDR-L3, CDR-H1, CDR-H2, and/or CDR-H3 described herein may be one, two, three, four, five or more amino acids shorter than one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, a CDR-L1, CDR-L2, CDR-L3, CDR-H1, CDR-H2, and/or CDR-H3 described herein may be one, two, three, four, five or more amino acids longer than one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or CDR-H3 described herein can be extended by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or CDR-H3 described herein can be extended by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or CDR-H3 described herein can be shortened by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or CDR-H3 described herein can be shortened by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). Any method can be used to ascertain whether immunospecific binding to transferrin receptor (e.g., human transferrin receptor) is maintained, for example, using binding assays and conditions described in the art.

In some examples, any of the anti-transferrin receptor antibodies of the disclosure have one or more CDR (e.g., CDR-H or CDR-L) sequences substantially similar to any one of the anti-transferrin receptor antibodies selected from Table 1. For example, the antibodies may include one or more CDR sequence(s) from any of the anti-transferrin receptor antibodies selected from Table 1 containing up to 5, 4, 3, 2, or 1 amino acid residue variations as compared to the corresponding CDR region in any one of the CDRs provided herein (e.g., CDRs from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, any of the amino acid variations in any of the CDRs provided herein may be conservative variations. Conservative variations can be introduced into the CDRs at positions where the residues are not likely to be involved in interacting with a transferrin receptor protein (e.g., a human transferrin receptor protein), for example, as determined based on a crystal structure. Some aspects of the disclosure provide transferrin receptor antibodies that comprise one or more of the heavy chain variable (VH) and/or light chain variable (VL) domains provided herein. In some embodiments, any of the VH domains provided herein include one or more of the CDR-H sequences (e.g., CDR-H1, CDR-H2, and CDR-H3) provided herein, for example, any of the CDR-H sequences provided in any one of the anti-transferrin receptor antibodies selected from Table 1. In some embodiments, any of the VL domains provided herein include one or more of the CDR-L sequences (e.g., CDR-L1, CDR-L2, and CDR-L3) provided herein, for example, any of the CDR-L sequences provided in any one of the anti-transferrin receptor antibodies selected from Table 1.

In some embodiments, anti-transferrin receptor antibodies of the disclosure include any antibody that includes a heavy chain variable domain and/or a light chain variable domain of any anti-transferrin receptor antibody, such as any one of the anti-transferrin receptor antibodies selected from Table 1. In some embodiments, anti-transferrin receptor antibodies of the disclosure include any antibody that includes the heavy chain variable and light chain variable pairs of any anti-transferrin receptor antibody, such as any one of the anti-transferrin receptor antibodies selected from Table 1.

Aspects of the disclosure provide anti-transferrin receptor antibodies having a heavy chain variable (VH) and/or a light chain variable (VL) domain amino acid sequence homologous to any of those described herein. In some embodiments, the anti-transferrin receptor antibody comprises a heavy chain variable sequence or a light chain variable sequence that is at least 75% (e.g., 80%, 85%, 90%, 95%, 98%, or 99%) identical to the heavy chain variable sequence and/or any light chain variable sequence of any anti-transferrin receptor antibody, such as any one of the anti-transferrin receptor antibodies selected from Table 1. In some embodiments, the homologous heavy chain variable and/or a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein. In some embodiments, any of the anti-transferrin receptor antibodies provided herein comprise a heavy chain variable sequence and a light chain variable sequence that comprises a framework sequence that is at least 75%, 80%, 85%, 90%, 95%, 98%, or 99% identical to the framework sequence of any anti-transferrin receptor antibody, such as any one of the anti-transferrin receptor antibodies selected from Table 1.

In some embodiments, an anti-transferrin receptor antibody, which specifically binds to transferrin receptor (e.g., human transferrin receptor), comprises a light chain variable VL domain comprising any of the CDR-L domains (CDR-L1, CDR-L2, and CDR-L3), or CDR-L domain variants provided herein, of any of the anti-transferrin receptor antibodies selected from Table 1. In some embodiments, an anti-transferrin receptor antibody, which specifically binds to transferrin receptor (e.g., human transferrin receptor), comprises a light chain variable VL domain comprising the CDR-L1, the CDR-L2, and the CDR-L3 of any anti-transferrin receptor antibody, such as any one of the anti-transferrin receptor antibodies selected from Table 1. In some embodiments, the anti-transferrin receptor antibody comprises a light chain variable (VL) region sequence comprising one, two, three or four of the framework regions of the light chain variable region sequence of any anti-transferrin receptor antibody, such as any one of the anti-transferrin receptor antibodies selected from Table 1. In some embodiments, the anti-transferrin receptor antibody comprises one, two, three or four of the framework regions of a light chain variable region sequence which is at least 75%, 80%, 85%, 90%, 95%, or 100% identical to one, two, three or four of the framework regions of the light chain variable region sequence of any anti-transferrin receptor antibody, such as any one of the anti-transferrin receptor antibodies selected from Table 1. In some embodiments, the light chain variable framework region that is derived from said amino acid sequence consists of said amino acid sequence but for the presence of up to 10 amino acid substitutions, deletions, and/or insertions, preferably up to 10 amino acid substitutions. In some embodiments, the light chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human light chain variable framework region.

In some embodiments, an anti-transferrin receptor antibody that specifically binds to transferrin receptor comprises the CDR-L1, the CDR-L2, and the CDR-L3 of any anti-transferrin receptor antibody, such as any one of the anti-transferrin receptor antibodies selected from Table 1. In some embodiments, the antibody further comprises one, two, three or all four VL framework regions derived from the VL of a human or primate antibody. The primate or human light chain framework region of the antibody selected for use with the light chain CDR sequences described herein, can have, for example, at least 70% (e.g., at least 75%, 80%, 85%, 90%, 95%, 98%, or at least 99%) identity with a light chain framework region of a non-human parent antibody. The primate or human antibody selected can have the same or substantially the same number of amino acids in its light chain complementarity determining regions to that of the light chain complementarity determining regions of any of the antibodies provided herein, e.g., any of the anti-transferrin receptor antibodies selected from Table 1. In some embodiments, the primate or human light chain framework region amino acid residues are from a natural primate or human antibody light chain framework region having at least 75% identity, at least 80% identity, at least 85% identity, at least 90% identity, at least 95% identity, at least 98% identity, at least 99% (or more) identity with the light chain framework regions of any anti-transferrin receptor antibody, such as any one of the anti-transferrin receptor antibodies selected from Table 1. In some embodiments, an anti-transferrin receptor antibody further comprises one, two, three or all four VL framework regions derived from a human light chain variable kappa subfamily. In some embodiments, an anti-transferrin receptor antibody further comprises one, two, three or all four VL framework regions derived from a human light chain variable lambda subfamily.

In some embodiments, any of the anti-transferrin receptor antibodies provided herein comprise a light chain variable domain that further comprises a light chain constant region. In some embodiments, the light chain constant region is a kappa, or a lambda light chain constant region. In some embodiments, the kappa or lambda light chain constant region is from a mammal, e.g., from a human, monkey, rat, or mouse. In some embodiments, the light chain constant region is a human kappa light chain constant region. In some embodiments, the light chain constant region is a human lambda light chain constant region. It should be appreciated that any of the light chain constant regions provided herein may be variants of any of the light chain constant regions provided herein. In some embodiments, the light chain constant region comprises an amino acid sequence that is at least 75%, 80%, 85%, 90%, 95%, 98%, or 99% identical to any of the light chain constant regions of any anti-transferrin receptor antibody, such as any one of the anti-transferrin receptor antibodies selected from Table 1.

In some embodiments, the anti-transferrin receptor antibody is any anti-transferrin receptor antibody, such as any one of the anti-transferrin receptor antibodies selected from Table 1.

In some embodiments, an anti-transferrin receptor antibody comprises a VL domain comprising the amino acid sequence of any anti-transferrin receptor antibody, such as any one of the anti-transferrin receptor antibodies selected from Table 1, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In some embodiments, an anti-transferrin receptor antibody comprises any of the VL domains, or VL domain variants, and any of the VH domains, or VH domain variants, wherein the VL and VH domains, or variants thereof, are from the same antibody clone, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra.

In some embodiments, an antibody of the disclosure can bind to a target antigen (e.g., transferrin receptor) with relatively high affinity, e.g., with a $K_D$ less than $10^{-6}$ M, $10^{-7}$ M, $10^{-8}$ M, $10^{-9}$ M, $10^{-10}$ M, $10^{-11}$ M or lower. For example, anti-transferrin receptor antibodies can bind to a transferrin receptor protein (e.g., human transferrin receptor) with an affinity between 5 pM and 500 nM, e.g., between 50 pM and 100 nM, e.g., between 500 pM and 50 nM. The disclosure also includes antibodies that compete with any of the antibodies described herein for binding to a transferrin receptor protein (e.g., human transferrin receptor) and that have an affinity of 50 nM or lower (e.g., 20 nM or lower, 10 nM or lower, 500 pM or lower, 50 pM or lower, or 5 pM or lower). The affinity and binding kinetics of the anti-transferrin receptor antibody can be tested using any suitable method including but not limited to biosensor technology (e.g., OCTET or BIACORE).

In some embodiments, an antibody of the disclosure can bind to a target antigen (e.g., transferrin receptor) with relatively high affinity, e.g., with a $K_D$ less than $10^{-6}$ M, $10^{-7}$ M, $10^{-8}$ M, $10^{-9}$ M, $10^{-10}$ M, $10^{-11}$ M or lower. For example, anti-transferrin receptor antibodies can bind to a transferrin receptor protein (e.g., human transferrin receptor) with an affinity between 5 pM and 500 nM, e.g., between 50 pM and 100 nM, e.g., between 500 pM and 50 nM. The disclosure also includes antibodies that compete with any of the antibodies described herein for binding to a transferrin receptor protein (e.g., human transferrin receptor) and that have an affinity of 50 nM or lower (e.g., 20 nM or lower, 10 nM or lower, 500 pM or lower, 50 pM or lower, or 5 pM or lower). The affinity and binding kinetics of the anti-transferrin receptor antibody can be tested using any suitable method including but not limited to biosensor technology (e.g., OCTET or BIACORE).

In some embodiments, the muscle-targeting agent is a transferrin receptor antibody (e.g., the antibody and variants thereof as described in International Application Publication WO 2016/081643, incorporated herein by reference).

The heavy chain and light chain CDRs of the antibody according to different definition systems are provided in Table 1.1. The different definition systems, e.g., the Kabat definition, the Chothia definition, and/or the contact definition have been described. See, e.g., (e.g., Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, A1-lazikani et al (1997) J. Molec. Biol. 273: 927-948; and Almagro, J. Mol. Recognit. 17:132-143 (2004). See also hgmp.mrc.ac.uk and bioinf.org.uk/abs).

TABLE 1

Heavy chain and light chain CDRs of a mouse transferrin receptor antibody

| CDRs | Kabat | Chothia | Contact |
|---|---|---|---|
| CDR-H1 | SYWMH (SEQ ID NO: 17) | GYTFTSY (SEQ ID NO: 23) | TSYWMH (SEQ ID NO: 25) |
| CDR-H2 | EINPTNGRT NYIEKFKS (SEQ ID NO: 18) | NPTNG (SEQ ID NO: 24) | RWIGEINPTNGRTN (SEQ ID NO: 26) |
| CDR-H3 | GTRAYHY (SEQ ID NO: 19) | GTRAYHY (SEQ ID NO: 19) | ARGTRA (SEQ ID NO: 27) |
| CDR-L1 | RASDNLYSNLA (SEQ ID NO: 20) | RASDNLYSNLA (SEQ ID NO: 20) | YSNLAWY (SEQ ID NO: 28) |
| CDR-L2 | DATNLAD (SEQ ID NO: 21) | DATNLAD (SEQ ID NO: 21) | LLVYDATNLA (SEQ ID NO: 29) |
| CDR-L3 | QHFWGTPLT (SEQ ID NO: 22) | QHFWGTPLT (SEQ ID NO: 22) | QHFWGTPL (SEQ ID NO: 30) |

The heavy chain variable domain (VH) and light chain variable domain sequences are also provided:

VH (SEQ ID NO: 33)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSS

VL (SEQ ID NO: 34)
DIQMTQSPASLSVSVGETVTITCRASDNLYSNLAWYQQKQGKSPQLLVYD

ATNLADGVPSRFSGSGSGTQYSLKINSLQSEDFGTYYCQHFWGTPLTFGA

GTKLELK

In some embodiments, the transferrin receptor antibody of the present disclosure comprises a CDR-H1, a CDR-H2, and a CDR-H3 that are the same as the CDR-H1, CDR-H2, and CDR-H3 shown in Table 1.1. Alternatively or in addition, the transferrin receptor antibody of the present disclosure comprises a CDR-L1, a CDR-L2, and a CDR-L3 that are the same as the CDR-L1, CDR-L2, and CDR-L3 shown in Table 1.1.

In some embodiments, the transferrin receptor antibody of the present disclosure comprises a CDR-H1, a CDR-H2, and a CDR-H3, which collectively contains no more than 5 amino acid variations (e.g., no more than 5, 4, 3, 2, or 1 amino acid variation) as compared with the CDR-H1, CDR-H2, and CDR-H3 as shown in Table 1.1. "Collectively" means that the total number of amino acid variations in all of the three heavy chain CDRs is within the defined range. Alternatively or in addition, the transferrin receptor antibody of the present disclosure may comprise a CDR-L1, a CDR-L2, and a CDR-L3, which collectively contains no more than 5 amino acid variations (e.g., no more than 5, 4, 3, 2 or 1 amino acid variation) as compared with the CDR-L1, CDR-L2, and CDR-L3 as shown in Table 1.1.

In some embodiments, the transferrin receptor antibody of the present disclosure comprises a CDR-H1, a CDR-H2, and a CDR-H3, at least one of which contains no more than 3 amino acid variations (e.g., no more than 3, 2, or 1 amino acid variation) as compared with the counterpart heavy chain CDR as shown in Table 1.1. Alternatively or in addition, the transferrin receptor antibody of the present disclosure may comprise CDR-L1, a CDR-L2, and a CDR-L3, at least one of which contains no more than 3 amino acid variations (e.g., no more than 3, 2, or 1 amino acid variation) as compared with the counterpart light chain CDR as shown in Table 1.1.

In some embodiments, the transferrin receptor antibody of the present disclosure comprises a CDR-L3, which contains no more than 3 amino acid variations (e.g., no more than 3, 2, or 1 amino acid variation) as compared with the CDR-L3 as shown in Table 1.1. In some embodiments, the transferrin receptor antibody of the present disclosure comprises a CDR-L3 containing one amino acid variation as compared with the CDR-L3 as shown in Table 1.1. In some embodiments, the transferrin receptor antibody of the present disclosure comprises a CDR-L3 of QHFAGTPLT (SEQ ID NO: 31 according to the Kabat and Chothia definition system) or QHFAGTPL (SEQ ID NO: 32 according to the Contact definition system). In some embodiments, the transferrin receptor antibody of the present disclosure comprises a CDR-H1, a CDR-H2, a CDR-H3, a CDR-L1 and a CDR-L2 that are the same as the CDR-H1, CDR-H2, and CDR-H3 shown in Table 1.1, and comprises a CDR-L3 of QHFAGTPLT (SEQ ID NO: 31 according to the Kabat and Chothia definition system) or QHFAGTPL (SEQ ID NO: 32 according to the Contact definition system).

In some embodiments, the transferrin receptor antibody of the present disclosure comprises heavy chain CDRs that collectively are at least 80% (e.g., 80%, 85%, 90%, 95%, or 98%) identical to the heavy chain CDRs as shown in Table 1.1. Alternatively or in addition, the transferrin receptor antibody of the present disclosure comprises light chain CDRs that collectively are at least 80% (e.g., 80%, 85%, 90%, 95%, or 98%) identical to the light chain CDRs as shown in Table 1.1.

In some embodiments, the transferrin receptor antibody of the present disclosure comprises a VH comprising the amino acid sequence of SEQ ID NO: 33. Alternatively or in addition, the transferrin receptor antibody of the present disclosure comprises a VL comprising the amino acid sequence of SEQ ID NO: 34.

In some embodiments, the transferrin receptor antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 33. Alternatively or in addition, the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 34.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 33. Alternatively or in addition, the transferrin receptor antibody of the present disclosure comprises a VL comprising an amino acid sequence that is at least 80% (e.g., 80%, 85%, 90%, 95%, or 98%) identical to the VL as set forth in SEQ ID NO: 34.

In some embodiments, the transferrin receptor antibody of the present disclosure is a humanized antibody (e.g., a humanized variant of an antibody). In some embodiments, the transferrin receptor antibody of the present disclosure comprises a CDR-H1, a CDR-H2, a CDR-H3, a CDR-L1, a CDR-L2, and a CDR-L3 that are the same as the CDR-H1, CDR-H2, and CDR-H3 shown in Table 1.1, and comprises a humanized heavy chain variable region and/or a humanized light chain variable region.

Humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some embodiments, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs derived from one or more CDRs from the original antibody. Humanized antibodies may also involve affinity maturation.

In some embodiments, humanization is achieved by grafting the CDRs (e.g., as shown in Table 1.1) into the IGKV1-NL1*01 and IGHV1-3*01 human variable domains. In some embodiments, the transferrin receptor antibody of the present disclosure is a humanized variant comprising one or more amino acid substitutions at positions 9, 13, 17, 18, 40, 45, and 70 as compared with the VL as set forth in SEQ ID NO: 34, and/or one or more amino acid substitutions at positions 1, 5, 7, 11, 12, 20, 38, 40, 44, 66, 75, 81, 83, 87, and 108 as compared with the VH as set forth in SEQ ID NO: 33. In some embodiments, the transferrin receptor antibody of the present disclosure is a humanized variant comprising amino acid substitutions at all of positions 9, 13, 17, 18, 40, 45, and 70 as compared with the VL as set forth in SEQ ID NO: 34, and/or amino acid substitutions at all of positions 1, 5, 7, 11, 12, 20, 38, 40, 44, 66, 75, 81, 83, 87, and 108 as compared with the VH as set forth in SEQ ID NO: 33.

In some embodiments, the transferrin receptor antibody of the present disclosure is a humanized antibody and contains the residues at positions 43 and 48 of the VL as set forth in SEQ ID NO: 34. Alternatively or in addition, the transferrin receptor antibody of the present disclosure is a humanized antibody and contains the residues at positions 48, 67, 69, 71, and 73 of the VH as set forth in SEQ ID NO: 33.

The VH and VL amino acid sequences of an example humanized antibody that may be used in accordance with the present disclosure are provided:

Humanized VH

```
                                           (SEQ ID NO: 35)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT

RAYHYWGQGTMVTVSS
```

Humanized VL

```
                                           (SEQ ID NO: 36)
DIQMTQSPSSLSASVGDRVTITCRASDNLYSNLAWYQQKPGKSPKLLVYD

ATNLADGVPSRFSGSGSGTDYSLKINSLQSEDFGTYYCQHFWGTPLTFGA

GTKLELK
```

In some embodiments, the transferrin receptor antibody of the present disclosure comprises a VH comprising the amino acid sequence of SEQ ID NO: 35. Alternatively or in addition, the transferrin receptor antibody of the present disclosure comprises a VL comprising the amino acid sequence of SEQ ID NO: 36.

In some embodiments, the transferrin receptor antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 35. Alternatively or in addition, the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 36.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 35. Alternatively or in addition, the transferrin receptor antibody of the present disclosure comprises a VL comprising an amino acid sequence that is at least 80% (e.g., 80%, 85%, 90%, 95%, or 98%) identical to the VL as set forth in SEQ ID NO: 36.

In some embodiments, the transferrin receptor antibody of the present disclosure is a humanized variant comprising amino acid substitutions at one or more of positions 43 and 48 as compared with the VL as set forth in SEQ ID NO: 34, and/or amino acid substitutions at one or more of positions 48, 67, 69, 71, and 73 as compared with the VH as set forth in SEQ ID NO: 33. In some embodiments, the transferrin receptor antibody of the present disclosure is a humanized variant comprising a S43A and/or a V48L mutation as compared with the VL as set forth in SEQ ID NO: 34, and/or one or more of A67V, L69I, V71R, and K73T mutations as compared with the VH as set forth in SEQ ID NO: 33

In some embodiments, the transferrin receptor antibody of the present disclosure is a humanized variant comprising amino acid substitutions at one or more of positions 9, 13, 17, 18, 40, 43, 48, 45, and 70 as compared with the VL as set forth in SEQ ID NO: 34, and/or amino acid substitutions at one or more of positions 1, 5, 7, 11, 12, 20, 38, 40, 44, 48, 66, 67, 69, 71, 73, 75, 81, 83, 87, and 108 as compared with the VH as set forth in SEQ ID NO: 33.

In some embodiments, the transferrin receptor antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the transferrin receptor antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the heavy chain of any of the transferrin receptor antibodies as described herein may comprises a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4. An exemplary human IgG1 constant region is given below:

```
                                           (SEQ ID NO: 37)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

In some embodiments, the light chain of any of the transferrin receptor antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

(SEQ ID NO: 38)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCP

Other antibody heavy and light chain constant regions are well known in the art, e.g., those provided in the IMGT database (imgt.org) or at vbase2.org/vbstat.php., both of which are incorporated by reference herein.

Exemplary heavy chain and light chain amino acid sequences of the transferrin receptor antibodies described are provided below:

Heavy Chain (VH+human IgG1 constant region)

(SEQ ID NO: 39)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Light Chain (VL+kappa light chain)

(SEQ ID NO: 40)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP

Heavy Chain (humanized VH+human IgG1 constant region)

(SEQ ID NO: 41)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT

RAYHYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Light Chain (humanized VL+kappa light chain)

(SEQ ID NO: 42)
DIQMTQSPSSLSASVGDRVTITCRASDNLYSNLAWYQQKPGKSPKLLVYD

ATNLADGVPSRFSGSGSGTDYSLKINSLQSEDFGTYYCQHFWGTPLTFGA

GTKLELKASTKGPSVFPLAPSSKSTSGGTAALGCLVKDYFPEPVTVSWNS

GALTSGVHTFPAVLQSSGLYSLSSVVTVPSSSLGTQTYICNVNHKPSNTK

VDKKVEPKSCDKTHTCP

In some embodiments, the transferrin receptor antibody described herein comprises a heavy chain comprising an amino acid sequence that is at least 80% (e.g., 80%, 85%, 90%, 95%, or 98%) identical to SEQ ID NO: 39. Alternatively or in addition, the transferrin receptor antibody described herein comprises a light chain comprising an amino acid sequence that is at least 80% (e.g., 80%, 85%, 90%, 95%, or 98%) identical to SEQ ID NO: 40. In some embodiments, the transferrin receptor antibody described herein comprises a heavy chain comprising the amino acid sequence of SEQ ID NO: 39. Alternatively or in addition, the transferrin receptor antibody described herein comprises a light chain comprising the amino acid sequence of SEQ ID NO: 40.

In some embodiments, the transferrin receptor antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in SEQ ID NO: 39. Alternatively or in addition, the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in SEQ ID NO: 40.

In some embodiments, the transferrin receptor antibody described herein comprises a heavy chain comprising an amino acid sequence that is at least 80% (e.g., 80%, 85%, 90%, 95%, or 98%) identical to SEQ ID NO: 41. Alternatively or in addition, the transferrin receptor antibody described herein comprises a light chain comprising an amino acid sequence that is at least 80% (e.g., 80%, 85%, 90%, 95%, or 98%) identical to SEQ ID NO: 42. In some embodiments, the transferrin receptor antibody described herein comprises a heavy chain comprising the amino acid sequence of SEQ ID NO: 41. Alternatively or in addition, the transferrin receptor antibody described herein comprises a light chain comprising the amino acid sequence of SEQ ID NO: 42.

In some embodiments, the transferrin receptor antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain of humanized antibody as set forth in SEQ ID NO: 39. Alternatively or in addition, the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain of humanized antibody as set forth in SEQ ID NO: 40.

In some embodiments, the transferrin receptor antibody is an antigen binding fragment (FAB) of an intact antibody (full-length antibody). Antigen binding fragment of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments. Exemplary FABs amino acid sequences of the transferrin receptor antibodies described herein are provided below:

Heavy Chain FAB (VH+a portion of human IgG1 constant region)

(SEQ ID NO: 43)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP

Heavy Chain FAB (humanized VH+a portion of human IgG1 constant region)

(SEQ ID NO: 44)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT

RAYHYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP

The transferrin receptor antibodies described herein can be in any antibody form, including, but not limited to, intact (i.e., full-length) antibodies, antigen-binding fragments thereof (such as Fab, Fab', F(ab')2, Fv), single chain antibodies, bi-specific antibodies, or nanobodies. In some embodiments, the transferrin receptor antibody described herein is a scFv. In some embodiments, the transferrin receptor antibody described herein is a scFv-Fab (e.g., scFv fused to a portion of a constant region). In some embodiments, the transferrin receptor antibody described herein is a scFv fused to a constant region (e.g., human IgG1 constant region as set forth in SEQ ID NO: 39).

b. Other Muscle-Targeting Antibodies

In some embodiments, the muscle-targeting antibody is an antibody that specifically binds hemojuvelin, caveolin-3, Duchenne muscular dystrophy peptide, myosin IIb, or CD63. In some embodiments, the muscle-targeting antibody is an antibody that specifically binds a myogenic precursor protein. Exemplary myogenic precursor proteins include, without limitation, ABCG2, M-Cadherin/Cadherin-15, Caveolin-1, CD34, FoxK1, Integrin alpha 7, Integrin alpha 7 beta 1, MYF-5, MyoD, Myogenin, NCAM-1/CD56, Pax3, Pax7, and Pax9. In some embodiments, the muscle-targeting antibody is an antibody that specifically binds a skeletal muscle protein. Exemplary skeletal muscle proteins include, without limitation, alpha-Sarcoglycan, beta-Sarcoglycan, Calpain Inhibitors, Creatine Kinase MM/CKMM, eIF5A, Enolase 2/Neuron-specific Enolase, epsilon-Sarcoglycan, FABP3/H-FABP, GDF-8/Myostatin, GDF-11/GDF-8, Integrin alpha 7, Integrin alpha 7 beta 1, Integrin beta 1/CD29, MCAM/CD146, MyoD, Myogenin, Myosin Light Chain Kinase Inhibitors, NCAM-1/CD56, and Troponin I. In some embodiments, the muscle-targeting antibody is an antibody that specifically binds a smooth muscle protein. Exemplary smooth muscle proteins include, without limitation, alpha-Smooth Muscle Actin, VE-Cadherin, Caldesmon/CALD1, Calponin 1, Desmin, Histamine H2 R, Motilin R/GPR38, Transgelin/TAGLN, and Vimentin. However, it should be appreciated that antibodies to additional targets are within the scope of this disclosure and the exemplary lists of targets provided herein are not meant to be limiting.

c. Antibody Features/Alterations

In some embodiments, conservative mutations can be introduced into antibody sequences (e.g., CDRs or framework sequences) at positions where the residues are not likely to be involved in interacting with a target antigen (e.g., transferrin receptor), for example, as determined based on a crystal structure. In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-transferrin receptor antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-transferrin receptor antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of a muscle-targeting antibody described herein can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or to increase the affinity of the antibody for an Fcy receptor. This approach is described further in International Publication No. WO 00/42072.

In some embodiments, the heavy and/or light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind transferrin receptor, such that the variant, CDR-grafted, chimeric, humanized, or composite antibody has at least 50%, at least 60%, at least 70%, at least 80%, at least 90%, at least 95% or more binding to transferrin receptor relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

As provided herein, antibodies of this disclosure may optionally comprise constant regions or parts thereof. For example, a VL domain may be attached at its C-terminal end to a light chain constant domain like Cκ or Cλ. Similarly, a VH domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include VH and VL domains, or an antigen binding portion thereof, combined with any suitable constant regions.

ii. Muscle-Targeting Peptides

Some aspects of the disclosure provide muscle-targeting peptides as muscle-targeting agents. Short peptide sequences (e.g., peptide sequences of 5-20 amino acids in length) that bind to specific cell types have been described. For example, cell-targeting peptides have been described in Vines e., et al., A. "Cell-penetrating and cell-targeting peptides in drug delivery" *Biochim Biophys Acta* 2008, 1786: 126-38; Jarver P., et al., "In vivo biodistribution and efficacy of peptide mediated delivery" *Trends Pharmacol Sci* 2010; 31: 528-35; Samoylova T. I., et al., "Elucidation of muscle-binding peptides by phage display screening" *Muscle Nerve* 1999; 22: 460-6; U.S. Pat. No. 6,329,501, issued on Dec. 11, 2001, entitled "METHODS AND COMPOSITIONS FOR TARGETING COMPOUNDS TO MUSCLE"; and Samoylov A. M., et al., "Recognition of cell-specific binding of phage display derived peptides using an acoustic wave sensor." *Biomol Eng* 2002; 18: 269-72; the entire contents of each of which are incorporated herein by reference. By designing peptides to interact with specific cell surface antigens (e.g., receptors), selectivity for a desired tissue, e.g., muscle, can be achieved. Skeletal muscle-targeting has been investigated and a range of molecular payloads are able to be delivered. These approaches may have high selectivity for muscle tissue without many of the practical disadvantages of a large antibody or viral particle. Accordingly, in some embodiments, the muscle-targeting agent is a muscle-targeting peptide that is from 4 to 50 amino acids in length. In some embodiments, the muscle-targeting peptide is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. Muscle-targeting peptides can be generated using any of several methods, such as phage display.

In some embodiments, a muscle-targeting peptide may bind to an internalizing cell surface receptor that is overexpressed or relatively highly expressed in muscle cells, e.g. a transferrin receptor, compared with certain other cells. In some embodiments, a muscle-targeting peptide may target, e.g., bind to, a transferrin receptor. In some embodiments, a peptide that targets a transferrin receptor may comprise a segment of a naturally occurring ligand, e.g., transferrin. In some embodiments, a peptide that targets a transferrin receptor is as described in U.S. Pat. No. 6,743,893, filed Nov. 30, 2000, "RECEPTOR-MEDIATED UPTAKE OF PEPTIDES THAT BIND THE HUMAN TRANSFERRIN RECEPTOR". In some embodiments, a peptide that targets a transferrin receptor is as described in Kawamoto, M. et al, "A novel transferrin receptor-targeted hybrid peptide disintegrates cancer cell membrane to induce rapid killing of cancer cells." BMC Cancer. 2011 Aug. 18; 11:359. In some embodiments, a peptide that targets a transferrin receptor is as described in U.S. Pat. No. 8,399,653, filed May 20, 2011, "TRANSFERRIN/TRANSFERRIN RECEPTOR-MEDIATED SIRNA DELIVERY".

As discussed above, examples of muscle targeting peptides have been reported. For example, muscle-specific peptides were identified using phage display library presenting surface heptapeptides. As one example a peptide having the amino acid sequence ASSLNIA (SEQ ID NO: 6) bound to C2C12 murine myotubes in vitro, and bound to mouse muscle tissue in vivo. Accordingly, in some embodiments, the muscle-targeting agent comprises the amino acid sequence ASSLNIA (SEQ ID NO: 6). This peptide displayed improved specificity for binding to heart and skeletal muscle tissue after intravenous injection in mice with reduced binding to liver, kidney, and brain. Additional muscle-specific peptides have been identified using phage display. For example, a 12 amino acid peptide was identified by phage display library for muscle targeting in the context of treatment for DMD. See, Yoshida D., et al., "Targeting of salicylate to skin and muscle following topical injections in rats." *Int J Pharm* 2002; 231: 177-84; the entire contents of which are hereby incorporated by reference. Here, a 12 amino acid peptide having the sequence SKTFNTHPQSTP (SEQ ID NO: 7) was identified and this muscle-targeting peptide showed improved binding to C2C12 cells relative to the ASSLNIA (SEQ ID NO: 6) peptide.

An additional method for identifying peptides selective for muscle (e.g., skeletal muscle) over other cell types includes in vitro selection, which has been described in Ghosh D., et al., "Selection of muscle-binding peptides from context-specific peptide-presenting phage libraries for adenoviral vector targeting" J Virol 2005; 79: 13667-72; the entire contents of which are incorporated herein by reference. By pre-incubating a random 12-mer peptide phage display library with a mixture of non-muscle cell types, non-specific cell binders were selected out. Following rounds of selection the 12 amino acid peptide TARGEHKEEELI (SEQ ID NO: 8) appeared most frequently. Accordingly, in some embodiments, the muscle-targeting agent comprises the amino acid sequence TARGEHKEEELI (SEQ ID NO: 8).

A muscle-targeting agent may an amino acid-containing molecule or peptide. A muscle-targeting peptide may correspond to a sequence of a protein that preferentially binds to a protein receptor found in muscle cells. In some embodiments, a muscle-targeting peptide contains a high propensity of hydrophobic amino acids, e.g. valine, such that the peptide preferentially targets muscle cells. In some embodiments, a muscle-targeting peptide has not been previously characterized or disclosed. These peptides may be conceived of, produced, synthesized, and/or derivatized using any of several methodologies, e.g. phage displayed peptide libraries, one-bead one-compound peptide libraries, or positional scanning synthetic peptide combinatorial libraries. Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081; Samoylova, T. I. and Smith, B. F. "Elucidation of muscle-binding peptides by phage display screening." Muscle Nerve, 1999, 22:4. 460-6). In some embodiments, a muscle-targeting peptide has been previously disclosed (see, e.g. Writer M. J. et al. "Targeted gene delivery to human airway epithelial cells with synthetic vectors incorporating novel targeting peptides selected by phage display." J. Drug Targeting. 2004; 12:185; Cal, D. "BDNF-mediated enhancement of inflammation and injury in the aging heart." Physiol Genomics. 2006, 24:3, 191-7; Zhang, L. "Molecular profiling of heart endothelial cells." Circulation, 2005, 112:11, 1601-11; McGuire, M. J. et al. "In vitro selection of a peptide with high selectivity for cardiomyocytes in vivo." J Mol Biol. 2004, 342:1, 171-82). Exemplary muscle-targeting peptides comprise an amino acid sequence of the following group: CQAQGQLVC (SEQ ID NO: 9), CSERSMNFC (SEQ ID NO: 10), CPKTRRVPC (SEQ ID NO: 11), WLSEA-GPVVTVRALRGTGSW (SEQ ID NO: 12), ASSLNIA (SEQ ID NO: 6), CMQHSMRVC (SEQ ID NO: 13), and DDTRHWG (SEQ ID NO: 14). In some embodiments, a muscle-targeting peptide may comprise about 2-25 amino acids, about 2-20 amino acids, about 2-15 amino acids, about 2-10 amino acids, or about 2-5 amino acids. Muscle-targeting peptides may comprise naturally-occurring amino acids, e.g. cysteine, alanine, or non-naturally-occurring or modified amino acids. Non-naturally occurring amino acids include (3-amino acids, homo-amino acids, proline derivatives, 3-substituted alanine derivatives, linear core amino acids, N-methyl amino acids, and others known in the art. In some embodiments, a muscle-targeting peptide may be linear; in other embodiments, a muscle-targeting peptide may be cyclic, e.g. bicyclic (see, e.g. Silvana, M. G. et al. Mol. Therapy, 2018, 26:1, 132-147).

iii. Muscle-Targeting Receptor Ligands

A muscle-targeting agent may be a ligand, e.g. a ligand that binds to a receptor protein. A muscle-targeting ligand may be a protein, e.g. transferrin, which binds to an internalizing cell surface receptor expressed by a muscle cell. Accordingly, in some embodiments, the muscle-targeting agent is transferrin, or a derivative thereof that binds to a transferrin receptor. A muscle-targeting ligand may alternatively be a small molecule, e.g. a lipophilic small molecule that preferentially targets muscle cells relative to other cell types. Exemplary lipophilic small molecules that may target muscle cells include compounds comprising cholesterol, cholesteryl, stearic acid, palmitic acid, oleic acid, oleyl, linolene, linoleic acid, myristic acid, sterols, dihydrotestosterone, testosterone derivatives, glycerine, alkyl chains, trityl groups, and alkoxy acids.

iv. Muscle-Targeting Aptamers

A muscle-targeting agent may be an aptamer, e.g. an RNA aptamer, which preferentially targets muscle cells relative to other cell types. In some embodiments, a muscle-targeting aptamer has not been previously characterized or disclosed.

These aptamers may be conceived of, produced, synthesized, and/or derivatized using any of several methodologies, e.g. Systematic Evolution of Ligands by Exponential Enrichment. Exemplary methodologies have been characterized in the art and are incorporated by reference (Yan, A. C. and Levy, M. "Aptamers and aptamer targeted delivery" RNA biology, 2009, 6:3, 316-20; Germer, K. et al. "RNA aptamers and their therapeutic and diagnostic applications." Int. J. Biochem. Mol. Biol. 2013; 4: 27-40). In some embodiments, a muscle-targeting aptamer has been previously disclosed (see, e.g. Phillippou, S. et al. "Selection and Identification of Skeletal-Muscle-Targeted RNA Aptamers." Mol Ther Nucleic Acids. 2018, 10:199-214; Thiel, W. H. et al. "Smooth Muscle Cell-targeted RNA Aptamer Inhibits Neointimal Formation." Mol Ther. 2016, 24:4, 779-87). Exemplary muscle-targeting aptamers include the A01B RNA aptamer and RNA Apt 14. In some embodiments, an aptamer is a nucleic acid-based aptamer, an oligonucleotide aptamer or a peptide aptamer. In some embodiments, an aptamer may be about 5-15 kDa, about 5-10 kDa, about 10-15 kDa, about 1-5 Da, about 1-3 kDa, or smaller.

v. Other Muscle-Targeting Agents

One strategy for targeting a muscle cell (e.g., a skeletal muscle cell) is to use a substrate of a muscle transporter protein, such as a transporter protein expressed on the sarcolemma. In some embodiments, the muscle-targeting agent is a substrate of an influx transporter that is specific to muscle tissue. In some embodiments, the influx transporter is specific to skeletal muscle tissue. Two main classes of transporters are expressed on the skeletal muscle sarcolemma, (1) the adenosine triphosphate (ATP) binding cassette (ABC) superfamily, which facilitate efflux from skeletal muscle tissue and (2) the solute carrier (SLC) superfamily, which can facilitate the influx of substrates into skeletal muscle. In some embodiments, the muscle-targeting agent is a substrate that binds to an ABC superfamily or an SLC superfamily of transporters. In some embodiments, the substrate that binds to the ABC or SLC superfamily of transporters is a naturally-occurring substrate. In some embodiments, the substrate that binds to the ABC or SLC superfamily of transporters is a non-naturally occurring substrate, for example, a synthetic derivative thereof that binds to the ABC or SLC superfamily of transporters.

In some embodiments, the muscle-targeting agent is a substrate of an SLC superfamily of transporters. SLC transporters are either equilibrative or use proton or sodium ion gradients created across the membrane to drive transport of substrates. Exemplary SLC transporters that have high skeletal muscle expression include, without limitation, the SATT transporter (ASCT1; SLC1A4), GLUT4 transporter (SLC2A4), GLUT7 transporter (GLUT7; SLC2A7), ATRC2 transporter (CAT-2; SLC7A2), LAT3 transporter (KIAA0245; SLC7A6), PHT1 transporter (PTR4; SLC15A4), OATP-J transporter (OATP5A1; SLC21A15), OCT3 transporter (EMT; SLC22A3), OCTN2 transporter (FLJ46769; SLC22A5), ENT transporters (ENT1; SLC29A1 and ENT2; SLC29A2), PAT2 transporter (SLC36A2), and SAT2 transporter (KIAA1382; SLC38A2). These transporters can facilitate the influx of substrates into skeletal muscle, providing opportunities for muscle targeting.

In some embodiments, the muscle-targeting agent is a substrate of an equilibrative nucleoside transporter 2 (ENT2) transporter. Relative to other transporters, ENT2 has one of the highest mRNA expressions in skeletal muscle. While human ENT2 (hENT2) is expressed in most body organs such as brain, heart, placenta, thymus, pancreas, prostate, and kidney, it is especially abundant in skeletal muscle. Human ENT2 facilitates the uptake of its substrates depending on their concentration gradient. ENT2 plays a role in maintaining nucleoside homeostasis by transporting a wide range of purine and pyrimidine nucleobases. The hENT2 transporter has a low affinity for all nucleosides (adenosine, guanosine, uridine, thymidine, and cytidine) except for inosine. Accordingly, in some embodiments, the muscle-targeting agent is an ENT2 substrate. Exemplary ENT2 substrates include, without limitation, inosine, 2',3'-dideoxyinosine, and calofarabine. In some embodiments, any of the muscle-targeting agents provided herein are associated with a molecular payload (e.g., oligonucleotide payload). In some embodiments, the muscle-targeting agent is covalently linked to the molecular payload. In some embodiments, the muscle-targeting agent is non-covalently linked to the molecular payload.

In some embodiments, the muscle-targeting agent is a substrate of an organic cation/carnitine transporter (OCTN2), which is a sodium ion-dependent, high affinity carnitine transporter. In some embodiments, the muscle-targeting agent is carnitine, mildronate, acetylcarnitine, or any derivative thereof that binds to OCTN2. In some embodiments, the carnitine, mildronate, acetylcarnitine, or derivative thereof is covalently linked to the molecular payload (e.g., oligonucleotide payload).

A muscle-targeting agent may be a protein that is protein that exists in at least one soluble form that targets muscle cells. In some embodiments, a muscle-targeting protein may be hemojuvelin (also known as repulsive guidance molecule C or hemochromatosis type 2 protein), a protein involved in iron overload and homeostasis. In some embodiments, hemojuvelin may be full length or a fragment, or a mutant with at least 75%, at least 80%, at least 85%, at least 90%, at least 95%, at least 98% or at least 99% sequence identity to a functional hemojuvelin protein. In some embodiments, a hemojuvelin mutant may be a soluble fragment, may lack a N-terminal signaling, and/or lack a C-terminal anchoring domain. In some embodiments, hemojuvelin may be annotated under GenBank RefSeq Accession Numbers NM_001316767.1, NM_145277.4, NM_202004.3, NM_213652.3, or NM_213653.3. It should be appreciated that a hemojuvelin may be of human, non-human primate, or rodent origin.

B. Molecular Payloads

Some aspects of the disclosure provide molecular payloads, e.g., for modulating a biological outcome, e.g., the transcription of a DNA sequence, the expression of a protein, or the activity of a protein. In some embodiments, a molecular payload is linked to, or otherwise associated with a muscle-targeting agent. In some embodiments, such molecular payloads are capable of targeting to a muscle cell, e.g., via specifically binding to a nucleic acid or protein in the muscle cell following delivery to the muscle cell by an associated muscle-targeting agent. It should be appreciated that various types of muscle-targeting agents may be used in accordance with the disclosure. For example, the molecular payload may comprise, or consist of, an oligonucleotide (e.g., antisense oligonucleotide), a peptide (e.g., a peptide that binds a nucleic acid or protein associated with disease in a muscle cell), a protein (e.g., a protein that binds a nucleic acid or protein associated with disease in a muscle cell), or a small molecule (e.g., a small molecule that modulates the function of a nucleic acid or protein associated with disease in a muscle cell). In some embodiments, the molecular payload is an oligonucleotide that comprises a strand having a region of complementarity to a DUX4.

Exemplary molecular payloads are described in further detail herein, however, it should be appreciated that the exemplary molecular payloads provided herein are not meant to be limiting.

i. Oligonucleotides

Any suitable oligonucleotide may be used as a molecular payload, as described herein. In some embodiments, the oligonucleotide may be designed to cause degradation of an mRNA (e.g., the oligonucleotide may be a gapmer, an siRNA, a ribozyme or an aptamer that causes degradation). In some embodiments, the oligonucleotide may be designed to block translation of an mRNA (e.g., the oligonucleotide may be a mixmer, an siRNA or an aptamer that blocks translation). In some embodiments, an oligonucleotide may be designed to cause degradation and block translation of an mRNA. In some embodiments, an oligonucleotide may be a guide nucleic acid (e.g., guide RNA) for directing activity of an enzyme (e.g., a gene editing enzyme). Other examples of oligonucleotides are provided herein. It should be appreciated that, in some embodiments, oligonucleotides in one format (e.g., antisense oligonucleotides) may be suitably adapted to another format (e.g., siRNA oligonucleotides) by incorporating functional sequences (e.g., antisense strand sequences) from one format to the other format.

Any suitable oligonucleotide may be used as a molecular payload, as described herein. Examples of oligonucleotides useful for targeting DUX4 are provided in U.S. Pat. No. 9,988,628, published on Feb. 2, 2017, entitled "AGENTS USEFUL IN TREATING FACIOSCAPULOHUMERAL MUSCULAR DYSTROPHY"; U.S. Pat. No. 9,469,851, published Oct. 30, 2014, entitled "RECOMBINANT VIRUS PRODUCTS AND METHODS FOR INHIBITING EXPRESSION OF DUX4"; US Patent Application Publication 20120225034, published on Sep. 6, 2012, entitled "AGENTS USEFUL IN TREATING FACIOSCAPULOHUMERAL MUSCULAR DYSTROPHY"; PCT Patent Application Publication Number WO 2013/120038, published on Aug. 15, 2013, entitled "MORPHOLINO TARGETING DUX4 FOR TREATING FSHD"; Chen et al., "Morpholino-mediated Knockdown of DUX4 Toward Facioscapulohumeral Muscular Dystrophy Therapeutics," Molecular Therapy, 2016, 24:8, 1405-1411; and Ansseau et al., "Antisense Oligonucleotides Used to Target the DUX4 mRNA as Therapeutic Approaches in Facioscapulohumeral Muscular Dystrophy (FSHD)," Genes, 2017, 8, 93; the contents of each of which are incorporated herein in their entireties. In some embodiments, the oligonucleotide is an antisense oligonucleotide, a morpholino, a siRNA, a shRNA, or another nucleotide which hybridizes with the target DUX4 gene or mRNA.

In some embodiments, oligonucleotides may have a region of complementarity to a sequence as set forth as: Human DUX4, corresponding to NCBI sequence NM_001293798.1 (SEQ ID NO: 15) as below and/or Mouse DUX4, corresponding to NCBI sequence NM_001081954.1 (SEQ ID NO: 16), as below. In some embodiments, the oligonucleotide may have a region of complementarity to a hypomethylated, contracted D4Z4 repeat, as in Daxinger, et al., "Genetic and Epigenetic Contributors to FSHD," published in Curr Opin Genet Dev in 2015, Lim J-W, et al., DICER/AGO-dependent epigenetic silencing of D4Z4 repeats enhanced by exogenous siRNA suggests mechanisms and therapies for FSHD Hum Mol Genet. 2015 Sep. 1; 24(17): 4817-4828, the contents of each of which are incorporated in their entireties.

In some embodiments, oligonucleotides may have a region of complementarity to a sequence set forth as follows, which is an example human DUX4 gene sequence (NM001293798.1) (SEQ ID NO: 15):
ATGGCCCTCCCGACACCCTCGGACAGCACCCTCCCCGCGGAAGCCCGGGG

ACGAGGACGGCGACGGAGACTCGTTTGGACCCCGAGCCAAAGCGAGGCCC

TGCGAGCCTGCTTTGAGCGGAACCCGTACCCGGGCATCGCCACCAGAGAA

CGGCTGGCCCAGGCCATCGGCATTCCGGAGCCCAGGGTCCAGATTTGGTT

TCAGAATGAGAGGTCACGCCAGCTGAGGCAGCACCGGCGGGAATCTCGGC

CCTGGCCCGGGAGACGCGGCCCGCCAGAAGGCCGGCGAAAGCGGACCGCC

GTCACCGGATCCCAGACCGCCCTGCTCCTCCGAGCCTTTGAGAAGGATCG

CTTTCCAGGCATCGCCGCCCGGGAGGAGCTGGCCAGAGAGACGGGCCTCC

CGGAGTCCAGGATTCAGATCTGGTTTCAGAATCGAAGGGCCAGGCACCCG

GGACAGGGTGGCAGGGCGCCCGCGCAGGCAGGCGGCCTGTGCAGCGCGGC

CCCCGGCGGGGGTCACCCTGCTCCCTCGTGGGTCGCCTTCGCCCACACCG

GCGCGTGGGGAACGGGGCTTCCCGCACCCCACGTGCCCTGCGCGCCTGGG

GCTCTCCCACAGGGGCTTTCGTGAGCCAGGCAGCGAGGGCCGCCCCCGC

GCTGCAGCCCAGCCAGGCCGCGCCGGCAGAGGGGATCTCCCAACCTGCCC

CGGCGCGCGGGGATTTCGCCTACGCCGCCCCGGCTCCTCCGGACGGGGCG

CTCTCCCACCCTCAGGCTCCTCGGTGGCCTCCGCACCCGGGCAAAAGCCG

GGAGGACCGGGACCCGCAGCGCGACGGCCTGCCGGGCCCCTGCGCGGTGG

CACAGCCTGGGCCCGCTCAAGCGGGGCCGCAGGGCCAAGGGGTGCTTGCG

CCACCCACGTCCCAGGGGAGTCCGTGGTGGGGCTGGGGCCGGGGTCCCCA

GGTCGCCGGGGCGGCGTGGGAACCCCAAGCCGGGGCAGCTCCACCTCCCC

AGCCCGCGCCCCCGGACGCCTCCGCCTCCGCGCGGCAGGGGCAGATGCAA

GGCATCCCGGCGCCCTCCCAGGCGCTCCAGGAGCCGGCGCCCTGGTCTGC

ACTCCCCTGCGGCCTGCTGCTGGATGAGCTCCTGGCGAGCCCGGAGTTTC

TGCAGCAGGCGCAACCTCTCCTAGAAACGGAGGCCCCGGGGGAGCTGGAG

GCCTCGGAAGAGGCCGCCTCGCTGGAAGCACCCCTCAGCGAGGAAGAATA

CCGGGCTCTGCTGGAGGAGCTTTAG

In some embodiments, oligonucleotides may have a region of complementarity to a sequence set forth as follows, which is an example mouse DUX4 gene sequence (SEQ ID NO: 16) (NM001081954.1):
ATGGCAGAAGCTGGCAGCCCTGTTGGTGGCAGTGGTGTGGCACGGGAATC

CCGGCGGCGCAGGAAGACGGTTTGGCAGGCCTGGCAAGAGCAGGCCCTGC

TATCAACTTTCAAGAAGAAGAGATACCTGAGCTTCAAGGAGAGGAAGGAG

CTGGCCAAGCGAATGGGGGTCTCAGATTGCCGCATCCGCGTGTGGTTTCA

GAACCGCAGGAATCGCAGTGGAGAGGAGGGGCATGCCTCAAAGAGGTCCA

TCAGAGGCTCCAGGCGGCTAGCCTCGCCACAGCTCCAGGAAGAGCTTGGA

TCCAGGCCACAGGGTAGAGGCATGCGCTCATCTGGCAGAAGGCCTCGCAC

TCGACTCACCTCGCTACAGCTCAGGATCCTAGGGCAAGCCTTTGAGAGGA

-continued

ACCCACGACCAGGCTTTGCTACCAGGGAGGAGCTGGCGCGTGACACAGGG

TTGCCCGAGGACACGATCCACATATGGTTTCAAAACCGAAGAGCTCGGCG

GCGCCACAGGAGGGGCAGGCCCACAGCTCAAGATCAAGACTTGCTGGCGT

CACAAGGGTCGGATGGGGCCCCTGCAGGTCCGGAAGGCAGAGAGCGTGAA

GGTGCCCAGGAGAACTTGTTGCCACAGGAAGAAGCAGGAAGTACGGGCAT

GGATACCTCGAGCCCTAGCGACTTGCCCTCCTTCTGCGGAGAGTCCCAGC

CTTTCCAAGTGGCACAGCCCCGTGGAGCAGGCCAACAAGAGGCCCCCACT

CGAGCAGGCAACGCAGGCTCTCTGGAACCCCTCCTTGATCAGCTGCTGGA

TGAAGTCCAAGTAGAAGAGCCTGCTCCAGCCCCTCTGAATTTGGATGGAG

ACCCTGGTGGCAGGGTGCATGAAGGTTCCCAGGAGAGCTTTTGGCCACAG

GAAGAAGCAGGAAGTACAGGCATGGATACTTCTAGCCCCAGCGACTCAAA

CTCCTTCTGCAGAGAGTCCCAGCCTTCCCAAGTGGCACAGCCCTGTGGAG

CGGGCCAAGAAGATGCCCGCACTCAAGCAGACAGCACAGGCCCTCTGGAA

CTCCTCCTCCTTGATCAACTGCTGGACGAAGTCCAAAAGGAAGAGCATGT

GCCAGTCCCACTGGATTGGGGTAGAAATCCTGGCAGCAGGGAGCATGAAG

GTTCCCAGGACAGCTTACTGCCCCTGGAGGAAGCAGTAAATTCGGGCATG

GATACCTCGATCCCTAGCATCTGGCCAACCTTCTGCAGAGAATCCCAGCC

TCCCCAAGTGGCACAGCCCTCTGGACCAGGCCAAGCACAGGCCCCCACTC

AAGGTGGGAACACGGACCCCCTGGAGCTCTTCCTCTATCAACTGTTGGAT

GAAGTCCAAGTAGAAGAGCATGCTCCAGCCCCTCTGAATTGGGATGTAGA

TCCTGGTGGCAGGGTGCATGAAGGTTCGTGGGAGAGCTTTTGGCCACAGG

AAGAAGCAGGAAGTACAGGCCTGGATACTTCAAGCCCCAGCGACTCAAAC

TCCTTCTTCAGAGAGTCCAAGCCTTCCCAAGTGGCACAGCGCCGTGGAGC

GGGCCAAGAAGATGCCCGCACTCAAGCAGACAGCACAGGCCCTCTGGAAC

TCCTCCTCTTTGATCAACTGCTGGACGAAGTCCAAAAGGAAGAGCATGTG

CCAGCCCCACTGGATTGGGGTAGAAATCCTGGCAGCATGGAGCATGAAGG

TTCCCAGGACAGCTTACTGCCCCTGGAGGAAGCAGCAAATTCGGGCAGGG

ATACCTCGATCCCTAGCATCTGGCCAGCCTTCTGCAGAAAATCCCAGCCT

CCCCAAGTGGCACAGCCCTCTGGACCAGGCCAAGCACAGGCCCCCATTCA

AGGTGGGAACACGGACCCCCTGGAGCTCTTCCTTGATCAACTGCTGACCG

AAGTCCAACTTGAGGAGCAGGGGCCTGCCCCTGTGAATGTGGAGGAAACA

TGGGAGCAAATGGACACAACACCTATCTGCCTCTCACTTCAGAAGAATAT

CAGACTCTTCTAGATATGCTCTGA.

In some embodiments, an oligonucleotide may have a region of complementarity to DUX4 gene sequences of multiple species, e.g., selected from human, mouse and non-human species.

In some embodiments, an oligonucleotide that targets DUX4 is a FM10 sequence. In some embodiments, an oligonucleotide that targets DUX4 is a phosphorodiamidate morpholino version of a FM10 sequence. In some embodiments, an oligonucleotide that targets DUX4 comprises the sequence (SEQ ID NO: 45)
GGGCATTTTAATATATCTCTGAACT In some embodiments, an oligonucleotide that targets DUX4 comprises a sequence that is complementary to at least 15 consecutive nucleotides of (SEQ ID NO: 46)
AGTTCAGAGATATATTAAAATGCCC In some embodiments, muscle specific E3 ubiquitin ligases are overexpressed in FSHD and function in muscle atrophy (see, e.g., Vanderplanck, C. et al. "The FSHD Atrophic Myotube Phenotype Is Caused by DUX4 Expression" PLoS One 6,10:e26820, 2011). In some embodiments, downregulation of these ligases presents a viable therapeutic strategy. In some embodiments, an oligonucleotide may target, e.g., inhibit the expression of, a muscle specific E3 ubiquitin ligase implicated in FSHD, such as MuRF1 (also known as TRIM63) and MAFbx (also known as Fbx032) in some embodiments, an oligonucleotide may have a region of complementarity to at least one MuRF1 gene sequence, e.g. human MuRF1 (NCBI Gene ID 84676). In some embodiments, an oligonucleotide may have a region of complementarity to at least one MAFbx gene sequence, e.g. human MAFbx (NCBI Gene ID 114907).

a. Oligonucleotide Size/Sequence

Oligonucleotides may be of a variety of different lengths, e.g., depending on the format. In some embodiments, an oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In a some embodiments, the oligonucleotide is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 21 to 23 nucleotides in lengths, etc.

In some embodiments, a complementary nucleic acid sequence of an oligonucleotide for purposes of the present disclosure is specifically hybridizable or specific for the target nucleic acid when binding of the sequence to the target molecule (e.g., mRNA) interferes with the normal function of the target (e.g., mRNA) to cause a loss of activity (e.g., inhibiting translation) or expression (e.g., degrading a target mRNA) and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency. Thus, in some embodiments, an oligonucleotide may be at least 80%, at least 85%, at least 90%, at least 91%, at least 92%, at least 93%, at least 94%, at least 95%, at least 96%, at least 97%, at least 98%, at least 99% or 100% complementary to the consecutive nucleotides of an target nucleic acid. In some embodiments a complementary nucleotide sequence need not be 100% complementary to that of its target to be specifically hybridizable or specific for a target nucleic acid.

In some embodiments, an oligonucleotide comprises region of complementarity to a target nucleic acid that is in the range of 8 to 15, 8 to 30, 8 to 40, or 10 to 50, or 5 to 50, or 5 to 40 nucleotides in length. In some embodiments, a region of complementarity of an oligonucleotide to a target nucleic acid is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the region of complementarity is complementary with at least 8 consecutive nucleotides of a target nucleic acid. In some embodiments, an oligonucleotide may contain 1, 2 or 3 base mismatches compared to the portion of the consecutive nucleotides of target nucleic acid. In some embodiments the oligonucleotide may have up to 3 mismatches over 15 bases, or up to 2 mismatches over 10 bases.

b. Oligonucleotide Modifications:

The oligonucleotides described herein may be modified, e.g., comprise a modified sugar moiety, a modified internucleoside linkage, a modified nucleotide and/or combinations thereof. In addition, in some embodiments, oligonucleotides may exhibit one or more of the following properties: do not mediate alternative splicing; are not immune stimulatory; are nuclease resistant; have improved cell uptake compared to unmodified oligonucleotides; are not toxic to cells or mammals; have improved endosomal exit internally in a cell; minimizes TLR stimulation; or avoid pattern recognition receptors. Any of the modified chemistries or formats of oligonucleotides described herein can be combined with each other. For example, one, two, three, four, five, or more different types of modifications can be included within the same oligonucleotide.

In some embodiments, certain nucleotide modifications may be used that make an oligonucleotide into which they are incorporated more resistant to nuclease digestion than the native oligodeoxynucleotide or oligoribonucleotide molecules; these modified oligonucleotides survive intact for a longer time than unmodified oligonucleotides. Specific examples of modified oligonucleotides include those comprising modified backbones, for example, modified internucleoside linkages such as phosphorothioates, phosphotriesters, methyl phosphonates, short chain alkyl or cycloalkyl intersugar linkages or short chain heteroatomic or heterocyclic intersugar linkages. Accordingly, oligonucleotides of the disclosure can be stabilized against nucleolytic degradation such as by the incorporation of a modification, e.g., a nucleotide modification.

In some embodiments, an oligonucleotide may be of up to 50 or up to 100 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are modified nucleotides. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are modified nucleotides. The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are modified nucleotides. Optionally, the oligonucleotides may have every nucleotide except 1, 2, 3, 4, 5, 6, 7, 8, 9, or 10 nucleotides modified. Oligonucleotide modifications are described further herein.

c. Modified Nucleotides

In some embodiments, an oligonucleotide include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA).

In some embodiments, an oligonucleotide can include at least one 2'-O-methyl-modified nucleotide, and in some embodiments, all of the nucleotides include a 2'-O-methyl modification. In some embodiments, an oligonucleotide comprises modified nucleotides in which the ribose ring comprises a bridge moiety connecting two atoms in the ring, e.g., connecting the 2'-O atom to the 4'-C atom. In some embodiments, the oligonucleotides are "locked," e.g., comprise modified nucleotides in which the ribose ring is "locked" by a methylene bridge connecting the 2'-O atom and the 4'-C atom. Examples of LNAs are described in International Patent Application Publication WO/2008/043753, published on Apr. 17, 2008, and entitled "RNA Antagonist Compounds For The Modulation Of PCSK9", the contents of which are incorporated herein by reference in its entirety.

Other modifications that may be used in the oligonucleotides disclosed herein include ethylene-bridged nucleic acids (ENAs). ENAs include, but are not limited to, 2'-O,4'-C-ethylene-bridged nucleic acids. Examples of ENAs are provided in International Patent Publication No. WO 2005/042777, published on May 12, 2005, and entitled "APP/ENA Antisense"; Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties.

In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. In some embodiments, the oligonucleotide comprises a modified nucleotide disclosed in one of the following United States Patent or Patent Application Publications: U.S. Pat. No. 7,399,845, issued on Jul. 15, 2008, and entitled "6-Modified Bicyclic Nucleic Acid Analogs"; U.S. Pat. No. 7,741,457, issued on Jun. 22, 2010, and entitled "6-Modified Bicyclic Nucleic Acid Analogs"; U.S. Pat. No. 8,022,193, issued on Sep. 20, 2011, and entitled "6-Modified Bicyclic Nucleic Acid Analogs"; U.S. Pat. No. 7,569,686, issued on Aug. 4, 2009, and entitled "Compounds And Methods For Synthesis Of Bicyclic Nucleic Acid Analogs"; U.S. Pat. No. 7,335,765, issued on Feb. 26, 2008, and entitled "Novel Nucleoside And Oligonucleotide Analogues"; U.S. Pat. No. 7,314,923, issued on Jan. 1, 2008, and entitled "Novel Nucleoside And Oligonucleotide Analogues"; U.S. Pat. No. 7,816,333, issued on Oct. 19, 2010, and entitled "Oligonucleotide Analogues And Methods Utilizing The Same" and US Publication Number 2011/0009471 now U.S. Pat. No. 8,957,201, issued on Feb. 17, 2015, and entitled "Oligonucleotide Analogues And Methods Utilizing The Same", the entire contents of each of which are incorporated herein by reference for all purposes.

In some embodiments, the oligonucleotide comprises at least one nucleotide modified at the 2' position of the sugar, preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA.

In some embodiments, the oligonucleotide may have at least one modified nucleotide that results in an increase in Tm of the oligonucleotide in a range of 1° C., 2° C., 3° C., 4° C., or 5° C. compared with an oligonucleotide that does not have the at least one modified nucleotide. The oligonucleotide may have a plurality of modified nucleotides that result in a total increase in Tm of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the modified nucleotide.

The oligonucleotide may comprise alternating nucleotides of different kinds. For example, an oligonucleotide may comprise alternating deoxyribonucleotides or ribonucleotides and 2'-fluoro-deoxyribonucleotides. An oligonucleotide may comprise alternating deoxyribonucleotides or ribonucleotides and 2'-O-methyl nucleotides. An oligonucleotide may comprise alternating 2'-fluoro nucleotides and 2'-O-methyl nucleotides. An oligonucleotide may comprise alternating bridged nucleotides and 2'-fluoro or 2'-O-methyl nucleotides.

d. Internucleotide Linkages/Backbones

In some embodiments, oligonucleotide may contain a phosphorothioate or other modified internucleotide linkage. In some embodiments, the oligonucleotide comprises phosphorothioate internucleoside linkages. In some embodiments, the oligonucleotide comprises phosphorothioate internucleoside linkages between at least two nucleotides. In some embodiments, the oligonucleotide comprises phosphorothioate internucleoside linkages between all nucleotides. For example, in some embodiments, oligonucleotides comprise modified internucleotide linkages at the first, second, and/or third internucleoside linkage at the 5' or 3' end of the nucleotide sequence.

Phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177, 196; 5,188,897; 5,264,423; 5,276,019; 5,278,302; 5,286, 717; 5,321,131; 5,399,676; 5,405,939; 5,453,496; 5,455, 233; 5,466,677; 5,476,925; 5,519,126; 5,536,821; 5,541, 306; 5,550,111; 5,563,253; 5,571,799; 5,587,361; and 5,625, 050.

In some embodiments, oligonucleotides may have heteroatom backbones, such as methylene(methylimino) or MMI backbones; amide backbones (see De Mesmaeker et al. Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497).

e. Stereospecific Oligonucleotides

In some embodiments, internucleotidic phosphorus atoms of oligonucleotides are chiral, and the properties of the oligonucleotides are adjusted based on the configuration of the chiral phosphorus atoms. In some embodiments, appropriate methods may be used to synthesize P-chiral oligonucleotide analogs in a stereocontrolled manner (e.g., as described in Oka N, Wada T, Stereocontrolled synthesis of oligonucleotide analogs containing chiral internucleotidic phosphorus atoms. Chem Soc Rev. 2011 December; 40(12): 5829-43.) In some embodiments, phosphorothioate containing oligonucleotides are provided that comprise nucleoside units that are joined together by either substantially all Sp or substantially all Rp phosphorothioate intersugar linkages. In some embodiments, such phosphorothioate oligonucleotides having substantially chirally pure intersugar linkages are prepared by enzymatic or chemical synthesis, as described, for example, in U.S. Pat. No. 5,587,261, issued on Dec. 12, 1996, the contents of which are incorporated herein by reference in their entirety. In some embodiments, chirally controlled oligonucleotides provide selective cleavage patterns of a target nucleic acid. For example, in some embodiments, a chirally controlled oligonucleotide provides single site cleavage within a complementary sequence of a nucleic acid, as described, for example, in US Patent Application Publication 20170037399 A1, published on Feb. 2, 2017, entitled "CHIRAL DESIGN", the contents of which are incorporated herein by reference in their entirety.

f. Morpholinos

In some embodiments, the oligonucleotide may be a morpholino-based compounds. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

g. Peptide Nucleic Acids (PNAs)

In some embodiments, both a sugar and an internucleoside linkage (the backbone) of the nucleotide units of an oligonucleotide are replaced with novel groups. In some embodiments, the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative publication that report the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

h. Gapmers

In some embodiments, the oligonucleotide is a gapmer. A gapmer oligonucleotide generally has the formula 5'-X—Y-Z-3', with X and Z as flanking regions around a gap region Y. In some embodiments, the Y region is a contiguous stretch of nucleotides, e.g., a region of at least 6 DNA nucleotides, which are capable of recruiting an RNAse, such as RNAse H. In some embodiments, the gapmer binds to the target nucleic acid, at which point an RNAse is recruited and can then cleave the target nucleic acid. In some embodiments, the Y region is flanked both 5' and 3' by regions X and Z comprising high-affinity modified nucleotides, e.g., one to six modified nucleotides. Examples of modified nucleotides include, but are not limited to, 2' MOE or 2'OMe or Locked Nucleic Acid bases (LNA). The flanking sequences X and Z may be of one to twenty nucleotides, one to eight nucleotides or one to five nucleotides in length, in some embodiments. The flanking sequences X and Z may be of similar length or of dissimilar lengths. The gap-segment Y may be a nucleotide sequence of five to twenty nucleotides, size to twelve nucleotides or six to ten nucleotides in length, in some embodiments.

In some embodiments, the gap region of the gapmer oligonucleotides may contain modified nucleotides known to be acceptable for efficient RNase H action in addition to DNA nucleotides, such as C4'-substituted nucleotides, acyclic nucleotides, and arabino-configured nucleotides. In some embodiments, the gap region comprises one or more unmodified internucleosides. In some embodiments, one or both flanking regions each independently comprise one or more phosphorothioate internucleoside linkages (e.g., phosphorothioate internucleoside linkages or other linkages) between at least two, at least three, at least four, at least five or more nucleotides. In some embodiments, the gap region and two flanking regions each independently comprise modified internucleoside linkages (e.g., phosphorothioate internucleoside linkages or other linkages) between at least two, at least three, at least four, at least five or more nucleotides.

A gapmer may be produced using appropriate methods. Representative U.S. patents, U.S. patent publications, and PCT publications that teach the preparation of gapmers include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 5,898,031; 7,432,250; and 7,683,036; U.S. patent publication Nos. US20090286969, US20100197762, and US20110112170; and PCT publication Nos. WO2008049085 and WO2009090182, each of which is herein incorporated by reference in its entirety.

i. Mixmers

In some embodiments, an oligonucleotide described herein may be a mixmer or comprise a mixmer sequence pattern. In general, mixmers are oligonucleotides that comprise both naturally and non-naturally occurring nucleotides or comprise two different types of non-naturally occurring nucleotides typically in an alternating pattern. Mixmers generally have higher binding affinity than unmodified oligonucleotides and may be used to specifically bind a target molecule, e.g., to block a binding site on the target molecule. Generally, mixmers do not recruit an RNAse to the target molecule and thus do not promote cleavage of the target molecule. Such oligonucleotides that are incapable of recruiting RNAse H have been described, for example, see WO2007/112754 or WO2007/112753.

In some embodiments, the mixmer comprises or consists of a repeating pattern of nucleotide analogues and naturally occurring nucleotides, or one type of nucleotide analogue and a second type of nucleotide analogue. However, a mixmer need not comprise a repeating pattern and may instead comprise any arrangement of modified nucleotides and naturally occurring nucleotides or any arrangement of one type of modified nucleotide and a second type of modified nucleotide. The repeating pattern, may, for instance be every second or every third nucleotide is a modified nucleotide, such as LNA, and the remaining nucleotides are naturally occurring nucleotides, such as DNA, or are a 2' substituted nucleotide analogue such as 2'MOE or 2' fluoro analogues, or any other modified nucleotide described herein. It is recognized that the repeating pattern of modified nucleotide, such as LNA units, may be combined with modified nucleotide at fixed positions—e.g. at the 5' or 3' termini.

In some embodiments, a mixmer does not comprise a region of more than 5, more than 4, more than 3, or more than 2 consecutive naturally occurring nucleotides, such as DNA nucleotides. In some embodiments, the mixmer comprises at least a region consisting of at least two consecutive modified nucleotide, such as at least two consecutive LNAs. In some embodiments, the mixmer comprises at least a region consisting of at least three consecutive modified nucleotide units, such as at least three consecutive LNAs.

In some embodiments, the mixmer does not comprise a region of more than 7, more than 6, more than 5, more than 4, more than 3, or more than 2 consecutive nucleotide analogues, such as LNAs. In some embodiments, LNA units may be replaced with other nucleotide analogues, such as those referred to herein.

Mixmers may be designed to comprise a mixture of affinity enhancing modified nucleotides, such as in non-limiting example LNA nucleotides and 2'-O-methyl nucleotides. In some embodiments, a mixmer comprises modified internucleoside linkages (e.g., phosphorothioate internucleoside linkages or other linkages) between at least two, at least three, at least four, at least five or more nucleotides.

A mixmer may be produced using any suitable method. Representative U.S. patents, U.S. patent publications, and PCT publications that teach the preparation of mixmers include U.S. patent publication Nos. US20060128646, US20090209748, US20090298916, US20110077288, and US20120322851, and U.S. Pat. No. 7,687,617.

In some embodiments, a mixmer comprises one or more morpholino nucleotides. For example, in some embodiments, a mixmer may comprise morpholino nucleotides mixed (e.g., in an alternating manner) with one or more other nucleotides (e.g., DNA, RNA nucleotides) or modified nucleotides (e.g., LNA, 2'-O-Methyl nucleotides).

In some embodiments, mixmers are useful for splice correcting or exon skipping, for example, as reported in Touznik A., et al., LNA/DNA mixmer-based antisense oligonucleotides correct alternative splicing of the SMN2 gene and restore SMN protein expression in type 1 SMA fibroblasts Scientific Reports, volume 7, Article number: 3672 (2017), Chen S. et al., Synthesis of a Morpholino Nucleic Acid (MNA)-Uridine Phosphoramidite, and Exon Skipping Using MNA/2'-O-Methyl Mixmer Antisense Oligonucleotide, Molecules 2016, 21, 1582, the contents of each which are incorporated herein by reference.

j. RNA Interference (RNAi)

In some embodiments, oligonucleotides provided herein may be in the form of small interfering RNAs (siRNA), also known as short interfering RNA or silencing RNA. SiRNA, is a class of double-stranded RNA molecules, typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective.

Following selection of an appropriate target RNA sequence, siRNA molecules that comprise a nucleotide sequence complementary to all or a portion of the target sequence, i.e. an antisense sequence, can be designed and prepared using appropriate methods (see, e.g., PCT Publication Number WO 2004/016735; and U.S. Patent Publication Nos. 2004/0077574 and 2008/0081791).

The siRNA molecule can be double stranded (i.e. a dsRNA molecule comprising an antisense strand and a complementary sense strand) or single-stranded (i.e. a ssRNA molecule comprising just an antisense strand). The siRNA molecules can comprise a duplex, asymmetric duplex, hairpin or asymmetric hairpin secondary structure, having self-complementary sense and antisense strands.

Double-stranded siRNA may comprise RNA strands that are the same length or different lengths. Double-stranded siRNA molecules can also be assembled from a single oligonucleotide in a stem-loop structure, wherein self-complementary sense and antisense regions of the siRNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi. Small hairpin RNA (shRNA) molecules thus are also contemplated herein. These molecules comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a dsRNA molecule (optionally with additional processing steps that may result in addition or removal of one, two, three or more nucleotides from the 3' end and/or the 5' end of either or both strands). A spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end and/or the 5' end of either or both strands). A spacer sequence is may be an unrelated nucleotide sequence that is situated between two complementary nucleotide sequence regions which, when annealed into a double-stranded nucleic acid, comprise a shRNA.

The overall length of the siRNA molecules can vary from about 14 to about 100 nucleotides depending on the type of siRNA molecule being designed. Generally between about 14 and about 50 of these nucleotides are complementary to the RNA target sequence, i.e. constitute the specific antisense sequence of the siRNA molecule. For example, when the siRNA is a double- or single-stranded siRNA, the length can vary from about 14 to about 50 nucleotides, whereas when the siRNA is a shRNA or circular molecule, the length can vary from about 40 nucleotides to about 100 nucleotides.

An siRNA molecule may comprise a 3' overhang at one end of the molecule. The other end may be blunt-ended or have also an overhang (5' or 3'). When the siRNA molecule comprises an overhang at both ends of the molecule, the length of the overhangs may be the same or different. In one embodiment, the siRNA molecule of the present disclosure comprises 3' overhangs of about 1 to about 3 nucleotides on both ends of the molecule.

k. MicroRNA (MiRNAs)

In some embodiments, an oligonucleotide may be a microRNA (miRNA). MicroRNAs (referred to as "miR-NAs") are small non-coding RNAs, belonging to a class of regulatory molecules that control gene expression by binding to complementary sites on a target RNA transcript. Typically, miRNAs are generated from large RNA precursors (termed pri-miRNAs) that are processed in the nucleus into approximately 70 nucleotide pre-miRNAs, which fold into imperfect stem-loop structures. These pre-miRNAs typically undergo an additional processing step within the cytoplasm where mature miRNAs of 18-25 nucleotides in length are excised from one side of the pre-miRNA hairpin by an RNase III enzyme, Dicer.

As used herein, miRNAs including pri-miRNA, pre-miRNA, mature miRNA or fragments of variants thereof that retain the biological activity of mature miRNA. In one embodiment, the size range of the miRNA can be from 21 nucleotides to 170 nucleotides. In one embodiment the size range of the miRNA is from 70 to 170 nucleotides in length. In another embodiment, mature miRNAs of from 21 to 25 nucleotides in length can be used.

l. Aptamers

In some embodiments, oligonucleotides provided herein may be in the form of aptamers. Generally, in the context of molecular payloads, aptamer is any nucleic acid that binds specifically to a target, such as a small molecule, protein, nucleic acid in a cell. In some embodiments, the aptamer is a DNA aptamer or an RNA aptamer. In some embodiments, a nucleic acid aptamer is a single-stranded DNA or RNA (ssDNA or ssRNA). It is to be understood that a single-stranded nucleic acid aptamer may form helices and/or loop structures. The nucleic acid that forms the nucleic acid aptamer may comprise naturally occurring nucleotides, modified nucleotides, naturally occurring nucleotides with hydrocarbon linkers (e.g., an alkylene) or a polyether linker (e.g., a PEG linker) inserted between one or more nucleotides, modified nucleotides with hydrocarbon or PEG linkers inserted between one or more nucleotides, or a combination of thereof. Exemplary publications and patents describing aptamers and method of producing aptamers include, e.g., Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823; 6,569,630; 8,318,438 and PCT application WO 99/31275, each incorporated herein by reference.

m. Ribozymes

In some embodiments, oligonucleotides provided herein may be in the form of a ribozyme. A ribozyme (ribonucleic acid enzyme) is a molecule, typically an RNA molecule, that is capable of performing specific biochemical reactions, similar to the action of protein enzymes. Ribozymes are molecules with catalytic activities including the ability to cleave at specific phosphodiester linkages in RNA molecules to which they have hybridized, such as mRNAs, RNA-containing substrates, lncRNAs, and ribozymes, themselves.

Ribozymes may assume one of several physical structures, one of which is called a "hammerhead." A hammerhead ribozyme is composed of a catalytic core containing nine conserved bases, a double-stranded stem and loop structure (stem-loop II), and two regions complementary to the target RNA flanking regions the catalytic core. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to a specific ribonucleotide triplet by a transesterification reaction from a 3', 5'-phosphate diester to a 2', 3'-cyclic phosphate diester. Without wishing to be bound by theory, it is believed that this catalytic activity requires the presence of specific, highly conserved sequences in the catalytic region of the ribozyme.

Modifications in ribozyme structure have also included the substitution or replacement of various non-core portions of the molecule with non-nucleotidic molecules. For example, Benseler et al. (J. Am. Chem. Soc. (1993) 115: 8483-8484) disclosed hammerhead-like molecules in which two of the base pairs of stem II, and all four of the nucleotides of loop II were replaced with non-nucleoside linkers based on hexaethylene glycol, propanediol, bis(triethylene glycol) phosphate, tris(propanediol)bisphosphate, or bis(propanediol) phosphate. Ma et al. (Biochem. (1993) 32:1751-1758; Nucleic Acids Res. (1993) 21:2585-2589) replaced the six nucleotide loop of the TAR ribozyme hairpin with non-nucleotidic, ethylene glycol-related linkers. Thomson et al. (Nucleic Acids Res. (1993) 21:5600-5603) replaced loop II with linear, non-nucleotidic linkers of 13, 17, and 19 atoms in length.

Ribozyme oligonucleotides can be prepared using well known methods (see, e.g., PCT Publications WO9118624; WO9413688; WO9201806; and WO 92/07065; and U.S. Pat. Nos. 5,436,143 and 5,650,502) or can be purchased from commercial sources (e.g., US Biochemicals) and, if desired, can incorporate nucleotide analogs to increase the resistance of the oligonucleotide to degradation by nucleases in a cell. The ribozyme may be synthesized in any known manner, e.g., by use of a commercially available synthesizer produced, e.g., by Applied Biosystems, Inc. or Milligen. The ribozyme may also be produced in recombinant vectors by conventional means. See, Molecular Cloning: A Laboratory Manual, Cold Spring Harbor Laboratory (Current edition). The ribozyme RNA sequences maybe synthesized conventionally, for example, by using RNA polymerases such as T7 or SP6.

n. Guide Nucleic Acids

In some embodiments, oligonucleotides are guide nucleic acid, e.g., guide RNA (gRNA) molecules. Generally, a guide RNA is a short synthetic RNA composed of (1) a scaffold sequence that binds to a nucleic acid programmable DNA binding protein (napDNAbp), such as Cas9, and (2) a nucleotide spacer portion that defines the DNA target sequence (e.g., genomic DNA target) to which the gRNA binds in order to bring the nucleic acid programmable DNA binding protein in proximity to the DNA target sequence. In some embodiments, the napDNAbp is a nucleic acid-programmable protein that forms a complex with (e.g., binds or associates with) one or more RNA(s) that targets the nucleic acid-programmable protein to a target DNA sequence (e.g., a target genomic DNA sequence). In some embodiments, a nucleic acid-programmable nuclease, when in a complex with an RNA, may be referred to as a nuclease:RNA complex. Guide RNAs can exist as a complex of two or more RNAs, or as a single RNA molecule.

Guide RNAs (gRNAs) that exist as a single RNA molecule may be referred to as single-guide RNAs (sgRNAs), though gRNA is also used to refer to guide RNAs that exist as either single molecules or as a complex of two or more molecules. Typically, gRNAs that exist as a single RNA species comprise two domains: (1) a domain that shares homology to a target nucleic acid (i.e., directs binding of a Cas9 complex to the target); and (2) a domain that binds a Cas9 protein. In some embodiments, domain (2) corresponds to a sequence known as a tracrRNA and comprises a stem-loop structure. In some embodiments, domain (2) is identical or homologous to a tracrRNA as provided in Jinek et al., Science 337:816-821 (2012), the entire contents of which is incorporated herein by reference.

In some embodiments, a gRNA comprises two or more of domains (1) and (2), and may be referred to as an extended gRNA. For example, an extended gRNA will bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example, Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference.

o. Multimers

In some embodiments, molecular payloads may comprise multimers (e.g., concatemers) of 2 or more oligonucleotides connected by a linker. In this way, in some embodiments, the oligonucleotide loading of a complex/conjugate can be increased beyond the available linking sites on a targeting agent (e.g., available thiol sites on an antibody) or otherwise tuned to achieve a particular payload loading content. Oligonucleotides in a multimer can be the same or different (e.g., targeting different genes or different sites on the same gene or products thereof).

In some embodiments, multimers comprise 2 or more oligonucleotides linked together by a cleavable linker. However, in some embodiments, multimers comprise 2 or more oligonucleotides linked together by a non-cleavable linker. In some embodiments, a multimer comprises 2, 3, 4, 5, 6, 7, 8, 9, 10 or more oligonucleotides linked together. In some embodiments, a multimer comprises 2 to 5, 2 to 10 or 4 to 20 oligonucleotides linked together.

In some embodiments, a multimer comprises 2 or more oligonucleotides linked end-to-end (in a linear arrangement). In some embodiments, a multimer comprises 2 or more oligonucleotides linked end-to-end via a oligonucleotide based linker (e.g., poly-dT linker, an abasic linker). In some embodiments, a multimer comprises a 5' end of one oligonucleotide linked to a 3' end of another oligonucleotide. In some embodiments, a multimer comprises a 3' end of one oligonucleotide linked to a 3' end of another oligonucleotide. In some embodiments, a multimer comprises a 5' end of one oligonucleotide linked to a 5' end of another oligonucleotide. Still, in some embodiments, multimers can comprise a branched structure comprising multiple oligonucleotides linked together by a branching linker.

Further examples of multimers that may be used in the complexes provided herein are disclosed, for example, in US Patent Application Number 2015/0315588 A1, entitled Methods of delivering multiple targeting oligonucleotides to a cell using cleavable linkers, which was published on Nov. 5, 2015; US Patent Application Number 2015/0247141 A1, entitled Multimeric Oligonucleotide Compounds, which was published on Sep. 3, 2015, US Patent Application Number US 2011/0158937 A1, entitled Immunostimulatory Oligonucleotide Multimers, which was published on Jun. 30, 2011; and U.S. Pat. No. 5,693,773, entitled Triplex-Forming Antisense Oligonucleotides Having Abasic Linkers Targeting Nucleic Acids Comprising Mixed Sequences Of Purines And Pyrimidines, which issued on Dec. 2, 1997, the contents of each of which are incorporated herein by reference in their entireties.

ii. Small Molecules:

Any suitable small molecule may be used as a molecular payload, as described herein. In some embodiments, the small molecule is as described in US Patent Application Publication 20170340606, published on Nov. 30, 2017, entitled "METHODS OF TREATING MUSCULAR DYSTROPHY" or as described in US Patent Application Publication 20180050043, published on Feb. 22, 2018, entitled "INHIBITION OF DUX4 EXPRESSION USING BROMODOMAIN AND EXTRA-TERMINAL DOMAIN PROTEIN INHIBITORS (BETi). Further examples of small molecule payloads are provided in Bosnakovski, D., et al., High-throughput screening identifies inhibitors of DUX4-induced myoblast toxicity, Skelet Muscle, February 2014, and Choi. S., et al., "Transcriptional Inhibitors Identified in a 160,000-Compound Small-Molecule DUX4 Viability Screen," Journal of Biomolecular Screening, 2016. For example, in some embodiments, the small molecule is a transcriptional inhibitor, such as SHC351, SHC540, SHC572. In some embodiments, the small molecule is STR00316 increases production or activity of another protein, such as integrin. In some embodiments, the small molecule is a bromodomain inhibitor (BETi), such as JQ1, PF1-1, I-BET-762, I-BET-151, RVX-208, or CPI-0610.

iii. Peptides

Any suitable peptide or protein may be used as a molecular payload, as described herein. In some embodiments, a protein is an enzyme. These peptides or proteins may be produced, synthesized, and/or derivatized using several methodologies, e.g. phage displayed peptide libraries, one-bead one-compound peptide libraries, or positional scanning synthetic peptide combinatorial libraries. In some embodiments, the peptide or protein may bind a DME1 or DME2 enhancer to inhibit DUX4 expression, e.g., by blocking binding of an activator.

iv. Nucleic Acid Constructs

Any suitable gene expression construct may be used as a molecular payload, as described herein. In some embodiments, a gene expression construct may be a vector or a cDNA fragment. In some embodiments, a gene expression construct may be messenger RNA (mRNA). In some embodiments, a mRNA used herein may be a modified mRNA, e.g., as described in U.S. Pat. No. 8,710,200, issued on Apr. 24, 2014, entitled "Engineered nucleic acids encoding a modified erythropoietin and their expression". In some embodiments, a mRNA may comprise a 5' methyl cap. In some embodiments, a mRNA may comprise a polyA tail, optionally of up to 160 nucleotides in length. In some embodiments, the gene expression construct may be expressed, e.g., overexpressed, within the nucleus of a muscle cell. In some embodiments, the gene expression construct encodes a oligonucleotide (e.g., an shRNA targeting DUX4) or a protein that downregulates the expression of DUX4 (e.g., a peptide or protein that binds to DME1 or DME2 enhancer to inhibit DUX4 expression, e.g., by blocking binding of an activator). In some embodiments, the gene expression construct encodes a oligonucleotide (e.g., an shRNA targeting MuRF1 or MAFbx) that downregulates the expression of MuRF1 or MAFbx, respectively. In some embodiments, the gene expression constructs encodes a protein that comprises at least one zinc finger. In some embodiments, the gene expression construct encodes a gene editing enzyme. Additional examples of nucleic acid constructs that may be used as molecular payloads are provided in International Patent Application Publication WO2017152149A1, published on Sep. 19, 2017, entitled, "CLOSED-ENDED LINEAR DUPLEX DNA FOR NON-VIRAL GENE TRANSFER"; U.S. Pat. No. 8,853,377B2, issued on Oct. 7, 2014, entitled, "MRNA FOR USE IN TREATMENT OF HUMAN GENETIC DISEASES"; and US Patent U.S. Pat. No. 8,822,663B2, issued on Sep. 2, 2014, ENGINEERED NUCLEIC ACIDS AND METHODS OF USE THEREOF," the contents of each of which are incorporated herein by reference in their entireties.

C. Linkers

Complexes described herein generally comprise a linker that connects a muscle-targeting agent to a molecular payload. A linker comprises at least one covalent bond. In some embodiments, a linker may be a single bond, e.g., a disulfide bond or disulfide bridge, that connects a muscle-targeting agent to a molecular payload. However, in some embodiments, a linker may connect a muscle-targeting agent to a molecular payload through multiple covalent bonds. In some embodiments, a linker may be a cleavable linker. However, in some embodiments, a linker may be a non-cleavable linker. A linker is generally stable in vitro and in vivo, and may be stable in certain cellular environments. Additionally, generally a linker does not negatively impact the functional properties of either the muscle-targeting agent or the molecular payload. Examples and methods of synthesis of linkers are known in the art (see, e.g. Kline, T. et al. "Methods to Make Homogenous Antibody Drug Conjugates." Pharmaceutical Research, 2015, 32:11, 3480-3493; Jain, N. et al. "Current ADC Linker Chemistry" Pharm Res. 2015, 32:11, 3526-3540; McCombs, J. R. and Owen, S. C. "Antibody Drug Conjugates: Design and Selection of Linker, Payload and Conjugation Chemistry" AAPS J. 2015, 17:2, 339-351).

A precursor to a linker typically will contain two different reactive species that allow for attachment to both the muscle-targeting agent and a molecular payload. In some embodiments, the two different reactive species may be a nucleophile and/or an electrophile. In some embodiments, a linker is connected to a muscle-targeting agent via conjugation to a lysine residue or a cysteine residue of the muscle-targeting agent. In some embodiments, a linker is connected to a cysteine residue of a muscle-targeting agent via a maleimide-containing linker, wherein optionally the maleimide-containing linker comprises a maleimidocaproyl or maleimidomethyl cyclohexane-1-carboxylate group. In some embodiments, a linker is connected to a cysteine residue of a muscle-targeting agent or thiol functionalized molecular payload via a 3-arylpropionitrile functional group. In some embodiments, a linker is connected to a muscle-targeting agent and/or a molecular payload via an amide bond, a hydrazide, a triazole, a thioether or a disulfide bond.

i. Cleavable Linkers

A cleavable linker may be a protease-sensitive linker, a pH-sensitive linker, or a glutathione-sensitive linker. These linkers are generally cleavable only intracellularly and are preferably stable in extracellular environments, e.g. extracellular to a muscle cell.

Protease-sensitive linkers are cleavable by protease enzymatic activity. These linkers typically comprise peptide sequences and may be 2-10 amino acids, about 2-5 amino acids, about 5-10 amino acids, about 10 amino acids, about 5 amino acids, about 3 amino acids, or about 2 amino acids in length. In some embodiments, a peptide sequence may comprise naturally-occurring amino acids, e.g. cysteine, alanine, or non-naturally-occurring or modified amino acids.

Non-naturally occurring amino acids include β-amino acids, homo-amino acids, proline derivatives, 3-substituted alanine derivatives, linear core amino acids, N-methyl amino acids, and others known in the art. In some embodiments, a protease-sensitive linker comprises a valine-citrulline or alanine-citrulline dipeptide sequence. In some embodiments, a protease-sensitive linker can be cleaved by a lysosomal protease, e.g. cathepsin B, and/or an endosomal protease.

A pH-sensitive linker is a covalent linkage that readily degrades in high or low pH environments. In some embodiments, a pH-sensitive linker may be cleaved at a pH in a range of 4 to 6. In some embodiments, a pH-sensitive linker comprises a hydrazone or cyclic acetal. In some embodiments, a pH-sensitive linker is cleaved within an endosome or a lysosome.

In some embodiments, a glutathione-sensitive linker comprises a disulfide moiety. In some embodiments, a glutathione-sensitive linker is cleaved by an disulfide exchange reaction with a glutathione species inside a cell. In some embodiments, the disulfide moiety further comprises at least one amino acid, e.g. a cysteine residue.

In some embodiments, the linker is a Val-cit linker (e.g., as described in U.S. Pat. No. 6,214,345, incorporated herein by reference). In some embodiments, before conjugation, the val-cit linker has a structure of:

embodiments, a non-cleavable linker comprises an optionally substituted alkyl group, wherein the substitutions may include halogens, hydroxyl groups, oxygen species, and other common substitutions. In some embodiments, a linker may comprise an optionally substituted alkyl, an optionally substituted alkylene, an optionally substituted arylene, a heteroarylene, a peptide sequence comprising at least one non-natural amino acid, a truncated glycan, a sugar or sugars that cannot be enzymatically degraded, an azide, an alkyne-azide, a peptide sequence comprising a LPXT sequence, a thioether, a biotin, a biphenyl, repeating units of polyethylene glycol or equivalent compounds, acid esters, acid amides, sulfamides, and/or an alkoxy-amine linker. In some embodiments, sortase-mediated ligation will be utilized to covalently link a muscle-targeting agent comprising a LPXT sequence to a molecular payload comprising a (G). sequence (see, e.g. Proft T. Sortase-mediated protein ligation: an emerging biotechnology tool for protein modification and immobilization. Biotechnol Lett. 2010, 32(1):1-10).

In some embodiments, a linker may comprise a substituted alkylene, an optionally substituted alkenylene, an optionally substituted alkynylene, an optionally substituted cycloalkylene, an optionally substituted cycloalkenylene, an optionally substituted arylene, an optionally substituted heteroarylene further comprising at least one heteroatom selected from N, O, and S; an optionally substituted hetero-

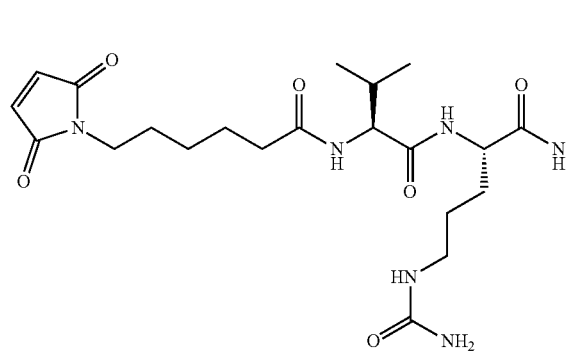

In some embodiments, after conjugation, the val-cit linker has a structure of:

cyclylene further comprising at least one heteroatom selected from N, O, and S; an imino, an optionally substi-

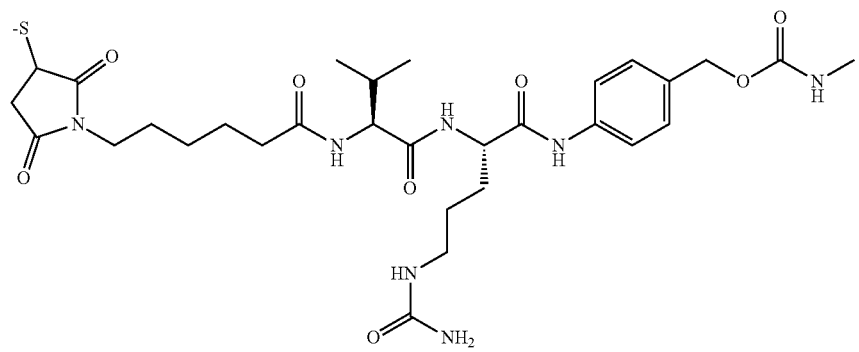

ii. Non-Cleavable Linkers

In some embodiments, non-cleavable linkers may be used. Generally, a non-cleavable linker cannot be readily degraded in a cellular or physiological environment. In some tuted nitrogen species, an optionally substituted oxygen species O, an optionally substituted sulfur species, or a poly(alkylene oxide), e.g. polyethylene oxide or polypropylene oxide.

iii. Linker Conjugation

In some embodiments, a linker is connected to a muscle-targeting agent and/or molecular payload via a phosphate, thioether, ether, carbon-carbon, or amide bond. In some embodiments, a linker is connected to an oligonucleotide through a phosphate or phosphorothioate group, e.g. a terminal phosphate of an oligonucleotide backbone. In some embodiments, a linker is connected to an muscle-targeting agent, e.g. an antibody, through a lysine or cysteine residue present on the muscle-targeting agent In some embodiments, a linker is connected to a muscle-targeting agent and/or molecular payload by a cycloaddition reaction between an azide and an alkyne to form a triazole, wherein the azide and the alkyne may be located on the muscle-targeting agent, molecular payload, or the linker. In some embodiments, an alkyne may be a cyclic alkyne, e.g., a cyclooctyne. In some embodiments, an alkyne may be bicyclononyne (also known as bicyclo[6.1.0]nonyne or BCN) or substituted bicyclononyne. In some embodiments, a cyclooctane is as described in International Patent Application Publication WO2011136645, published on Nov. 3, 2011, entitled, "Fused Cyclooctyne Compounds And Their Use In Metal free Click Reactions". In some embodiments, an azide may be a sugar or carbohydrate molecule that comprises an azide. In some embodiments, an azide may be 6-azido-6-deoxygalactose or 6-azido-N-acetylgalactosamine. In some embodiments, a sugar or carbohydrate molecule that comprises an azide is as described in International Patent Application Publication WO2016170186, published on Oct. 27, 2016, entitled, "Process For The Modification Of A Glycoprotein Using A Glycosyltransferase That Is Or Is Derived From A β(1,4)-N-Acetylgalactosaminyltransferase". In some embodiments, a cycloaddition reaction between an azide and an alkyne to form a triazole, wherein the azide and the alkyne may be located on the muscle-targeting agent, molecular payload, or the linker is as described in International Patent Application Publication WO2014065661, published on May 1, 2014, entitled, "Modified antibody, antibody-conjugate and process for the preparation thereof"; or International Patent Application Publication WO2016170186, published on Oct. 27, 2016, entitled, "Process For The Modification Of A Glycoprotein Using A Glycosyltransferase That Is Or Is Derived From A β(1,4)-N-Acetylgalactosaminyltransferase".

In some embodiments, a linker further comprises a spacer, e.g., a polyethylene glycol spacer or an acyl/carbomoyl sulfamide spacer, e.g., a HydraSpace™ spacer. In some embodiments, a spacer is as described in Verkade, J. M. M. et al., "*A Polar Sulfamide Spacer Significantly Enhances the Manufacturability, Stability, and Therapeutic Index of Antibody-Drug Conjugates*", Antibodies, 2018, 7, 12.

In some embodiments, a linker is connected to a muscle-targeting agent and/or molecular payload by the Diels-Alder reaction between a dienophile and a diene/hetero-diene, wherein the dienophile and the diene/hetero-diene may be located on the muscle-targeting agent, molecular payload, or the linker. In some embodiments a linker is connected to a muscle-targeting agent and/or molecular payload by other pericyclic reactions, e.g. ene reaction. In some embodiments, a linker is connected to a muscle-targeting agent and/or molecular payload by an amide, thioamide, or sulfonamide bond reaction. In some embodiments, a linker is connected to a muscle-targeting agent and/or molecular payload by a condensation reaction to form an oxime, hydrazone, or semicarbazide group existing between the linker and the muscle-targeting agent and/or molecular payload.

In some embodiments, a linker is connected to a muscle-targeting agent and/or molecular payload by a conjugate addition reactions between a nucleophile, e.g. an amine or a hydroxyl group, and an electrophile, e.g. a carboxylic acid or an aldehyde. In some embodiments, a nucleophile may exist on a linker and an electrophile may exist on a muscle-targeting agent or molecular payload prior to a reaction between a linker and a muscle-targeting agent or molecular payload. In some embodiments, an electrophile may exist on a linker and a nucleophile may exist on a muscle-targeting agent or molecular payload prior to a reaction between a linker and a muscle-targeting agent or molecular payload. In some embodiments, an electrophile may be an azide, a silicon centers, a carbonyl, a carboxylic acid, an anhydride, an isocyanate, a thioisocyanate, a succinimidyl ester, a sulfosuccinimidyl ester, a maleimide, an alkyl halide, an alkyl pseudohalide, an epoxide, an episulfide, an aziridine, an aryl, an activated phosphorus center, and/or an activated sulfur center. In some embodiments, a nucleophile may be an optionally substituted alkene, an optionally substituted alkyne, an optionally substituted aryl, an optionally substituted heterocyclyl, a hydroxyl group, an amino group, an alkylamino group, an anilido group, or a thiol group.

D. Examples of Antibody-Molecular Payload Complexes

Other aspects of the present disclosure provide complexes comprising any one the muscle targeting agent (e.g., a transferrin receptor antibodies) described herein covalently linked to any of the molecular payloads (e.g., an oligonucleotide) described herein. In some embodiments, the muscle targeting agent (e.g., a transferrin receptor antibody) is covalently linked to a molecular payload (e.g., an oligonucleotide) via a linker. Any of the linkers described herein may be used. In some embodiments, the linker is linked to the 5' end, the 3' end, or internally of the oligonucleotide. In some embodiments, the linker is linked to the antibody via a thiol-reactive linkage (e.g., via a cysteine in the antibody).

An exemplary structure of a complex comprising a transferrin receptor antibody covalently linked to an oligonucleotide via a Val-cit linker is provided below:

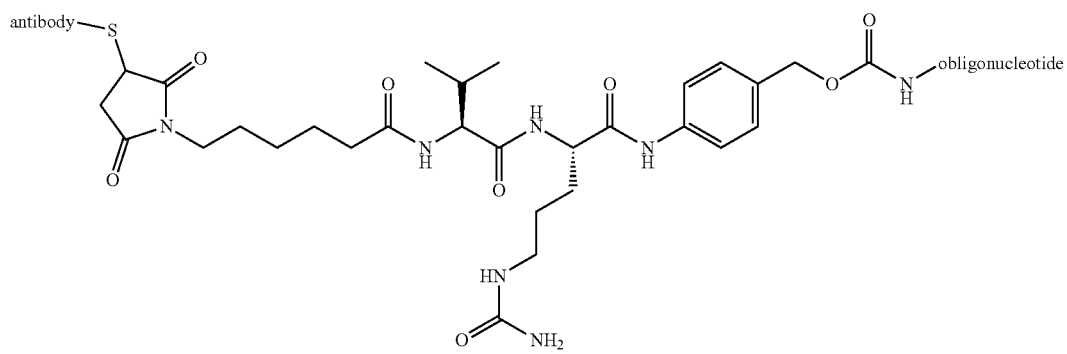

wherein the linker is linked to the 5' end, the 3' end, or internally of the oligonucleotide, and wherein the linker is linked to the antibody via a thiol-reactive linkage (e.g., via a cysteine in the antibody).

It should be appreciated that antibodies can be linked to oligonucleotides with different stochiometries, a property that may be referred to as a drug to antibody ratios (DAR) with the "drug" being the oligonucleotide. In some embodiments, one oligonucleotide is linked to an antibody (DAR=1). In some embodiments, two oligonucleotides are linked to an antibody (DAR=2). In some embodiments, three oligonucleotides are linked to an antibody (DAR=3). In some embodiments, four oligonucleotides are linked to an antibody (DAR=4). In some embodiments, a mixture of different complexes, each having a different DAR, is provided. In some embodiments, an average DAR of complexes in such a mixture may be in a range of 1 to 3, 1 to 4, 1 to 5 or more. DAR may be increased by conjugating oligonucleotides to different sites on an antibody and/or by conjugating multimers to one or more sites on antibody. For example, a DAR of 2 may be achieved by conjugating a single oligonucleotide to two different sites on an antibody or by conjugating a dimer oligonucleotide to a single site of an antibody.

In some embodiments, the complex described herein comprises a transferrin receptor antibody (e.g., an antibody or any variant thereof as described herein) covalently linked to an oligonucleotide. In some embodiments, the complex described herein comprises a transferrin receptor antibody (e.g., an antibody or any variant thereof as described herein) covalently linked to an oligonucleotide via a linker (e.g., a Val-cit linker). In some embodiments, the linker (e.g., a Val-cit linker) is linked to the 5' end, the 3' end, or internally of the oligonucleotide. In some embodiments, the linker (e.g., a Val-cit linker) is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide, wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1.

In some embodiments, the complex described herein comprises a transferrin receptor antibody covalently linked to an oligonucleotide, wherein the transferrin receptor antibody comprises a VH having the amino acid sequence of SEQ ID NO: 33 and a VL having the amino acid sequence of SEQ ID NO: 34. In some embodiments, the complex described herein comprises a transferrin receptor antibody covalently linked to an oligonucleotide, wherein the transferrin receptor antibody comprises a VH having the amino acid sequence of SEQ ID NO: 35 and a VL having the amino acid sequence of SEQ ID NO: 36.

In some embodiments, the complex described herein comprises a transferrin receptor antibody covalently linked to an oligonucleotide, wherein the transferrin receptor antibody comprises a heavy chain having the amino acid sequence of SEQ ID NO: 39 and a light chain having the amino acid sequence of SEQ ID NO: 40. In some embodiments, the complex described herein comprises a transferrin receptor antibody covalently linked to an oligonucleotide, wherein the transferrin receptor antibody comprises a heavy chain having the amino acid sequence of SEQ ID NO: 41 and a light chain having the amino acid sequence of SEQ ID NO: 42.

In some embodiments, the complex described herein comprises a transferrin receptor antibody covalently linked to an oligonucleotide via a linker (e.g., a Val-cit linker), wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1.

In some embodiments, the complex described herein comprises a transferrin receptor antibody covalently linked to an oligonucleotide via a linker (e.g., a Val-cit linker), wherein the transferrin receptor antibody comprises a VH having the amino acid sequence of SEQ ID NO: 33 and a VL having the amino acid sequence of SEQ ID NO: 34. In some embodiments, the complex described herein comprises a transferrin receptor antibody covalently linked to an oligonucleotide via a linker (e.g., a Val-cit linker), wherein the transferrin receptor antibody comprises a VH having the amino acid sequence of SEQ ID NO: 35 and a VL having the amino acid sequence of SEQ ID NO: 36.

In some embodiments, the complex described herein comprises a transferrin receptor antibody covalently linked to an oligonucleotide via a linker (e.g., a Val-cit linker), wherein the transferrin receptor antibody comprises a heavy chain having the amino acid sequence of SEQ ID NO: 39 and a light chain having the amino acid sequence of SEQ ID NO: 40. In some embodiments, the complex described herein comprises a transferrin receptor antibody covalently linked to an oligonucleotide via a linker (e.g., a Val-cit linker), wherein the transferrin receptor antibody comprises a heavy chain having the amino acid sequence of SEQ ID NO: 41 and a light chain having the amino acid sequence of SEQ ID NO: 42.

In some embodiments, the complex described herein comprises a transferrin receptor antibody covalently linked to an oligonucleotide via a Val-cit linker, wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1, and wherein the complex comprises the structure of:

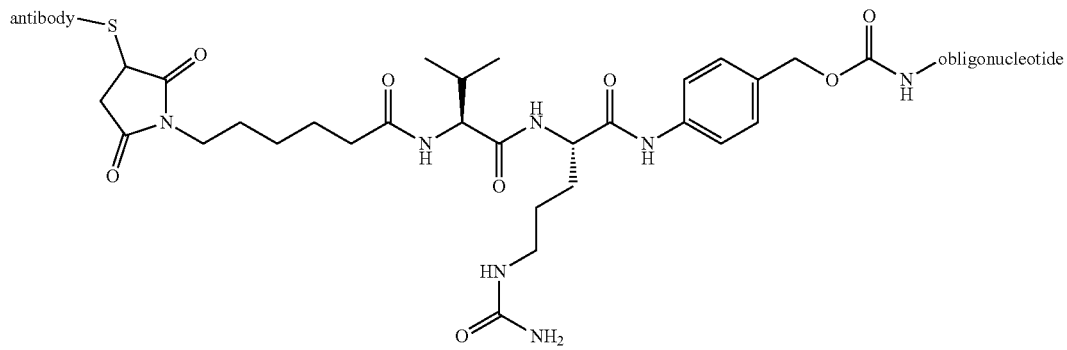

wherein the linker Val-cit linker is linked to the 5' end, the 3' end, or internally of the oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a VH having the amino acid sequence of SEQ ID NO: 33 and a VL having the amino acid sequence of SEQ ID NO: 34, and wherein the complex comprises the structure of:

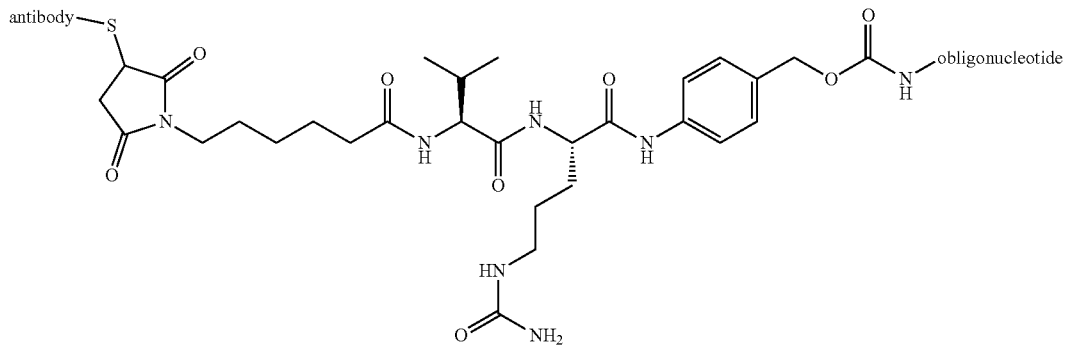

wherein the linker Val-cit linker is linked to the 5' end, the 3' end, or internally of the oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a VH having the amino acid sequence of SEQ ID NO: 35 and a VL having the amino acid sequence of SEQ ID NO: 36, and wherein the complex comprises the structure of:

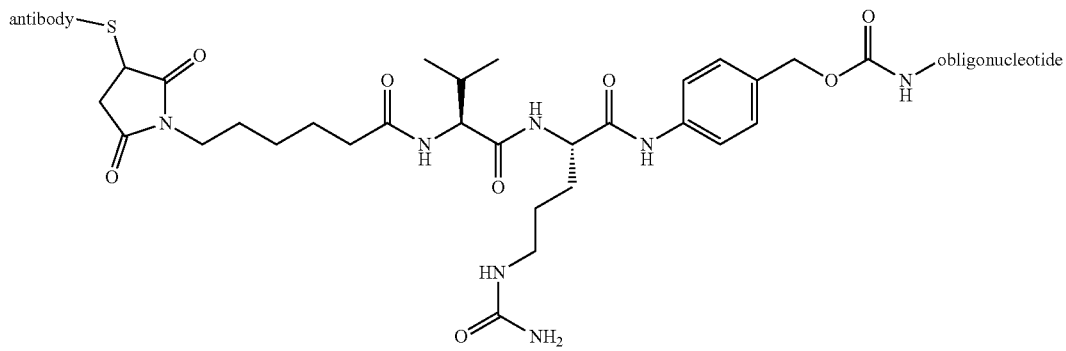

wherein the linker Val-cit linker is linked to the 5' end, the 3' end, or internally of the oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a heavy chain having the amino acid sequence of SEQ ID NO: 39 and a light chain having the amino acid sequence of SEQ ID NO: 40, and wherein the complex comprises the structure of:

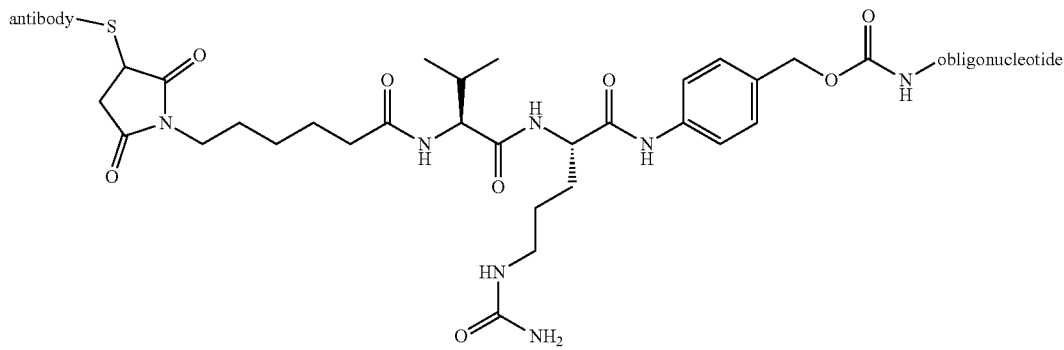

wherein the linker Val-cit linker is linked to the 5' end, the 3' end, or internally of an oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a heavy chain having the amino acid sequence of SEQ ID NO: 41 and a light chain having the amino acid sequence of SEQ ID NO: 42, and wherein the complex comprises the structure of:

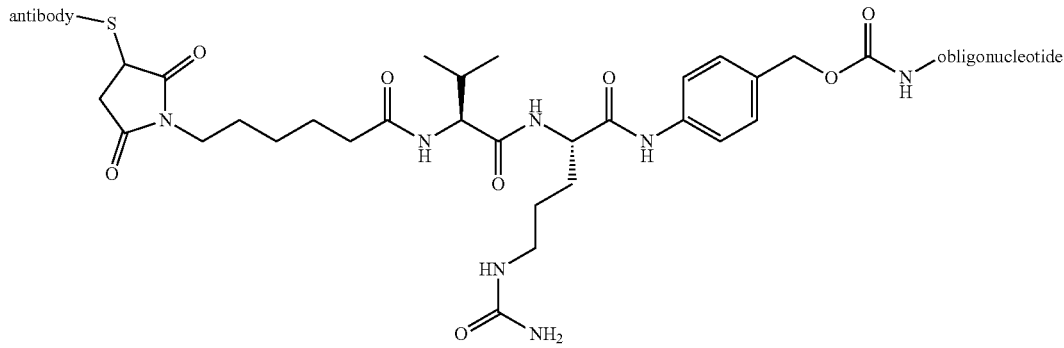

wherein the linker Val-cit linker is linked to the 5' end, the 3' end, or internally of an oligonucleotide, and wherein the Val-cit linker is linked to the antibody (e.g., an antibody or any variant thereof as described herein) via a thiol-reactive linkage (e.g., via a cysteine in the antibody).

III. Formulations

Complexes provided herein may be formulated in any suitable manner. Generally, complexes provided herein are formulated in a manner suitable for pharmaceutical use. For example, complexes can be delivered to a subject using a formulation that minimizes degradation, facilitates delivery and/or uptake, or provides another beneficial property to the complexes in the formulation. In some embodiments, provided herein are compositions comprising complexes and pharmaceutically acceptable carriers. Such compositions can be suitably formulated such that when administered to a subject, either into the immediate environment of a target cell or systemically, a sufficient amount of the complexes enter target muscle cells. In some embodiments, complexes are formulated in buffer solutions such as phosphate-buffered saline solutions, liposomes, micellar structures, and capsids.

It should be appreciated that, in some embodiments, compositions may include separately one or more components of complexes provided herein (e.g., muscle-targeting agents, linkers, molecular payloads, or precursor molecules of any one of them).

In some embodiments, complexes are formulated in water or in an aqueous solution (e.g., water with pH adjustments). In some embodiments, complexes are formulated in basic buffered aqueous solutions (e.g., PBS). In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil).

In some embodiments, a complex or component thereof (e.g., oligonucleotide or antibody) is lyophilized for extending its shelf-life and then made into a solution before use (e.g., administration to a subject). Accordingly, an excipient in a composition comprising a complex, or component thereof, described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, administration. Typically, the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), and suitable mixtures thereof. In some embodiments, formulations include isotonic agents, for example, sugars, polyalcohols such as mannitol, sorbitol, and sodium chloride in the composition. Sterile injectable solutions can be prepared by incorporating the a complexes in a required amount in a selected solvent with one or a combination of ingredients enumerated above, as required, followed by filtered sterilization.

In some embodiments, a composition may contain at least about 0.1% of the a complex, or component thereof, or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

IV. Methods of Use/Treatment

Complexes comprising a muscle-targeting agent covalently to a molecular payload as described herein are effective in treating FSHD. In some embodiments, complexes are effective in treating Type I FSHD. In some embodiments, complexes are effective in treating Type II FSHD. In some embodiments, FSHD is associated with deletions in D4Z4 repeat regions on chromosome 4 which contain the DUX4 gene. In some embodiments, FSHD is associated with mutations in the SMCHD1 gene.

In some embodiments, a subject may be a human subject, a non-human primate subject, a rodent subject, or any suitable mammalian subject. In some embodiments, a subject may have myotonic dystrophy. In some embodiments, a subject has elevated expression of the DUX4 gene outside of fetal development and the testes. In some embodiments, the subject has facioscapulohumeral muscular dystrophy of Type I or Type II. In some embodiments, the subject having FSHD has mutations in the SMCHD1 gene. In some embodiments, the subject having FSHD has deletion mutations in D4Z4 repeat regions on chromosome 4.

An aspect of the disclosure includes a methods involving administering to a subject an effective amount of a complex as described herein. In some embodiments, an effective amount of a pharmaceutical composition that comprises a complex comprising a muscle-targeting agent covalently to a molecular payload can be administered to a subject in need of treatment. In some embodiments, a pharmaceutical composition comprising a complex as described herein may be administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a pharmaceutical composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

Compositions for intravenous administration may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In some embodiments, a pharmaceutical composition that comprises a complex comprising a muscle-targeting agent covalently to a molecular payload is administered via site-specific or local delivery techniques. Examples of these techniques include implantable depot sources of the complex, local delivery catheters, site specific carriers, direct injection, or direct application.

In some embodiments, a pharmaceutical composition that comprises a complex comprising a muscle-targeting agent covalently to a molecular payload is administered at an effective concentration that confers therapeutic effect on a subject. Effective amounts vary, as recognized by those skilled in the art, depending on the severity of the disease, unique characteristics of the subject being treated, e.g. age, physical conditions, health, or weight, the duration of the treatment, the nature of any concurrent therapies, the route of administration and related factors. These related factors are known to those in the art and may be addressed with no more than routine experimentation. In some embodiments, an effective concentration is the maximum dose that is considered to be safe for the patient. In some embodiments, an effective concentration will be the lowest possible concentration that provides maximum efficacy.

Empirical considerations, e.g. the half-life of the complex in a subject, generally will contribute to determination of the concentration of pharmaceutical composition that is used for treatment. The frequency of administration may be empirically determined and adjusted to maximize the efficacy of the treatment.

Generally, for administration of any of the complexes described herein, an initial candidate dosage may be about 1 to 100 mg/kg, or more, depending on the factors described above, e.g. safety or efficacy. In some embodiments, a treatment will be administered once. In some embodiments, a treatment will be administered daily, biweekly, weekly, bimonthly, monthly, or at any time interval that provide maximum efficacy while minimizing safety risks to the subject. Generally, the efficacy and the treatment and safety risks may be monitored throughout the course of treatment The efficacy of treatment may be assessed using any suitable methods. In some embodiments, the efficacy of treatment may be assessed by evaluation of observation of symptoms associated with FSHD including muscle mass loss and muscle atrophy, primarily in the muscles of the face, shoulder blades, and upper arms.

In some embodiments, a pharmaceutical composition that comprises a complex comprising a muscle-targeting agent covalently to a molecular payload described herein is administered to a subject at an effective concentration sufficient to inhibit activity or expression of a target gene by at least 10%, at least 20%, at least 30%, at least 40%, at least 50%, at least 60%, at least 70%, at least 80%, at least 90% or at least 95% relative to a control, e.g. baseline level of gene expression prior to treatment.

Hepa 1-6 cells in culture and the cells were maintained for 48 hours. As shown in FIG. 1, it was found that the HPRT siRNA reduced HPRT expression levels by ~90% compared with controls.

TABLE 2

Sequences of siHPRT and siCTRL

| | Sequence | SEQ ID NO: |
|---|---|---|
| siHPRT sense strand | 5'-UcCuAuGaCuGuAgAuUuUaU-(CH$_2$)$_6$NH$_2$-3' | 48 |
| siHPRT antisense strand | 5'-paUaAaAuCuAcAgUcAuAgGasAsu-3' | 49 |
| siCTRL sense strand | 5'-UgUaAuAaCcAuAuCuAcCuU-(CH$_2$)$_6$NH$_2$-3' | 50 |
| siCTRL antisense strand | 5'-aAgGuAgAuAuGgUuAuUaCasAsa-3' | 51 |

*Lower case-2'-Ome ribose; Capital letter-2'Fluoro ribose; p-phosphate linkage; s-phosphorothioate linkage In some embodiments, a single dose or administration of a pharmaceutical composition that comprises a complex comprising a muscle-targeting agent covalently to a molecular payload described herein to a subject is sufficient to inhibit activity or expression of a target gene for at least 1-5, 1-10, 5-15, 10-20, 15-30, 20-40, 25-50, or more days. In some embodiments, a single dose or administration of a pharmaceutical composition that comprises a complex comprising a muscle-targeting agent covalently to a molecular payload described herein to a subject is sufficient to inhibit activity or expression of a target gene for at least 1, 2, 3, 4, 5, 6, 7, 8, 9, 10, 11, or 12 weeks. In some embodiments, a single dose or administration of a pharmaceutical composition that comprises a complex comprising a muscle-targeting agent covalently to a molecular payload described herein to a subject is sufficient to inhibit activity or expression of a target gene for at least 1, 2, 3, 4, 5, or 6 months.

In some embodiments, a pharmaceutical composition may comprises more than one complex comprising a muscle-targeting agent covalently to a molecular payload. In some embodiments, a pharmaceutical composition may further comprise any other suitable therapeutic agent for treatment of a subject, e.g. a human subject having FSHD. In some embodiments, the other therapeutic agents may enhance or supplement the effectiveness of the complexes described herein. In some embodiments, the other therapeutic agents may function to treat a different symptom or disease than the complexes described herein.

EXAMPLES

Example 1: Targeting Gene Expression with Transfected Antisense Oligonucleotides A siRNA that targets hypoxanthine phosphoribosyltransferase (HPRT) was tested in vitro for its ability to reduce expression levels of HPRT in an immortalized cell line. Briefly, Hepa 1-6 cells were transfected with either a control siRNA (siCTRL; 100 nM) or the siRNA that targets HPRT (siHPRT; 100 nM), formulated with lipofectamine 2000. HPRT expression levels were evaluated 48 hours following transfection. A control experiment was also performed in which vehicle (phosphate-buffered saline) was delivered to Example 2: Targeting HPRT with a Muscle-Targeting Complex A muscle-targeting complex was generated comprising the HPRT siRNA used in Example 1 (siHPRT) covalently linked, via a non-cleavable N-gamma-maleimidobutyryl-oxysuccinimide ester (GMBS) linker, to DTX-A-002, an anti-transferrin receptor antibody.

Briefly, the GMBS linker was dissolved in dry DMSO and coupled to the 3' end of the sense strand of siHPRT through amide bond formation under aqueous conditions. Completion of the reaction was verified by Kaiser test. Excess linker and organic solvents were removed by gel permeation chromatography. The purified, maleimide functionalized sense strand of siHPRT was then coupled to DTX-A-002 antibody using a Michael addition reaction.

The product of the antibody coupling reaction was then subjected to hydrophobic interaction chromatography (HIC-HPLC). antiTfR-siHPRT complexes comprising one or two siHPRT molecules covalently attached to DTX-A-002 antibody were purified. Densitometry confirmed that the purified sample of complexes had an average siHPRT to antibody ratio of 1.46. SDS-PAGE analysis demonstrated that >90% of the purified sample of complexes comprised DTX-A-002 linked to either one or two siHPRT molecules.

Using the same methods as described above, a control IgG2a-siHPRT complex was generated comprising the HPRT siRNA used in Example 1 (siHPRT) covalently linked via the GMBS linker to an IgG2a (Fab) antibody (DTX-A-003). Densitometry confirmed that DTX-C-001 had an average siHPRT to antibody ratio of 1.46 and SDS-PAGE demonstrated that >90% of the purified sample of control complexes comprised DTX-A-003 linked to either one or two siHPRT molecules.

Figure 2:
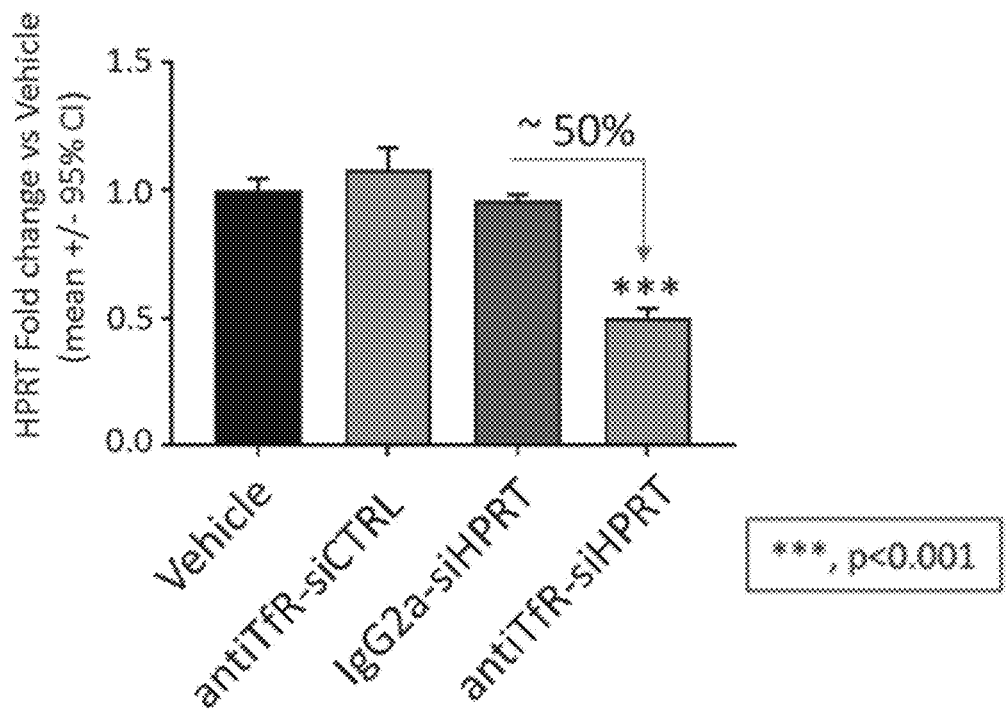
FIG. 2 depicts a non-limiting schematic showing the activity of a muscle targeting complex comprising an siRNA.

The antiTfR-siHPRT complex was then tested for cellular internalization and inhibition of HPRT in cellulo. Hepa 1-6 cells, which have relatively high expression levels of transferrin receptor, were incubated in the presence of vehicle (phosphate-buffered saline), IgG2a-siHPRT (100 nM), anti-TfR-siCTRL (100 nM), or antiTfR-siHPRT (100 nM), for 72 hours. After the 72 hour incubation, the cells were isolated and assayed for expression levels of HPRT (FIG. 2). Cells treated with the antiTfR-siHPRT demonstrated a reduction in HPRT expression by ~50% relative to the cells treated with the vehicle control. Meanwhile, cells treated with either of the IgG2a-siHPRT or antiTfR-siCTRL had HPRT expression levels comparable to the vehicle control (no reduction in HPRT expression). These data indicate that the anti-transferrin receptor antibody of the antiTfR-siHPRT enabled cellular internalization of the complex, thereby allowing the siHPRT to inhibit expression of HPRT.

Example 3: Targeting HPRT in Mouse Muscle Tissues with a Muscle-Targeting Complex The muscle-targeting complex described in Example 2, antiTfR-siHPRT, was tested for inhibition of HPRT in mouse tissues. C57BL/6 wild-type mice were intravenously injected with a single dose of a vehicle control (phosphate-buffered saline); siHPRT (2 mg/kg of RNA); IgG2a-siHPRT (2 mg/kg of RNA, corresponding to 9 mg/kg antibody complex); or antiTfR-siHPRT (2 mg/kg of RNA, corresponding to 9 mg/kg antibody complex. Each experimental condition was replicated in four individual C57BL/6 wild-type mice. Following a three-day period after injection, the mice were euthanized and segmented into isolated tissue types. Individual tissue samples were subsequently assayed for expression levels of HPRT (FIGS. 3A-3B and 4A-4E).

Figure 3A:
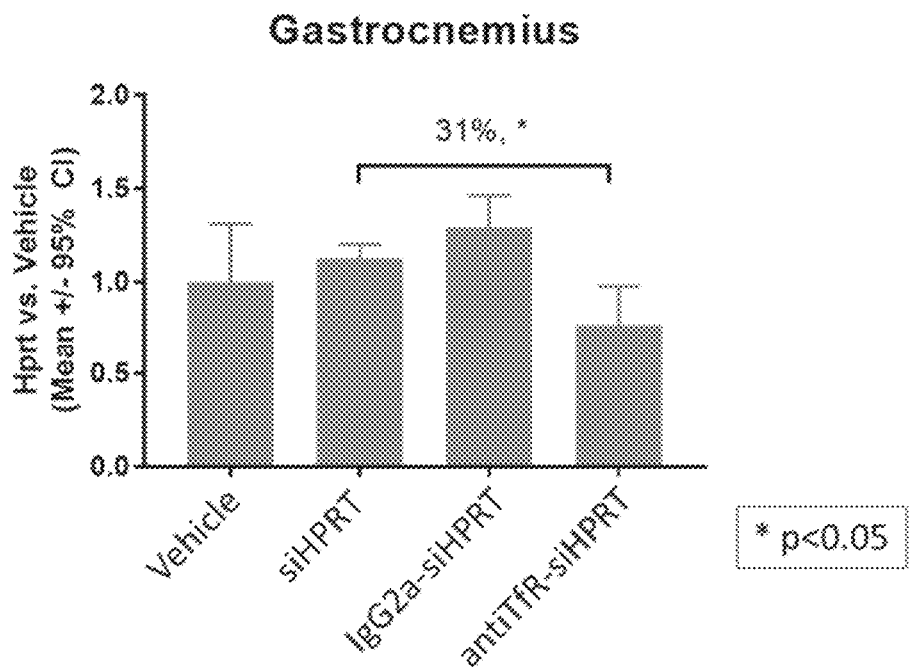
FIGS. 3A-3B depict non-limiting schematics showing the activity of a muscle targeting complex comprising an siRNA in mouse muscle tissues (gastrocnemius and heart) in vivo, relative to control experiments. (N=4 C57BL/6 WT mice)
Figure 3B:
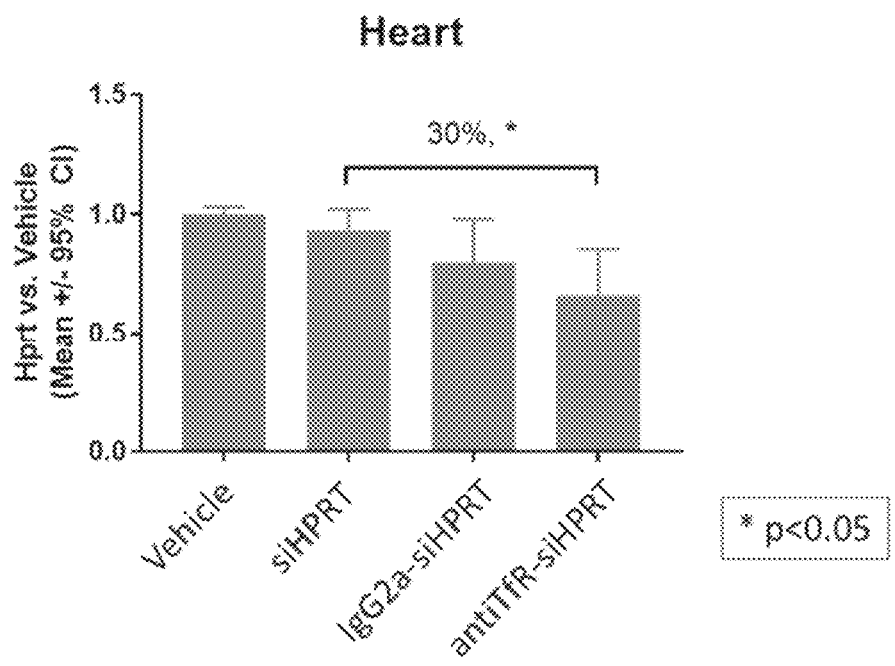
Figure 4A:
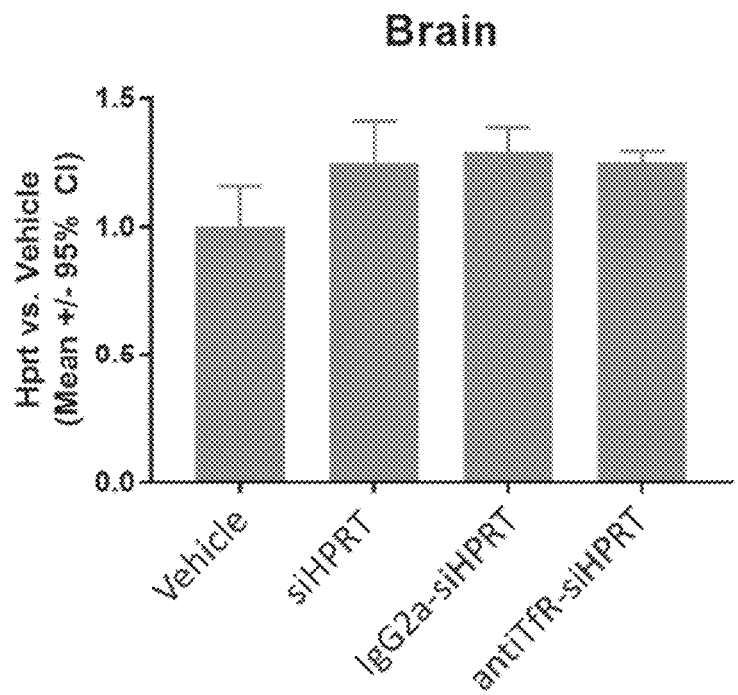
FIGS. 4A-4E depict non-limiting schematics showing the tissue selectivity of a muscle targeting complex comprising an siRNA.
Figure 4B:
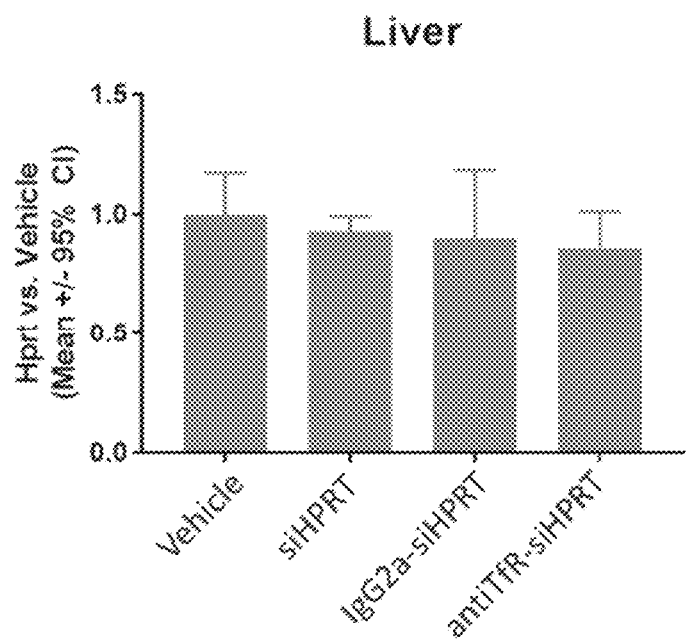
Figure 4C:
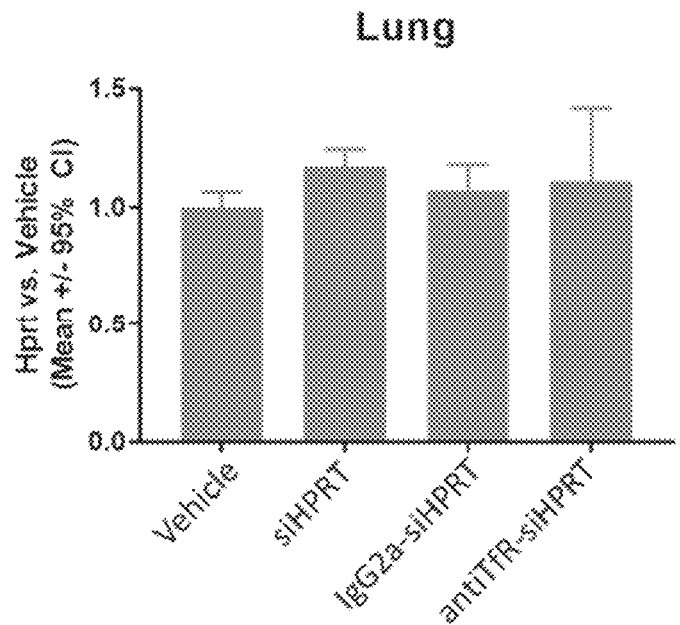
Figure 4D:
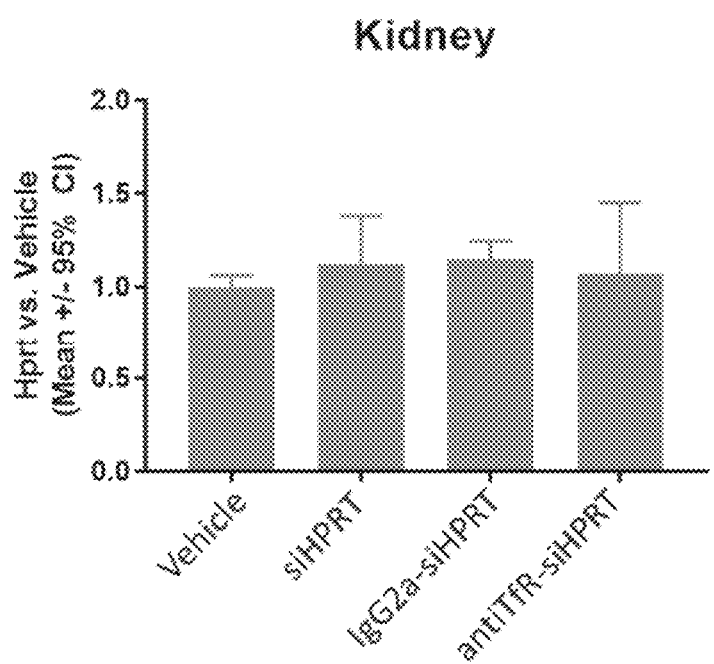
Figure 4E:
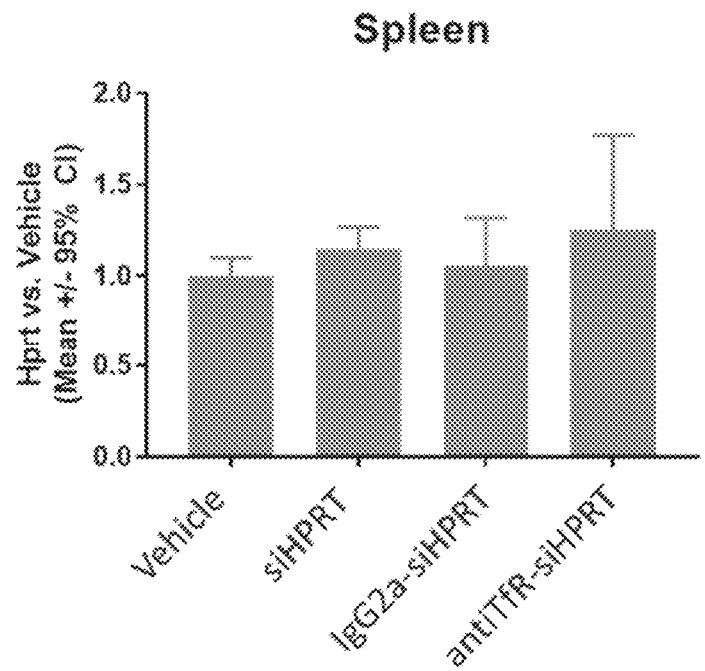

Mice treated with the antiTfR-siHPRT complex demonstrated a reduction in HPRT expression in gastrocnemius (31% reduction; p<0.05) and heart (30% reduction; p<0.05), relative to the mice treated with the siHPRT control (FIGS. 3A-3B). Meanwhile, mice treated with the IgG2a-siHPRT complex had HPRT expression levels comparable to the siHPRT control (little or no reduction in HPRT expression) for all assayed muscle tissue types.

Mice treated with the antiTfR-siHPRT complex demonstrated no change in HPRT expression in non-muscle tissues such as brain, liver, lung, kidney, and spleen tissues (FIGS. 4A-4E).

These data indicate that the anti-transferrin receptor antibody of the antiTfR-siHPRT complex enabled cellular internalization of the complex into muscle-specific tissues in an in vivo mouse model, thereby allowing the siHPRT to inhibit expression of HPRT. These data further demonstrate that the antiTfR-oligonucleotide complexes of the current disclosure are capable of specifically targeting muscle tissues.

Example 4: Targeting DUX4 with Transfected Antisense Oligonucleotides

Figure 5:
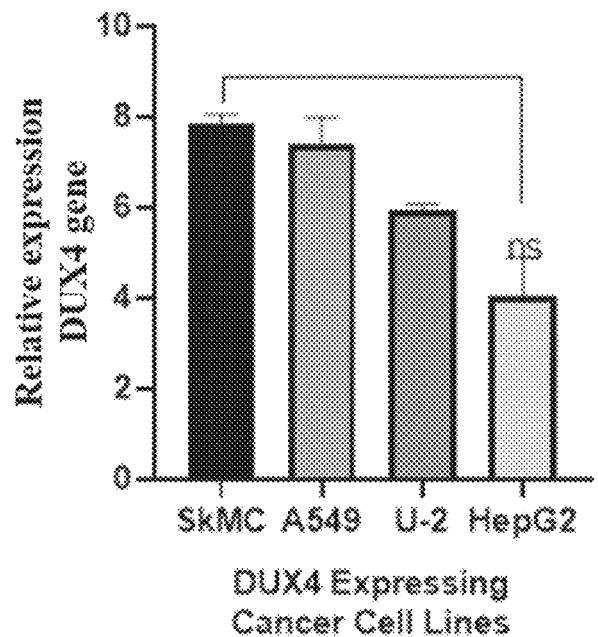
FIG. 5 depicts a non-limiting schematic showing the expression levels of DUX4 in three DUX4-expressing cell lines (A549, U-2 OS, and HepG2 cell lines) and immortalized skeletal muscle myoblasts (SkMC).

Three DUX4-expressing cell lines (A549, U-2 OS, and HepG2 cell lines) and immortalized skeletal muscle myoblasts (SkMC) were screened for expression of DUX4 mRNA (FIG. 5). Cells were seeded at a density of 10,000 cells/well and harvested for total RNA. cDNA was synthesized from the total RNA extracts and qPCR was performed to determine concentration of DUX4 relative to a control gene (PPIB) in technical quadruplicate. These data were used to aid in the selection of the U-2 OS cell line for downstream development of DUX4-targeting oligonucleotides.

Following selection of U-2 OS cells for development of DUX4-targeting oligonucleotides, a phosphorodiamidate morpholino oligomer (PMO) version of an antisense oligonucleotide that targets DUX4 (FM10 PMO) was evaluated for its ability to target DUX4 in vitro. FM10 PMO comprises the sequence GGGCATTTTAATATATCTCTGAACT (SEQ ID NO: 45). A control phosphorodiamidate morpholino oligomer (PMO), that comprises the sequence CCTCTTACCTCAGTTACAATTTATA (SEQ ID NO: 47), was utilized as a negative control.

Briefly, U-2 OS cells were seeded at a density of 10k cells/well before being allowed to recover overnight. Cells were then treated with either a control PMO (100 nM) or with the FM10 PMO (10 μM). Cells were incubated for 72 hours before being harvested for total RNA. cDNA was then synthesized from the total RNA extracts and qPCR was performed to determine expression of downstream DUX4 genes (ZSCAN1, MBDL3L2, TRIM43) in technical quadruplicate. All qPCR data were analyzed using a standard ΔΔCT method and were normalized to a plate-based negative control comprised of untreated cells (i.e., without any oligonucleotide). Results were then converted to fold change to evaluate efficacy.

Figure 6:
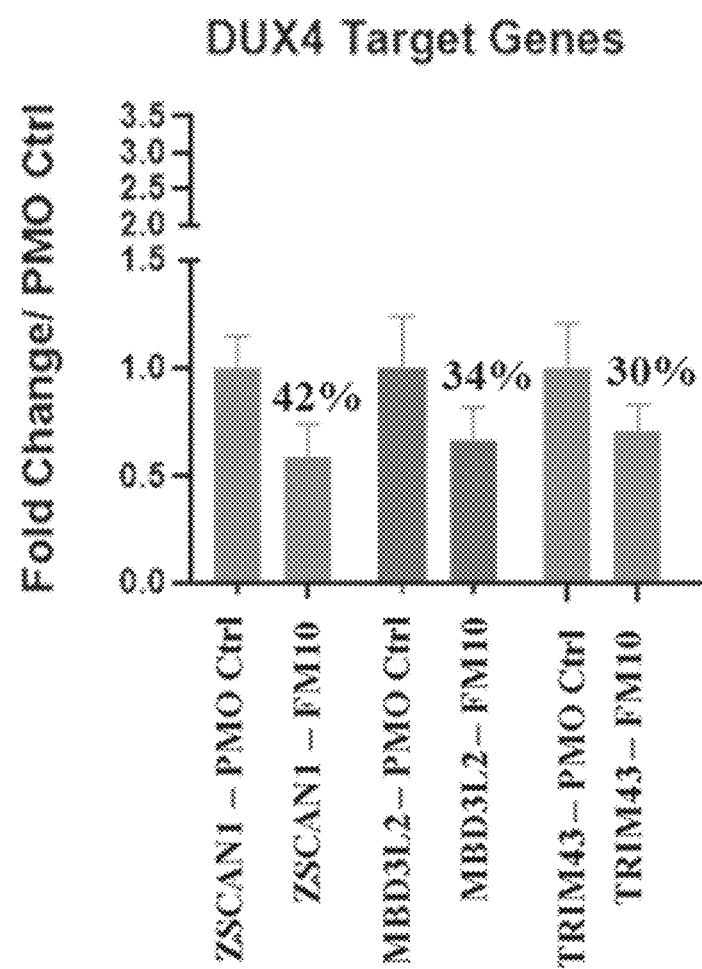
FIG. 6 depicts non-limiting schematics showing the ability of a phosphorodiamidate morpholino oligomer (PMO) version of an antisense oligonucleotide that targets DUX4 (FM10 PMO) to reduce expression levels of downstream DUX4 genes (ZSCAN1, MBDL3L2, TRIM43).

As shown in FIG. 6, all of ZSCAN1, MBDL3L2, and TRIM43 showed decreased expression in the presence of the FM10 PMO compared to the control PMO (42%, 34%, and 32%; respectively). These data demonstrate that the FM10 PMO is capable of targeting DUX4 in vitro.

Example 5: Targeting DUX4 with a Muscle-Targeting Complex

A muscle-targeting complex is generated comprising an antisense oligonucleotide that targets a mutant allele of DUX4 (DUX4 ASO) covalently linked, via a cathepsin cleavable linker, to DTX-A-002 (RI7 217 (Fab)), an anti-transferrin receptor antibody.

Briefly, a maleimidocaproyl-L-valine-L-citrulline-p-aminobenzyl alcohol p-nitrophenyl carbonate (MC-Val-Cit-PABC-PNP) linker molecule is coupled to $NH_2$-$C_6$-DUX4 ASO using an amide coupling reaction. Excess linker and organic solvents are removed by gel permeation chromatography. The purified Val-Cit-linker-DUX4 ASO is then coupled to a thiol-reactive anti-transferrin receptor antibody (DTX-A-002).

The product of the antibody coupling reaction is then subjected to hydrophobic interaction chromatography (HIC-HPLC) to purify the muscle-targeting complex. Densitometry and SDS-PAGE analysis of the purified complex allow for determination of the average ratio of ASO-to-antibody and total purity, respectively.

Using the same methods as described above, a control complex is generated comprising DUX4 ASO covalently linked via a Val-Cit linker to an IgG2a (Fab) antibody.

The purified muscle-targeting complex comprising DTX-A-002 covalently linked to DUX4 ASO is then tested for cellular internalization and inhibition of DUX4. Disease-relevant muscle cells that have relatively high expression levels of transferrin receptor, are incubated in the presence of vehicle control (saline), muscle-targeting complex (100 nM), or control complex (100 nM) for 72 hours. After the 72 hour incubation, the cells are isolated and assayed for expression levels of DUX4.

Equivalents and Terminology

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A method of delivering an oligonucleotide to a subject, wherein the subject has facioscapulohumeral muscular dystrophy, the method comprising intravenously administering to the subject a complex that comprises an anti-transferrin receptor antibody covalently linked to a 5' end or a 3' end of an oligonucleotide,
wherein the anti-transferrin receptor antibody binds in the range of C89 to F760 of human transferrin receptor protein 1 (TfR1) having an amino acid sequence as set forth in SEQ ID NO: 1 and wherein the anti-transferrin receptor antibody does not specifically bind to the transferrin binding site of TfR1;
wherein the oligonucleotide comprises one or more modifications and a single strand that comprises a region of complementarity of at least 15 nucleotides in length to the nucleotide sequence as set forth in SEQ ID NO: 52, wherein the oligonucleotide is in the range of 15-30 nucleotides in length;
wherein the one or more modifications comprise a 2'-modified nucleoside selected from the group consisting of: a 2'-O-methyl nucleoside, a 2'-fluoro nucleoside, a 2'-O-methoxyethyl nucleoside, a 2'-O-aminopropyl (2'-O-AP) nucleoside, a 2'-O-dimethylaminoethyl (2'-O-DMAOE) nucleoside, a 2'-O-dimethylaminopropyl (2'-O-DMAP) nucleoside, a 2'-O-dimethylaminoethyloxyethyl (2'-O-DMAEOE) nucleoside, a 2'-O-N-methylacetamido (2'-O-NMA) nucleoside, and 2',4'-bridged nucleosides, and combinations thereof, and/or comprise a modified backbone selected from a backbone comprising one or more phosphorothioate linkages and a phosphorodiamidate morpholino backbone.

2. The method of claim 1, wherein the region of complementarity is at least 16 nucleotides in length.

3. The method of claim 1, wherein the region of complementarity is at least 17 nucleotides in length.

4. The method of claim 1, wherein the region of complementarity is at least 18 nucleotides in length.

5. The method of claim 1, wherein the region of complementarity is at least 19 nucleotides in length.

6. The method of claim 1, wherein the region of complementarity is at least 20 nucleotides in length.

7. The method of claim 1, wherein the oligonucleotide is a phosphorodiamidate morpholino oligomer (PMO).

8. The method of claim 1, wherein the oligonucleotide is covalently linked to a lysine in the anti-transferrin receptor antibody via a cleavable linker.

9. The method of claim 8, wherein the cleavable linker comprises a valine-citrulline sequence.

10. The method of claim 9, wherein the complex is obtained by a cycloaddition reaction between an azide and an alkyne to form a triazole.

11. The method of claim 10, wherein, prior to the cycloaddition reaction, the azide is covalently linked to the valine-citrulline sequence of the cleavable linker that is covalently linked to the oligonucleotide and the alkyne is provided in a bicyclononyne moiety that further covalently links to the anti-transferrin receptor antibody.

12. The method of claim 9, wherein the cleavable linker further comprises one or more polyethylene glycol units.

13. The method of claim 1, wherein the anti-transferrin receptor antibody binds to human TfR1 with a KD in a range of $10^{-11}$ M to $10^{-8}$ M.

14. The method of claim 1, wherein the anti-transferrin receptor antibody is in the form of a ScFv, Fab fragment, Fab' fragment, F(ab')2 fragment, or Fv fragment.

15. The method of claim 1, wherein the anti-transferrin receptor antibody is in the form of a Fab fragment.

16. The method of claim 1, wherein the subject has one or more deletions of D4Z4 repeats in chromosome 4.

17. The method of claim 16, wherein the subject has 10 or fewer D4Z4 repeats.

18. The method of claim 1, wherein the oligonucleotide is delivered to a muscle cell of the subject.

19. The method of claim 18, wherein the muscle cell is a skeletal muscle cell, cardiac muscle cell, or smooth muscle cell.

20. The method of claim 1, wherein the subject is human.

21. The method of claim 1, wherein the subject is cynomolgus.

22. A method of delivering an oligonucleotide to a subject, wherein the subject has a muscular dystrophy, the method comprising intravenously administering to the subject a complex that comprises an anti-transferrin receptor antibody covalently linked to a 5' end or a 3' end of an oligonucleotide,
wherein the anti-transferrin receptor antibody binds in the range of C89 to F760 of human transferrin receptor protein 1 (TfR1) having an amino acid sequence as set forth in SEQ ID NO: 1 and wherein the anti-transferrin receptor antibody does not specifically bind to the transferrin binding site of TfR1;
wherein the oligonucleotide comprises one or more modifications and a single strand that comprises a region of complementarity of at least 15 nucleotides in length to an RNA encoded by a gene associated with the muscular dystrophy, wherein the oligonucleotide is in the range of 15-30 nucleotides in length;
wherein the one or more modifications comprise a 2'-modified nucleoside selected from the group consisting of: a 2'-O-methyl nucleoside, a 2'-fluoro nucleoside, a 2'-O-methoxyethyl nucleoside, a 2'-O-aminopropyl (2'-O-AP) nucleoside, a 2'-O-dimethylaminoethyl (2'-O-DMAOE) nucleoside, a 2'-O-dimethylaminopropyl (2'-O-DMAP) nucleoside, a 2'-O-dimethylaminoethyloxyethyl (2'-O-DMAEOE) nucleoside, a 2'-O-N-methylacetamido (2'-O-NMA) nucleoside, and 2',4'-bridged nucleosides, and combinations thereof, and/or comprise a modified backbone selected from a backbone comprising one or more phosphorothioate linkages and a phosphorodiamidate morpholino backbone.

23. The method of claim 22, wherein the anti-transferrin receptor antibody comprises a CDRH1, a CDRH2, a CDRH3, a CDRL1, a CDRL2, and a CDRL3 of an antibody selected from the group consisting of: OKT9, M11, M23, M27, B84, 7A4, 8A2, 15D2, 10D11, 7B10, 15G11, 16G5, 13C3, 16G4, 16F6, 7G7, 4C2, 1B12, 13D4, 8D3, OX26, DF1513, 1A1B2, 66IG10, MEM-189, JF0956, 29806, TFRC/1818, 1E6, 66Ig10, TFRC/1059, Q1/71, 23D10, 13E4, TFRC/1149, ER-MP21, YTA74.4, BU54, 2B6, RI7 217, BA120g, LUCA31, B3/25, T58/30, R17 217.1.3, 5E9C11, BE0023, BK19.9, B3/25, T56/14, and T58/1.

* * * * *